(12) United States Patent
Abeywardane et al.

(10) Patent No.: US 9,133,146 B2
(45) Date of Patent: *Sep. 15, 2015

(54) BENZODIOXANE INHIBITORS OF LEUKOTRIENE PRODUCTION

(71) Applicant: Boehringer Ingelheim International GmbH, Ingelheim am Rhein (DE)

(72) Inventors: Asitha Abeywardane, Danbury, CT (US); Michael J. Burke, Newtown, CT (US); Thomas Martin Kirrane, Jr., Middlebury, CT (US); Matthew Russell Netherton, Danbury, CT (US); Anil Kumar Padyana, Oxford, CT (US); Lana Louise Smith Keenan, Poughquag, NY (US); Hidenori Takahashi, LaGrangeville, NY (US); Michael Robert Turner, Danbury, CT (US); Qiang Zhang, Woodbury, CT (US); Qing Zhang, Tianjin (CN)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,879

(22) Filed: Aug. 23, 2013

(65) Prior Publication Data

US 2013/0345195 A1   Dec. 26, 2013

Related U.S. Application Data

(63) Continuation of application No. 13/418,377, filed on Mar. 13, 2012, now Pat. No. 8,551,982.

(60) Provisional application No. 61/452,329, filed on Mar. 14, 2011.

(51) Int. Cl.
| | | |
|---|---|---|
| A61K 31/397 | (2006.01) | |
| A61K 31/5377 | (2006.01) | |
| A61K 31/495 | (2006.01) | |
| A61K 31/496 | (2006.01) | |
| A61K 31/497 | (2006.01) | |
| A61K 31/55 | (2006.01) | |
| A61K 31/4427 | (2006.01) | |
| A61K 31/4523 | (2006.01) | |

(Continued)

(52) U.S. Cl.
CPC ............ *C07D 295/16* (2013.01); *A61K 31/397* (2013.01); *A61K 31/5377* (2013.01); *C07D 295/096* (2013.01); *C07D 319/20* (2013.01); *C07D 405/10* (2013.01); *C07D 405/12* (2013.01); *C07D 405/14* (2013.01); *C07D 417/10* (2013.01); *C07D 417/14* (2013.01); *C07D 471/10* (2013.01); *C07D 487/04* (2013.01); *C07D 487/08* (2013.01); *C07D 487/10* (2013.01); *C07D 491/056* (2013.01)

(58) Field of Classification Search
CPC ............ A61K 31/397; A61K 31/5377; A61K 31/495; A61K 31/496; A61K 31/497; A61K 31/55; A61K 31/4427; A61K 31/4523; A61K 31/4025; A61K 31/335; A61K 31/357; C07D 243/08; C07D 413/02; C07D 279/12; C07D 491/04; C07D 405/02; C07D 215/00; C07D 211/80; C07D 209/02; C07D 217/00; C07D 205/02; C07D 319/16; C07D 319/10
See application file for complete search history.

(56) References Cited

U.S. PATENT DOCUMENTS

| | | |
|---|---|---|
| 4,918,092 A | 4/1990 | Frenette et al. |
| 5,120,758 A | 6/1992 | Satoh |

(Continued)

FOREIGN PATENT DOCUMENTS

| | | |
|---|---|---|
| WO | 9610999 A2 | 4/1996 |
| WO | 9611192 A1 | 4/1996 |

(Continued)

OTHER PUBLICATIONS

Davies, D. R. et al., "Discovery of Leukotriene A4 Hydrolase Inhibitors Using Metabolomics Biased Fragment Crystallography +", Journal of Medicanal Chemistry, vol. 52, No. 15, Aug. 13, 2009, pp. 4694-4715.

(Continued)

*Primary Examiner* — Samantha Shterengarts
(74) *Attorney, Agent, or Firm* — Michael P. Morris; David L. Kershner; Usha R. Patel

(57) ABSTRACT

The present invention relates to compounds of formula (I):

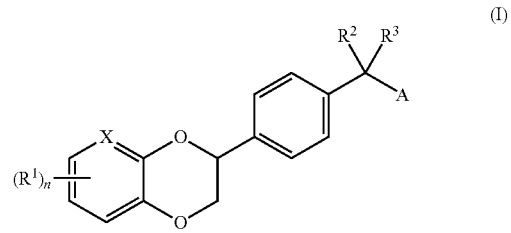

wherein $R^1$ to $R^3$, A, X and n are as defined herein. The compounds of formula (I) are useful as inhibitors of leukotriene $A_4$ hydrolase (LTA4H) and treating LTA4H related disorder. The present invention also relates to pharmaceutical compositions comprising the compounds of formula (I), methods of using these compounds in the treatment of various diseases and disorders, and processes for preparing these compounds.

5 Claims, No Drawings

(51) Int. Cl.
*A61K 31/4025* (2006.01)
*A61K 31/335* (2006.01)
*A61K 31/357* (2006.01)
*C07D 243/08* (2006.01)
*C07D 413/02* (2006.01)
*C07D 279/12* (2006.01)
*C07D 491/04* (2006.01)
*C07D 405/02* (2006.01)
*C07D 215/00* (2006.01)
*C07D 211/80* (2006.01)
*C07D 209/02* (2006.01)
*C07D 217/00* (2006.01)
*C07D 205/02* (2006.01)
*C07D 319/10* (2006.01)
*C07D 295/16* (2006.01)
*C07D 319/20* (2006.01)
*C07D 405/10* (2006.01)
*C07D 405/12* (2006.01)
*C07D 405/14* (2006.01)
*C07D 487/10* (2006.01)
*C07D 417/10* (2006.01)
*C07D 417/14* (2006.01)
*C07D 471/10* (2006.01)
*C07D 487/04* (2006.01)
*C07D 487/08* (2006.01)
*C07D 491/056* (2006.01)
*C07D 295/096* (2006.01)

(56) References Cited

U.S. PATENT DOCUMENTS

| | | | |
|---|---|---|---|
| 6,180,637 | B1 | 1/2001 | Schindler et al. |
| 7,098,222 | B2 | 8/2006 | Altenbach et al. |
| 7,429,665 | B2 | 9/2008 | Verhoest et al. |
| 7,674,802 | B2 | 3/2010 | Sandanayaka et al. |
| 8,551,982 | B2 | 10/2013 | Abeywardane et al. |
| 2002/0132822 | A1 | 9/2002 | Noe et al. |
| 2006/0019269 | A1 | 1/2006 | Helgadottir et al. |
| 2006/0223792 | A1 | 10/2006 | Butler et al. |
| 2007/0066820 | A1 | 3/2007 | Sandanayaka et al. |
| 2007/0149544 | A1 | 6/2007 | Sandanayaka et al. |
| 2013/0196973 | A1 | 8/2013 | Abeywardane et al. |
| 2013/0236468 | A1 | 9/2013 | Bylock |
| 2013/0244996 | A1 | 9/2013 | Abeywardane et al. |
| 2014/0031339 | A1 | 1/2014 | Abeywardane et al. |

FOREIGN PATENT DOCUMENTS

| | | |
|---|---|---|
| WO | 2004056369 A1 | 7/2004 |
| WO | 2007040682 A1 | 4/2007 |
| WO | 2011114220 A1 | 9/2011 |
| WO | 2012125598 A1 | 9/2012 |
| WO | 2013012844 A1 | 1/2013 |
| WO | 2014014874 A1 | 1/2014 |

OTHER PUBLICATIONS

Grice, C.A. et al., "Current Status of Leukotriene A4 Hydrolase Inhibitors". Expert Opinion on Therapeutic Patents, vol. 18, No. 12, Dec. 1, 2008, p. 1333-1350.

International Search Report and Written Opinion for PCT/US2012/028843 mailed May 7, 2012.

Minami, M. et al., "Molecular Cloning of a cDNA Coding for Human Leukotriene A4 Hydrolase". The Journal of Biological Chemistry, vol. 262, No. 29, 1987, p. 13873-13876.

Sandanayaka, V. et al., "Discovery of 4-[(2 S)-2-{[4-(4-Chlorophenoxy)phenoxy]methyl}-1-pyrrolidinyl]butanoic Acid (DG-051) as a Novel Leukotriene B4 Biosynthesis". Journal of Medicinal Chemistry, vol. 53, No. 2, Jan. 28, 2010, p. 573-585.

Sandanayaka, V. et al., "Discovery of novel leukotriene A4 hydrolase inhibitors based on piperidine and piperazine scaffolds". Bioorganice and Medicinal Chemistry Letters, Pergamon, Elsevier Science, GB, vol. 20, No. 9, May 1, 2010, pp. 2851-2854.

Thangapandian, Sundarapandian et al., "Molecular Docking and Pharacophore Filtering in the Discovery of Dual-Inhibitors for Human Leukotreine A4 Hydrolase and Leukotriene C4 Synthase", Journal of Chemical Information and Modeling, vol. 51, No. 1, Jan. 24, 2011, pp. 33-44.

U.S. Appl. No. 14/330,297, filed Jul. 14, 2014—Inhibitors of Leukotriene Production. Inventor: Asitha Abeywardane et al.

U.S. Appl. No. 14/330,307, filed Jul. 14, 2014—Inhibitors of Leukotriene Production. Inventor: Asitha Abeywardane et al.

BENZODIOXANE INHIBITORS OF LEUKOTRIENE PRODUCTION

FIELD OF THE INVENTION

This invention relates to benzodioxanes that are useful as inhibitors of leukotriene $A_4$ hydrolase ($LTA_4H$) and are thus useful for treating a variety of diseases and disorders that are mediated or sustained through the activity of leukotrienes including asthma, allergy and cardiovascular diseases including atherosclerosis, myocardial infarction and stroke. This invention also relates to pharmaceutical compositions comprising these compounds, methods of using these compounds in the treatment of various diseases and disorders, to processes for preparing these compounds and intermediates useful in these processes.

BACKGROUND OF THE INVENTION

Leukotrienes (LT) are oxidized lipids that are produced by several cell types including neutrophils, mast cells, eosinophils, basophils, monocytes and macrophages. The first committed step in the intracellular synthesis of LTs involves oxidation of arachidonic acid by 5-lipoxygenase (5-LO) to leukotriene $A_4$ ($LTA_4$), a process requiring the 5-lipoxygenase-activating protein (FLAP). Leukotriene $A_4$ hydrolase ($LTA_4H$) catalyzes the hydrolysis of $LTA_4$ to produce leukotriene $B_4$ ($LTB_4$). Through the engagement of the $LTB_4$ receptors (BLT1, BLT2), $LTB_4$ stimulates an array of pro-inflammatory responses (leukocyte chemotaxis, cytokine release, etc.). The leukotriene pathway has been implicated in diseases in which inflammation is a critical component of the pathology; these include cancer, asthma, atherosclerosis, colitis, glomerularnephritis, and pain (for a review, see M. Peters-Golden and W. R. Henderson, Jr., M. D., N. Engl. J. Med., 2007, 357, 1841-1854).

BRIEF SUMMARY OF THE INVENTION

The present invention provides novel compounds which inhibit leukotriene $A_4$ hydrolase ($LTA_4H$) and are thus useful for treating a variety of diseases and disorders that are mediated or sustained through the activity of leukotrienes, including allergic, pulmonary, fibrotic, inflammatory and cardiovascular diseases and cancer.

In one embodiment, the invention relates to a compound of formula (I):

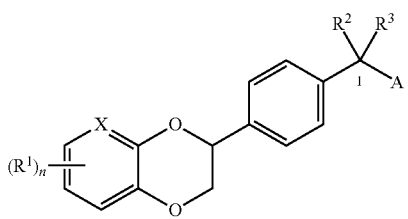

or a pharmaceutically acceptable salt thereof, wherein:
X is N or CH;
n is an integer from 0 to 3;
$R^1$ is selected from halo, —OH, —CN, —($C_1$-$C_6$)alkyl, —O($C_1$-$C_6$)alkyl, and —($C_3$-$C_6$)cycloalkyl;
$R^2$ and $R^3$ are each independently selected elected from —H and —($C_1$-$C_6$)alkyl; wherein $R^2$ and $R^3$ may join to form a 3- to 6-membered ring optionally comprising one to three heteroatoms, and further optionally substituted with one to three groups selected from halo, —OH, (=O), —($C_1$-$C_6$)alkyl, —O($C_1$-$C_6$)alkyl, —C(O)OH, —C(O)($C_1$-$C_6$)alkyl, and —C(O)$NH_2$;
A is a group of formula —$NR^4R^5$, wherein
$R^4$ and $R^5$ are each independently selected from —H, —($C_1$-$C_6$)alkyl, —($C_3$-$C_6$)cycloalkyl, -(4- to 11-membered)heterocycloalkyl, —($C_6$-$C_{10}$)aryl, and -(5- to 11-membered)heteroaryl; wherein each of the foregoing —($C_1$-$C_6$)alkyl, —($C_3$-$C_6$)cycloalkyl, -(4- to 11-membered)heterocycloalkyl, —($C_6$-$C_{10}$)aryl, and -(5- to 11-membered)heteroaryl of said $R^4$ and $R^5$ groups is optionally independently substituted by one to three $R^6$ groups; wherein two $R^6$ groups when attached to the same carbon atom of said —($C_1$-$C_6$)alkyl may join to form a 3- to 6-membered ring optionally comprising one to three heteroatoms, and further optionally substituted with one to three groups selected from halo, —OH, (=O), —($C_1$-$C_6$)alkyl, —O($C_1$-$C_6$)alkyl, —C(O)OH, —C(O)($C_1$-$C_6$)alkyl, and —C(O)$NH_2$;
or A is a (4- to 11-membered)N-heterocyclic ring of formula B:

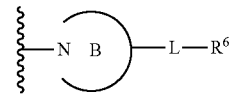

wherein said ring B may be a non-aromatic 4 to 8-membered monocyclic radical; a bridged bicyclic radical; a spirocyclic radical; or a 6 to 11-membered fused bicyclic radical which may be non-aromatic or have one aromatic ring provided that the aromatic ring of the bicyclic radical, when present, is not attached to methylene carbon atom 1 of the compound of formula (I);
wherein said ring B may additionally comprise one to three additional ring heteroatoms independently selected from N, O and S;
wherein said ring B may be further optionally substituted by one to three groups selected from halo, —OH, (=O), —C(O)OH, —C(O)O—($C_1$-$C_6$)alkyl, and —($C_1$-$C_6$) alkyl; and
wherein L is absent or a linker selected from —($C_1$-$C_6$) alkylene;
each $R^6$ is independently selected from halo, —$OR^7$, —$CF_3$, —CN, —($C_1$-$C_6$)alkyl, —C(O)$R^7$, —C(O)$_2R^7$, —C(O)N($R^7$)$_2$, —N($R^7$)$_2$, —NHC(O)$R^7$, —NHC(O)N($R^7$)$_2$, —S(O)$_2R^7$, —NH—S(O)$_2$—$R^7$, —($C_3$-$C_6$)cycloalkyl, -(4- to 11-membered)heterocycloalkyl, —($C_6$-$C_{10}$)aryl, and -(5- to 11-membered)heteroaryl; wherein each of said, —($C_1$-$C_6$) alkyl, —O($C_1$-$C_6$)alkyl, —($C_3$-$C_6$)cycloalkyl, -(4- to 11-membered)heterocycloalkyl, —($C_6$-$C_{10}$)aryl, and -(5- to 11-membered)heteroaryl of said $R^6$ group is optionally substituted where possible with one to three groups selected from halo, —OH, —$CF_3$, —CN, (=O), —($C_1$-$C_6$)alkyl, —C(O) OH, —C(O)O—($C_1$-$C_6$)alkyl, —$NH_2$, —NH($C_1$-$C_6$)alkyl, —N(($C_1$-$C_6$)alkyl)$_2$, —S(O)$_2$($C_1$-$C_6$)alkyl, —($C_3$-$C_6$)cycloalkyl, -(4- to 11-membered)heterocycloalkyl, —($C_6$-$C_{10}$) aryl, and -(5- to 11-membered)heteroaryl; and
each $R^7$ is independently selected from —H, —($C_1$-$C_6$)alkyl, —($C_1$-$C_6$)alkyl, —($C_1$-$C_6$)alkyl-OH, —($C_1$-$C_6$)alkyl-O—($C_1$-$C_6$)alkyl, —($C_3$-$C_6$)cycloalkyl, —($C_3$-$C_6$)cycloalkyl-OH, -(4- to 11-membered)heterocycloalkyl, —($C_6$-$C_{10}$)aryl, and -(5- to 11-membered)heteroaryl.

This invention also relates to pharmaceutical compositions comprising the compounds of formula (I), methods of using these compounds in the treatment of various diseases and disorders, processes for preparing these compounds and intermediates useful in these processes.

DETAILED DESCRIPTION OF THE INVENTION

Definitions

DCE=dichloroethane
DCM=dichloromethane
DEA=diethylamine
DIBAL-H=diisobutylaluminum hydride
DIPEA=diisopropylethylamine
DMA=dimethylacetamide
DMAP=4-dimethylaminopyridine
DME=dimethyl ether
DMF=dimethylformamide
DMSO=dimethylsulfoxide
$Et_2O$=ethylether
EtOAc=ethyl acetate
EtOH=ethanol
IPA=isopropyl alcohol
KHMDS=potassium bis(trimethylsilyl)amide
MeCN=acetonitrile
MeOH=methanol
TBTU=2-(1H-benzotriazole-1-yl)-1,1,3,3-tetramethyluronium tetrafluoroborate
TEA=triethylamine
TFA=trifluoroacetic acid
THF=tetrahydrofuran
$TMSCF_3$=(trifluoromethyl)trimethylsilane It will be understood that the terms "compounds of formula (I)" and "compounds of the invention" have the same meaning unless indicated otherwise.

In its broadest embodiment ("the first embodiment of the invention"), the invention relates to compounds of formula (I) as described above, and pharmaceutically acceptable salts thereof, as described above in the summary of the invention.

In another embodiment ("the second embodiment of the invention"), the invention relates to a compound of formula (I) as described in the first embodiment immediately of the invention, or a pharmaceutically acceptable salt thereof, wherein group A is a group of formula —$NR^4R^5$.

In another embodiment ("the third embodiment of the invention"), the invention relates to a compound of formula (I) as described in the first embodiment of the invention, or a pharmaceutically acceptable salt thereof, wherein group A is a (4- to 11-membered) N-heterocyclic ring of formula B:

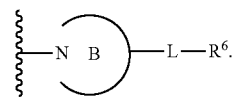

In another embodiment, the invention relates to a compound of formula (I) as described in the second embodiment of the invention, or a pharmaceutically acceptable salt thereof, wherein $R^4$ is —H or —($C_1$-$C_6$)alkyl, and $R^5$ is —($C_1$-$C_6$)alkyl; wherein each —($C_1$-$C_6$)alkyl of said $R^4$ and $R^5$ groups, when present, is optionally independently substituted by one to three $R^6$ groups.

In another embodiment, the invention relates to a compound of formula (I) as described in the embodiment immediately above, or a pharmaceutically acceptable salt thereof, wherein $R^4$ is —H or —($C_1$-$C_6$)alkyl, and $R^5$ is —($C_1$-$C_6$) alkyl; wherein said —($C_1$-$C_6$)alkyl of said $R^5$ group is substituted by —($C_3$-$C_6$)cycloalkyl, -(4- to 11-membered)heterocycloalkyl, —($C_6$-$C_{10}$)aryl, or -(5- to 11-membered) heteroaryl; wherein each of said, —($C_3$-$C_6$)cycloalkyl, -(4- to 11-membered)heterocycloalkyl, —($C_6$-$C_{10}$)aryl, and -(5- to 11-membered)heteroaryl is optionally substituted with one to three groups independently selected from —($C_1$-$C_6$)alkyl, —$CF_3$, and —C(O)$OR^8$.

In another embodiment, the invention relates to a compound of formula (I) as described in the second embodiment of the invention, or a pharmaceutically acceptable salt thereof, wherein $R^4$ is —H or —($C_1$-$C_6$)alkyl, and $R^5$ is —($C_1$-$C_6$)alkyl; wherein said —($C_1$-$C_6$)alkyl of said $R^5$ group is independently substituted by one to three groups selected from —($C_1$-$C_6$)alkyl, —O($C_1$-$C_6$)alkyl, —C(O)$R^8$, —C(O)$OR^8$, —S(O)$_2R^8$, and —NHC(O)$R^8$.

In another embodiment, the invention relates to a compound of formula (I) as described in the second embodiment of the invention, or a pharmaceutically acceptable salt thereof, wherein $R^4$ and $R^5$ are each independently selected from H or —($C_1$-$C_6$)alkyl.

In another embodiment, the invention relates to a compound of formula (I) as described in the second embodiment of the invention, or a pharmaceutically acceptable salt thereof, wherein $R^4$ is H or —($C_1$-$C_6$)alkyl, and $R^5$ is —($C_3$-$C_6$)cycloalkyl, -(4- to 11-membered)heterocycloalkyl, —($C_6$-$C_{10}$)aryl, and -(5- to 11-membered)heteroaryl; wherein each of the foregoing —($C_3$-$C_6$)cycloalkyl, -(4- to 11-membered)heterocycloalkyl, —($C_6$-$C_{10}$)aryl, and -(5- to 11-membered)heteroaryl groups of said $R^5$ is optionally independently substituted by one to three groups selected from —($C_1$-$C_6$)alkyl, —O($C_1$-$C_6$)alkyl, —C(O)$R^8$, —C(O)$OR^8$, —S(O)$_2R^8$, and —NHC(O)$R^8$.

In another embodiment, the invention relates to a compound of formula (I) as described in the third embodiment of the invention, or a pharmaceutically acceptable salt thereof, wherein said ring B is 4 to 8-membered monocyclic radical.

In another embodiment, the invention relates to a compound of formula (I) as described in the embodiment immediately above, or a pharmaceutically acceptable salt thereof, wherein said 4 to 8-membered monocyclic radical is selected from the group consisting of azetidine, tetrahydropyrrole, piperidine, hexamethyleneimine, 1,2-diazetidine, pyrazolidine, imidazolidine, piperazine, hexahydrodiazepine, isoxazolidine, oxazolidine, tetrahydro-2H-1,3-oxazine, morpholine, and hexahydro-1,4-oxazepine; wherein said monocyclic ring may be further optionally substituted by one to three groups selected from halo, —OH, (=O), —C(O)OH, —C(O)O—($C_1$-$C_6$)alkyl, and —($C_1$-$C_6$)alkyl.

In another embodiment, the invention relates to a compound of formula (I) as described in the third embodiment of the invention, or a pharmaceutically acceptable salt thereof, wherein said ring B is a spirocyclic heterocyclic radical.

In another embodiment, the invention relates to a compound of formula (I) as described in the embodiment immediately above, or a pharmaceutically acceptable salt thereof, wherein to said spirocyclic heterocyclic radical is selected from:

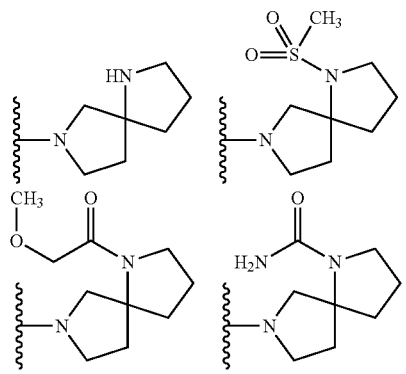

5
-continued

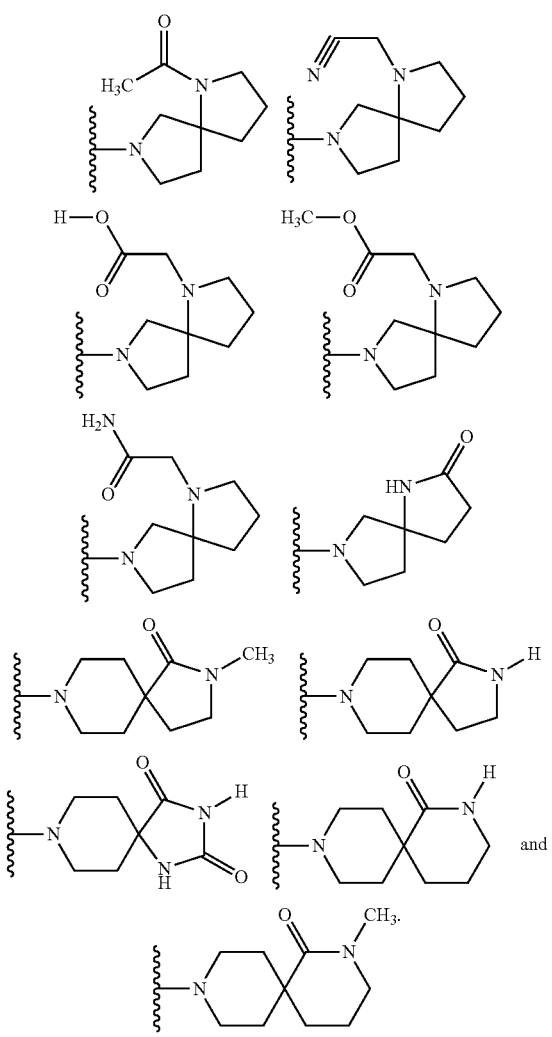

6
-continued

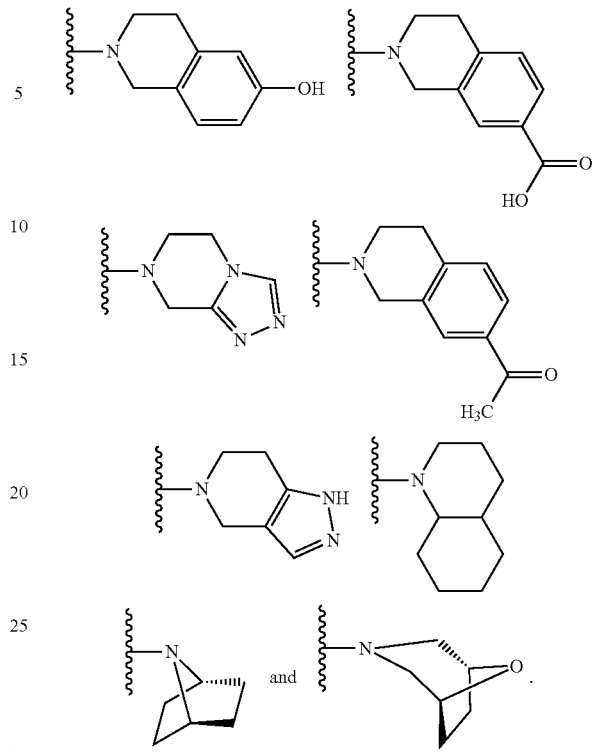

In another embodiment, the invention relates to a compound of formula (I) as described in the third embodiment of the invention, or a pharmaceutically acceptable salt thereof, wherein said ring B is a bridged bicyclic radical; or a 6 to 11-membered fused bicyclic radical which may be non-aromatic or have one aromatic ring provided that the aromatic ring of the bicyclic radical, when present, is not attached to methylene carbon atom 1 of the compound of formula (I).

In another embodiment, the invention relates to a compound of formula (I) as described in the embodiment immediately above, or a pharmaceutically acceptable salt thereof, wherein said 6 to 11-membered fused bicyclic radical or bridged bicyclic radical is selected from:

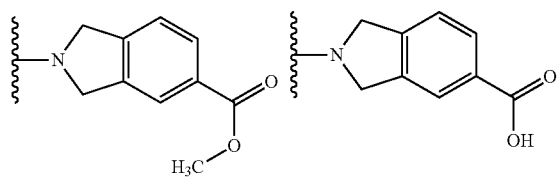

In another embodiment, the invention relates to a compound of formula (I) as described in the third embodiment of the invention, or a pharmaceutically acceptable salt thereof, wherein L is —CH$_2$—.

In another embodiment, the invention relates to a compound of formula (I) as described in the third embodiment of the invention, or a pharmaceutically acceptable salt thereof, wherein L is absent.

In another embodiment, the invention relates to a compound of formula (I) as described in the third embodiment of the invention, or a pharmaceutically acceptable salt thereof, wherein said 4 to 8-membered heterocyclic ring B is a selected from azetidinyl, pyrrolidinyl, piperidinyl and azepanyl; wherein each of the foregoing azetidinyl, pyrrolidinyl, piperidinyl and azepanyl rings is optionally substituted by one to three groups selected from halo, —OH, (=O), —C(O)OH, C(O)O—(C$_1$-C$_6$)alkyl, and —(C$_1$-C$_6$)alkyl; and wherein L is absent or a linker selected from —(C$_1$-C$_6$)alkylene; and wherein R$^6$ is elected from halo, —OR$^7$, —CF$_3$, —CN, —(C$_1$-C$_6$) alkyl, —C(O)R$^7$, —C(O)$_2$R$^7$, —C(O)N(R$^7$)$_2$, —N(R$^7$)$_2$, —NHC(O)R$^7$, —NHC(O)N(R$^7$)$_2$, —S(O)$_2$ R$^7$, —NH—S(O)$_2$—R$^7$, —(C$_3$-C$_6$)cycloalkyl, -(4- to 11-membered)heterocycloalkyl, —(C$_6$-C$_{10}$)aryl, and -(5- to 11-membered)heteroaryl; wherein each of said, —(C$_1$-C$_6$)alkyl, —O(C$_1$-C$_6$)alkyl, —(C$_3$-C$_6$)cycloalkyl, -(4- to 11-membered)heterocycloalkyl, —(C$_6$-C$_{10}$)aryl, and -(5- to 11-membered)heteroaryl of said R$^6$ group is optionally substituted where possible with one to three groups selected from halo, —OH, —CF$_3$, —CN, (=O), —(C$_1$-C$_6$)alkyl, —C(O)OH, —C(O)O—(C$_1$-C$_6$)alkyl, —NH$_2$, —NH(C$_1$-C$_6$)alkyl, —N((C$_1$-C$_6$)

alkyl)$_2$, —S(O)$_2$(C$_1$-C$_6$)alkyl, —(C$_3$-C$_6$)cycloalkyl, -(4- to 11-membered)heterocycloalkyl, —(C$_6$-C$_{10}$)aryl, and -(5- to 11-membered)heteroaryl.

In another embodiment, the invention relates to a compound of formula (I) as described in any of the embodiments above, or a pharmaceutically acceptable salt thereof, wherein X is N.

In another embodiment, the invention relates to a compound of formula (I) as described in any of the embodiments above except the embodiment immediately above, or a pharmaceutically acceptable salt thereof, wherein X is CH.

The following are representative compounds of the invention which were made by the general synthetic schemes, the examples, and known methods in the art.

TABLE 1

Exemplary compounds of the invention.

| Cpd No. | Structure | Name |
|---|---|---|
| 1 | 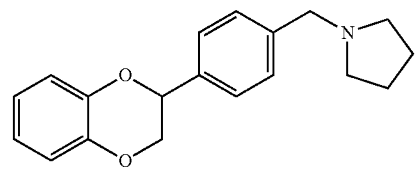 [SMILES: c1ccc2c(c1)OCC(c1ccc(CN3CCCC3)cc1)O2] | 1-[4-(2,3-dihydro-1,4-benzodioxin-2-yl)benzyl]pyrrolidine |
| 2 | 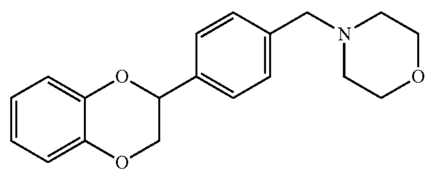 [SMILES: c1ccc2c(c1)OCC(c1ccc(CN3CCOCC3)cc1)O2] | 4-[4-(2,3-dihydro-1,4-benzodioxin-2-yl)benzyl]morpholine |
| 3 | 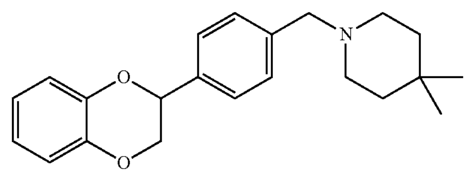 [SMILES: CC1(C)CCN(Cc2ccc(C3COc4ccccc4O3)cc2)CC1] | 1-[4-(2,3-dihydro-1,4-benzodioxin-2-yl)benzyl]-4,4-dimethylpiperidine |
| 4 | 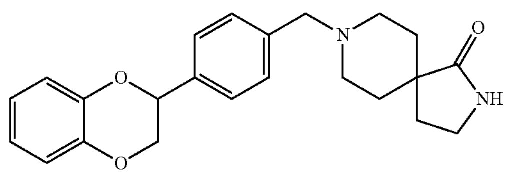 [SMILES: O=C1NCCC12CCN(Cc1ccc(C3COc4ccccc4O3)cc1)CC2] | 8-[4-(2,3-dihydro-1,4-benzodioxin-2-yl)benzyl]-2,8-diazaspiro[4.5]decan-1-one |
| 5 | 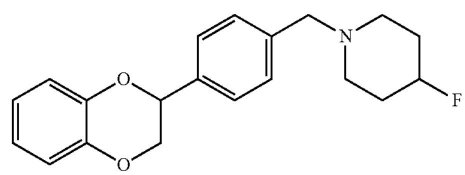 [SMILES: FC1CCN(Cc2ccc(C3COc4ccccc4O3)cc2)CC1] | 1-[4-(2,3-dihydro-1,4-benzodioxin-2-yl)benzyl]-4-fluoropiperidine |
| 6 | 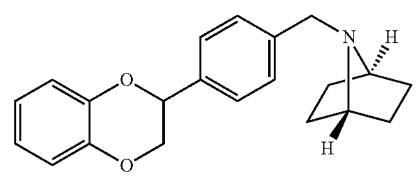 [SMILES: c1ccc2c(c1)OCC(c1ccc(CN3[C@H]4CC[C@@H]3CC4)cc1)O2] | (1s,4s)-7-[4-(2,3-dihydro-1,4-benzodioxin-2-yl)benzyl]-7-azabicyclo[2.2.1]heptane |
| 7 | 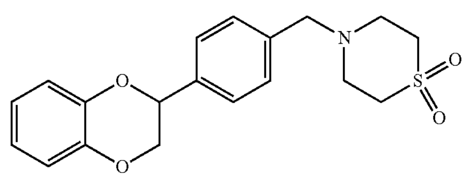 [SMILES: O=S1(=O)CCN(Cc2ccc(C3COc4ccccc4O3)cc2)CC1] | 4-[4-(2,3-dihydro-1,4-benzodioxin-2-yl)benzyl]thiomorpholine 1,1-dioxide |

TABLE 1-continued

Exemplary compounds of the invention.

| Cpd No. | Structure | Name |
| --- | --- | --- |
| 8 | 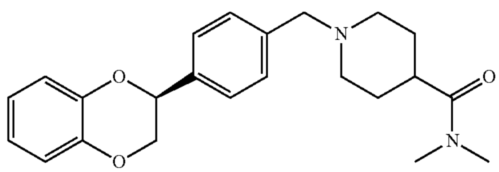 [SMILES: CN(C)C(=O)C1CCN(Cc2ccc([C@H]3COc4ccccc4O3)cc2)CC1] | 1-{4-[(2S)-2,3-dihydro-1,4-benzodioxin-2-yl]benzyl}-N,N-dimethylpiperidine-4-carboxamide |
| 9 | 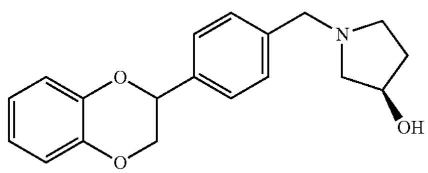 [SMILES: O[C@@H]1CCN(Cc2ccc(C3COc4ccccc4O3)cc2)C1] | (3S)-1-[4-(2,3-dihydro-1,4-benzodioxin-2-yl)benzyl]pyrrolidin-3-ol |
| 10 | 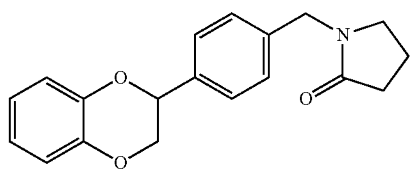 [SMILES: O=C1CCCN1Cc1ccc(C2COc3ccccc3O2)cc1] | 1-({1-[4-(2,3-dihydro-1,4-benzodioxin-2-yl)benzyl]piperidin-3-yl}methyl)pyrrolidin-2-one |
| 11 | 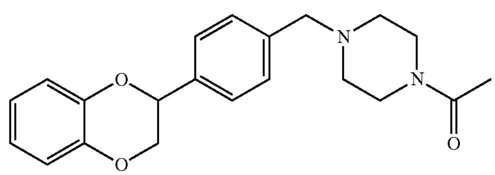 [SMILES: CC(=O)N1CCN(Cc2ccc(C3COc4ccccc4O3)cc2)CC1] | 1-{4-[4-(2,3-dihydro-1,4-benzodioxin-2-yl)benzyl]piperazin-1-yl}ethanone |
| 12 | 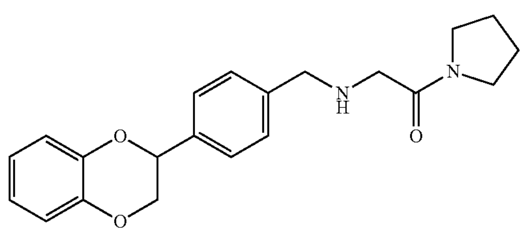 [SMILES: O=C(CNCc1ccc(C2COc3ccccc3O2)cc1)N1CCCC1] | 2-{[4-(2,3-dihydro-1,4-benzodioxin-2-yl)benzyl]amino}-1-(pyrrolidin-1-yl)ethanone |
| 13 | 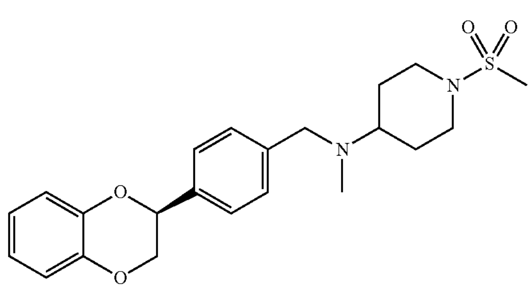 [SMILES: CN(Cc1ccc([C@H]2COc3ccccc3O2)cc1)C1CCN(S(C)(=O)=O)CC1] | N-{4-[(2S)-2,3-dihydro-1,4-benzodioxin-2-yl]benzyl}-N-methyl-1-(methylsulfonyl)piperidin-4-amine |
| 14 | 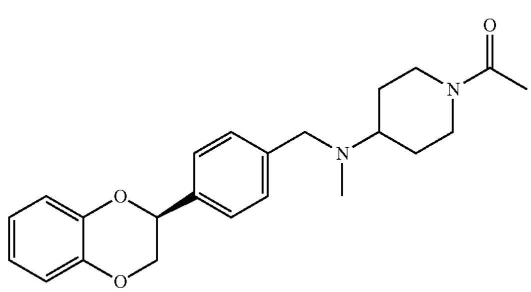 [SMILES: CC(=O)N1CCC(N(C)Cc2ccc([C@H]3COc4ccccc4O3)cc2)CC1] | 1-{4-[{4-[(2S)-2,3-dihydro-1,4-benzodioxin-2-yl]benzyl}(methyl)amino]piperidin-1-yl}ethanone |

TABLE 1-continued

Exemplary compounds of the invention.

| Cpd No. | Structure | Name |
|---|---|---|
| 15 | 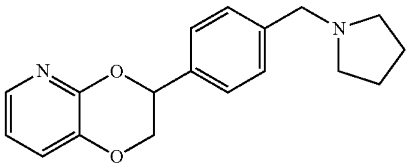 [SMILES: c1cnc2c(c1)OCC(c1ccc(CN3CCCC3)cc1)O2] | 3-[4-(pyrrolidin-1-ylmethyl)phenyl]-2,3-dihydro[1,4]dioxino[2,3-b]pyridine |
| 16 | 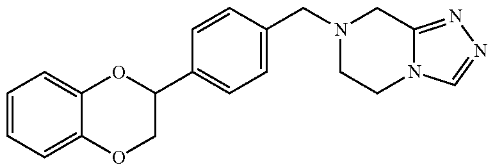 [SMILES: c1ccc2c(c1)OCC(c1ccc(CN3CCn4cnnc4C3)cc1)O2] | 7-[4-(2,3-dihydro-1,4-benzodioxin-2-yl)benzyl]-5,6,7,8-tetrahydro[1,2,4]triazolo[4,3-a]pyrazine |
| 17 | 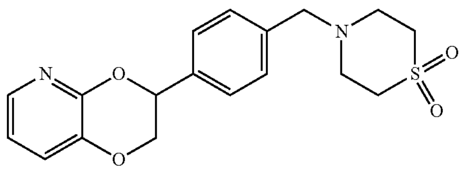 [SMILES: O=S1(=O)CCN(Cc2ccc(C3COc4cccnc4O3)cc2)CC1] | 3-{4-[(1,1-dioxidothiomorpholin-4-yl)methyl]phenyl}-2,3-dihydro[1,4]dioxino[2,3-b]pyridine |
| 18 | 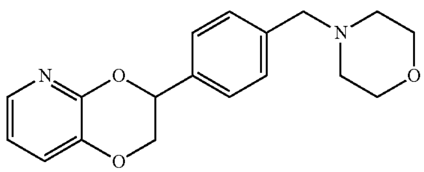 [SMILES: c1cnc2c(c1)OCC(c1ccc(CN3CCOCC3)cc1)O2] | 3-[4-(morpholin-4-ylmethyl)phenyl]-2,3-dihydro[1,4]dioxino[2,3-b]pyridine |
| 19 | 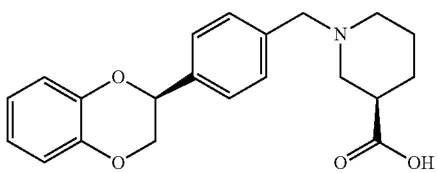 [SMILES: O=C(O)[C@@H]1CCCN(Cc2ccc([C@H]3COc4ccccc4O3)cc2)C1] | (3R)-1-{4-[(2S)-2,3-dihydro-1,4-benzodioxin-2-yl]benzyl}piperidine-3-carboxylic acid |
| 20 | 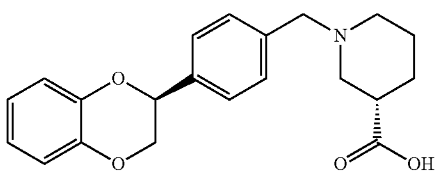 [SMILES: O=C(O)[C@H]1CCCN(Cc2ccc([C@H]3COc4ccccc4O3)cc2)C1] | (3S)-1-{4-[(2S)-2,3-dihydro-1,4-benzodioxin-2-yl]benzyl}piperidine-3-carboxylic acid |
| 21 | 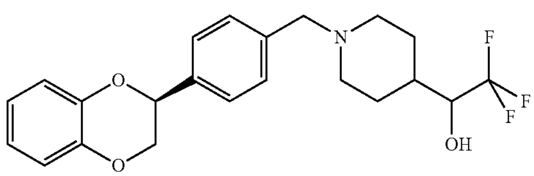 [SMILES: OC(C1CCN(Cc2ccc([C@H]3COc4ccccc4O3)cc2)CC1)C(F)(F)F] | 1-(1-{4-[(2S)-2,3-dihydro-1,4-benzodioxin-2-yl]benzyl}piperidin-4-yl)-2,2,2-trifluoroethanol |
| 22 | 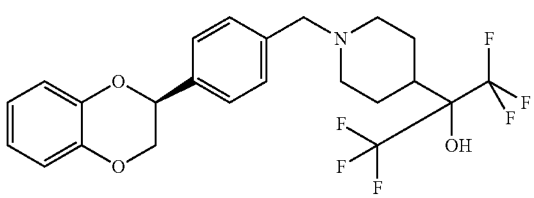 [SMILES: OC(CC(F)(F)F)(C1CCN(Cc2ccc([C@H]3COc4ccccc4O3)cc2)CC1)C(F)(F)F] | 2-(1-{4-[(2S)-2,3-dihydro-1,4-benzodioxin-2-yl]benzyl}piperidin-4-yl)-1,1,1,3,3,3-hexafluoropropan-2-ol |
| 23 | 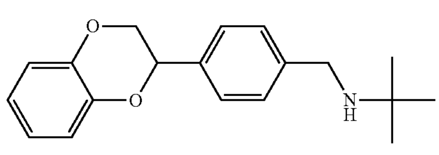 [SMILES: CC(C)(C)NCc1ccc(C2COc3ccccc3O2)cc1] | N-[4-(2,3-dihydro-1,4-benzodioxin-2-yl)benzyl]-2-methylpropan-2-amine |

TABLE 1-continued

Exemplary compounds of the invention.

| Cpd No. | Structure | Name |
|---|---|---|
| 24 | 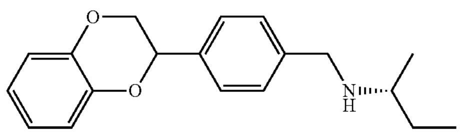 [SMILES: CC[C@@H](C)NCc1ccc(C2COc3ccccc3O2)cc1] | (2R)-N-[4-(2,3-dihydro-1,4-benzodioxin-2-yl)benzyl]butan-2-amine |
| 25 | 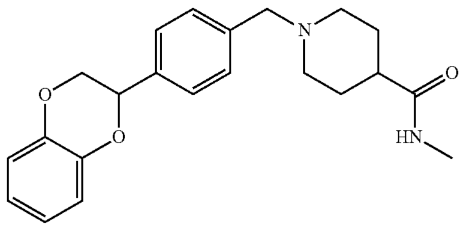 [SMILES: CNC(=O)C1CCN(Cc2ccc(C3COc4ccccc4O3)cc2)CC1] | 1-[4-(2,3-dihydro-1,4-benzodioxin-2-yl)benzyl]-N-methylpiperidine-4-carboxamide |
| 26 | 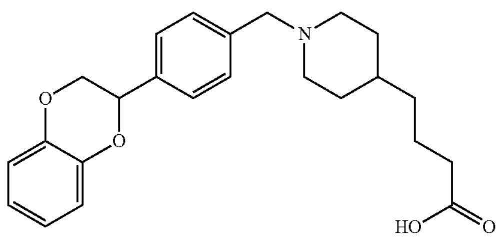 [SMILES: O=C(O)CCCC1CCN(Cc2ccc(C3COc4ccccc4O3)cc2)CC1] | 4-{1-[4-(2,3-dihydro-1,4-benzodioxin-2-yl)benzyl]piperidin-4-yl}butanoic acid |
| 27 | 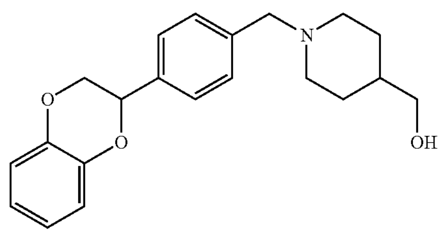 [SMILES: OCC1CCN(Cc2ccc(C3COc4ccccc4O3)cc2)CC1] | {1-[4-(2,3-dihydro-1,4-benzodioxin-2-yl)benzyl]piperidin-4-yl}methanol |
| 28 | 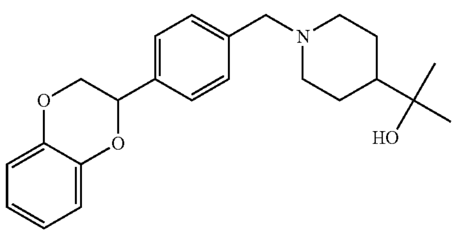 [SMILES: CC(C)(O)C1CCN(Cc2ccc(C3COc4ccccc4O3)cc2)CC1] | 2-{1-[4-(2,3-dihydro-1,4-benzodioxin-2-yl)benzyl]piperidin-4-yl}propan-2-ol |
| 29 | 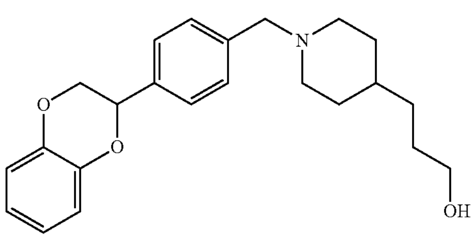 [SMILES: OCCCC1CCN(Cc2ccc(C3COc4ccccc4O3)cc2)CC1] | 3-{1-[4-(2,3-dihydro-1,4-benzodioxin-2-yl)benzyl]piperidin-4-yl}propan-1-ol |
| 30 | 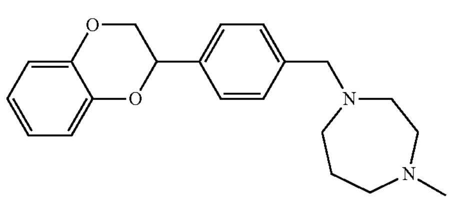 [SMILES: CN1CCCN(Cc2ccc(C3COc4ccccc4O3)cc2)CC1] | 1-[4-(2,3-dihydro-1,4-benzodioxin-2-yl)benzyl]-4-methyl-1,4-diazepan |

TABLE 1-continued

Exemplary compounds of the invention.

| Cpd No. | Structure | Name |
|---|---|---|
| 31 | 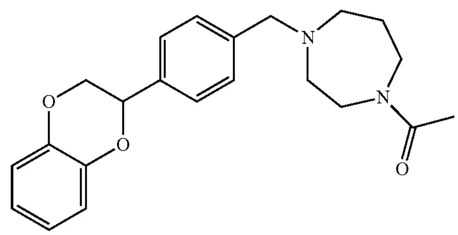 [SMILES: CC(=O)N1CCCN(Cc2ccc(C3COc4ccccc4O3)cc2)CC1] | 1-{4-[4-(2,3-ihydro-1,4-benzodioxin-2-yl)benzyl]-1,4-diazepan-1-yl]ethanone |
| 32 | 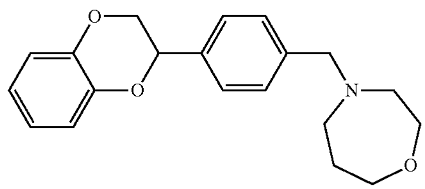 [SMILES: c1ccc2c(c1)OCC(c1ccc(CN3CCCOCC3)cc1)O2] | 4-[4-(2,3-dihydro-1,4-benzodioxin-2-yl)benzyl]-1,4-oxazepane |
| 33 | 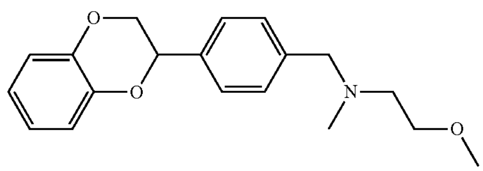 [SMILES: COCCN(C)Cc1ccc(C2COc3ccccc3O2)cc1] | N-[4-(2,3-dihydro-1,4-benzodioxin-2-yl)benzyl]-2-methoxy-N-methylethanamine |
| 34 | 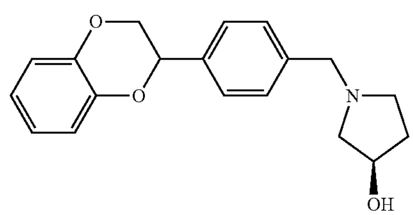 [SMILES: O[C@@H]1CCN(Cc2ccc(C3COc4ccccc4O3)cc2)C1] | (3R)-1-[4-(2,3-dihydro-1,4-benzodioxin-2-yl)benzyl]pyrrolidin-3-ol |
| 35 | 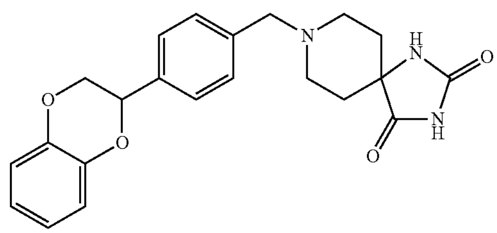 [SMILES: O=C1NC(=O)C2(CCN(Cc3ccc(C4COc5ccccc5O4)cc3)CC2)N1] | 8-[4-(2,3-dihydro-1,4-benzodioxin-2-yl)benzyl]-1,3,8-triazaspiro[4.5]decane-2,4-dione |
| 36 | 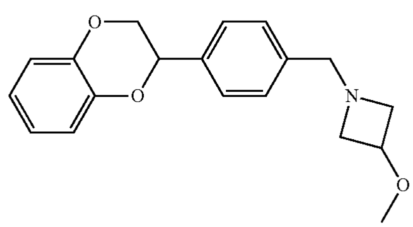 [SMILES: COC1CN(Cc2ccc(C3COc4ccccc4O3)cc2)C1] | 1-[4-(2,3-dihydro-1,4-benzodioxin-2-yl)benzyl]-3-methoxyazetidine |
| 37 | 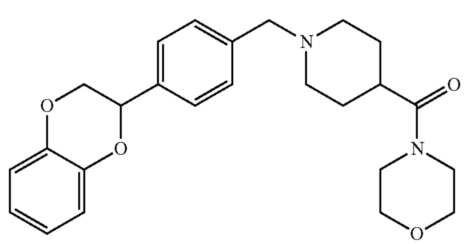 [SMILES: O=C(C1CCN(Cc2ccc(C3COc4ccccc4O3)cc2)CC1)N1CCOCC1] | {1-[4-(2,3-dihydro-1,4-benzodioxin-2-yl)benzyl]piperidin-4-yl}(morpholin-4-yl)methanone |

TABLE 1-continued

Exemplary compounds of the invention.

| Cpd No. | Structure | Name |
| --- | --- | --- |
| 38 | 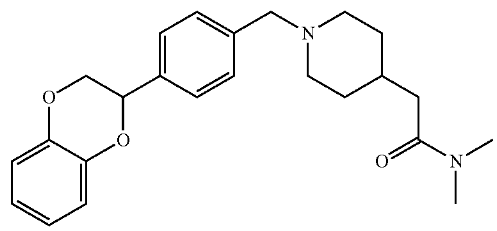 [SMILES: CN(C)C(=O)CC1CCN(Cc2ccc(C3COc4ccccc4O3)cc2)CC1] | 2-{1-[4-(2,3-dihydro-1,4-benzodioxin-2-yl)benzyl]piperidin-4-yl}-N,N-dimethylacetamide |
| 39 | 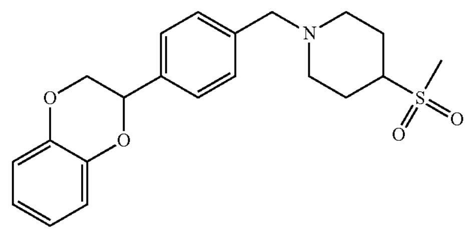 [SMILES: CS(=O)(=O)C1CCN(Cc2ccc(C3COc4ccccc4O3)cc2)CC1] | 1-[4-(2,3-dihydro-1,4-benzodioxin-2-yl)benzyl]-4-(methylsulfonyl)piperidine |
| 40 | 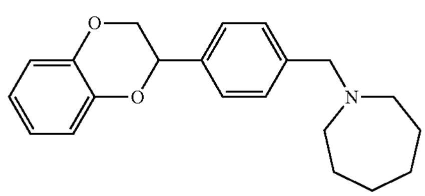 | 1-[4-(2,3-dihydro-1,4-benzodioxin-2-yl)benzyl]azepane |
| 41 | 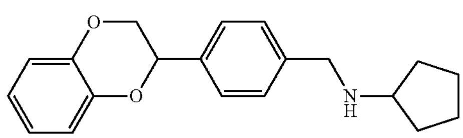 [SMILES: c1ccc2c(c1)OCC(c1ccc(CNC3CCCC3)cc1)O2] | N-[4-(2,3-dihydro-1,4-benzodioxin-2-yl)benzyl]cyclopentanamine |
| 42 | 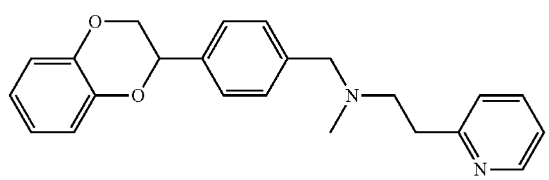 [SMILES: CN(CCc1ccccn1)Cc1ccc(C2COc3ccccc3O2)cc1] | N-[4-(2,3-dihydro-1,4-benzodioxin-2-yl)benzyl]-N-methyl-2-(pyridin-2-yl)ethanamine |
| 43 | 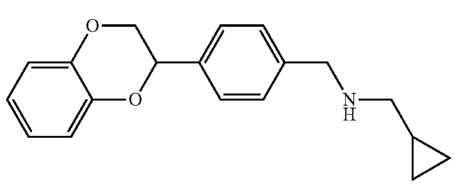 [SMILES: c1ccc2c(c1)OCC(c1ccc(CNCC3CC3)cc1)O2] | 1-cyclopropyl-N-[4-(2,3-dihydro-1,4-benzodioxin-2-yl)benzyl]methanamine |
| 44 | 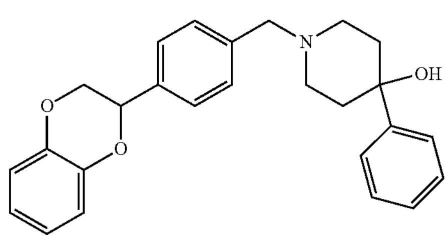 [SMILES: OC1(c2ccccc2)CCN(Cc2ccc(C3COc4ccccc4O3)cc2)CC1] | 1-[4-(2,3-dihydro-1,4-benzodioxin-2-yl)benzyl]-4-phenylpiperidin-4-ol |

TABLE 1-continued

Exemplary compounds of the invention.

| Cpd No. | Structure | Name |
|---|---|---|
| 45 | 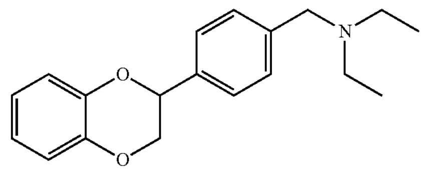 [SMILES: CCN(CC)Cc1ccc(C2COc3ccccc3O2)cc1] | N-[4-(2,3-dihydro-1,4-benzodioxin-2-yl)benzyl]-N-ethylethanamine |
| 46 | 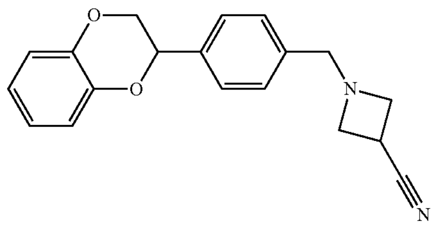 [SMILES: N#CC1CN(Cc2ccc(C3COc4ccccc4O3)cc2)C1] | 1-[4-(2,3-dihydro-1,4-benzodioxin-2-yl)benzyl]azetidine-3-carbonitrile |
| 47 | 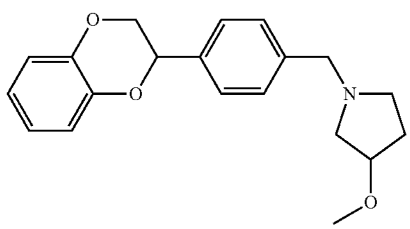 [SMILES: COC1CCN(Cc2ccc(C3COc4ccccc4O3)cc2)C1] | 1-[4-(2,3-dihydro-1,4-benzodioxin-2-yl)benzyl]-3-methoxypyrrolidine |
| 48 | 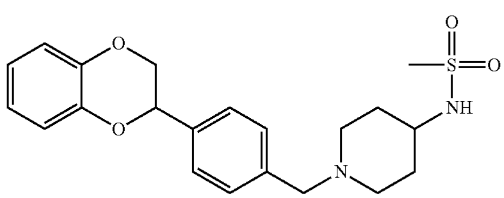 [SMILES: CS(=O)(=O)NC1CCN(Cc2ccc(C3COc4ccccc4O3)cc2)CC1] | N-{1-[4-(2,3-dihydro-1,4-benzodioxin-2-yl)benzyl]piperidin-4-yl}methanesulfonamide |
| 49 | 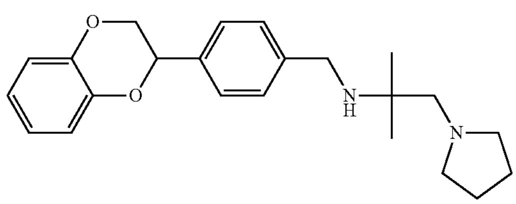 [SMILES: CC(C)(CN1CCCC1)NCc1ccc(C2COc3ccccc3O2)cc1] | N-[4-(2,3-dihydro-1,4-benzodioxin-2-yl)benzyl]-2-methyl-1-(pyrrolidin-1-yl)propan-2-amine |
| 50 | 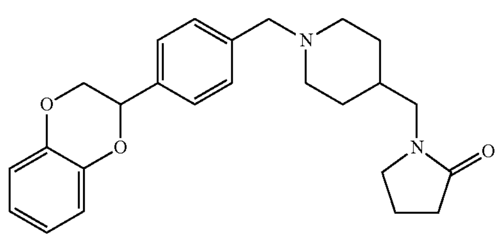 [SMILES: O=C1CCCN1CC1CCN(Cc2ccc(C3COc4ccccc4O3)cc2)CC1] | 1-({1-[4-(2,3-dihydro-1,4-benzodioxin-2-yl)benzyl]piperidin-4-yl}methyl)pyrrolidin-2-one |
| 51 | 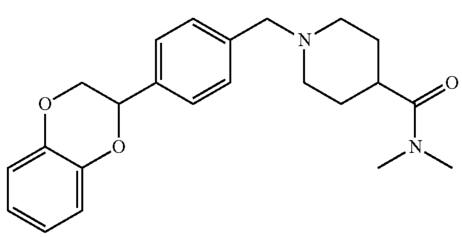 [SMILES: CN(C)C(=O)C1CCN(Cc2ccc(C3COc4ccccc4O3)cc2)CC1] | 1-[4-(2,3-dihydro-1,4-benzodioxin-2-yl)benzyl]-N,N-dimethylpiperidine-4-carboxamide |

TABLE 1-continued

Exemplary compounds of the invention.

| Cpd No. | Structure | Name |
|---|---|---|
| 52 | 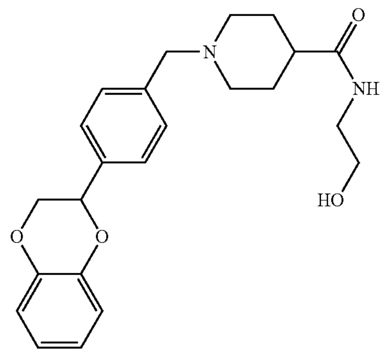 [SMILES: O=C(NCCO)C1CCN(Cc2ccc(C3COc4ccccc4O3)cc2)CC1] | 1-[4-(2,3-dihydro-1,4-benzodioxin-2-yl)benzyl]-N-(2-hydroxyethyl)piperidine-4-carboxamide |
| 53 | 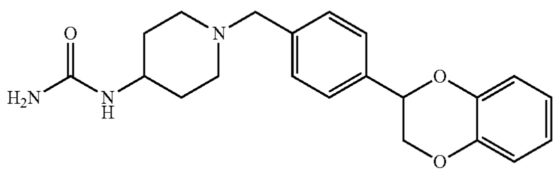 [SMILES: NC(=O)NC1CCN(Cc2ccc(C3COc4ccccc4O3)cc2)CC1] | 1-{1-[4-(2,3-dihydro-1,4-benzodioxin-2-yl)benzyl]piperidin-4-yl}urea |
| 54 | 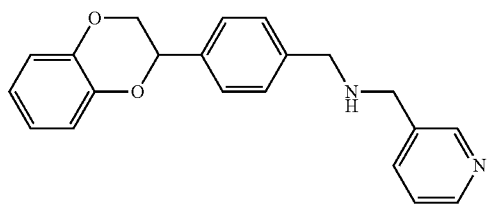 [SMILES: c1cncc(CNCc2ccc(C3COc4ccccc4O3)cc2)c1] | 1-[4-(2,3-dihydro-1,4-benzodioxin-2-yl)phenyl]-N-(pyridin-3-ylmethyl)methanamine |
| 55 | 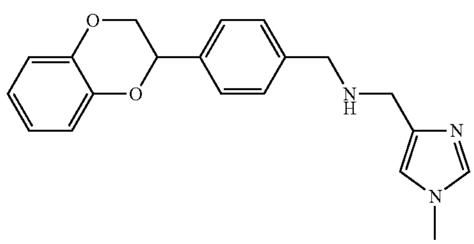 [SMILES: Cn1cnc(CNCc2ccc(C3COc4ccccc4O3)cc2)c1] | 1-[4-(2,3-dihydro-1,4-benzodioxin-2-yl)phenyl]-N-[(1-methyl-1H-imidazol-4-yl)methyl]methanamine |
| 56 | 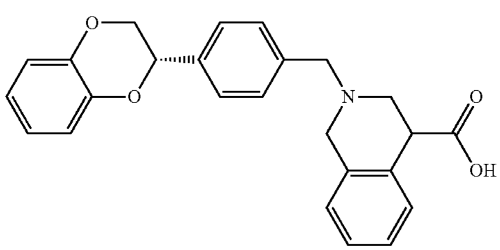 [SMILES: O=C(O)C1CN(Cc2ccc([C@H]3COc4ccccc4O3)cc2)Cc2ccccc21] | 2-{4-[(2S)-2,3-dihydro-1,4-benzodioxin-2-yl]benzyl}-1,2,3,4-tetrahydroisoquinoline-4-carboxylic acid |
| 57 | 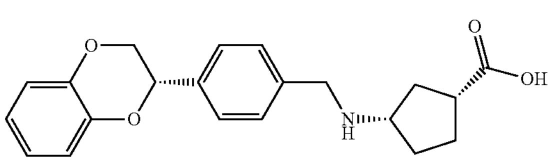 [SMILES: O=C(O)[C@@H]1CC[C@H](NCc2ccc([C@H]3COc4ccccc4O3)cc2)C1] | (1R,3S)-3-({4-[(2S)-2,3-dihydro-1,4-benzodioxin-2-yl]benzyl}amino)cyclopentanecarboxylic acid |
| 58 | 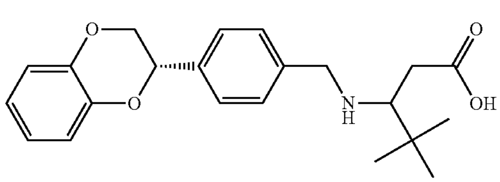 [SMILES: CC(C)(C)C(CC(=O)O)NCc1ccc([C@H]2COc3ccccc3O2)cc1] | 3-({4-[(2S)-2,3-dihydro-1,4-benzodioxin-2-yl]benzyl}amino)-4,4-dimethylpentanoic acid |

TABLE 1-continued

Exemplary compounds of the invention.

| Cpd No. | Structure | Name |
|---|---|---|
| 59 | 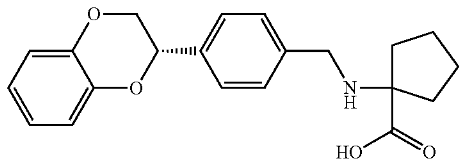 [SMILES: O=C(O)C1(NCc2ccc([C@H]3COc4ccccc4O3)cc2)CCCC1] | 1-({4-[(2S)-2,3-dihydro-1,4-benzodioxin-2-yl]benzyl}amino)cyclopentane-carboxylic acid |
| 60 | 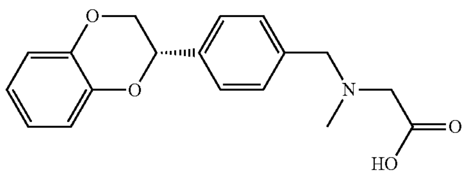 [SMILES: CN(CC(=O)O)Cc1ccc([C@H]2COc3ccccc3O2)cc1] | N-{4-[(2S)-2,3-dihydro-1,4-benzodioxin-2-yl]benzyl}-N-methylglycine |
| 61 | 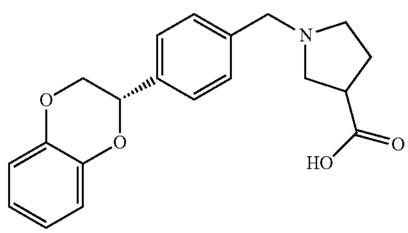 [SMILES: O=C(O)C1CCN(Cc2ccc([C@H]3COc4ccccc4O3)cc2)C1] | 1-{4-[(2S)-2,3-dihydro-1,4-benzodioxin-2-yl]benzyl}pyrrolidine-3-carboxylic acid |
| 62 | 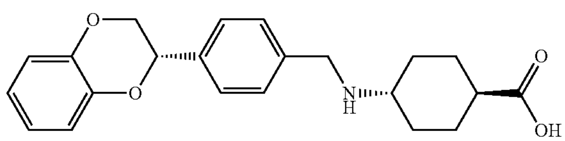 [SMILES: O=C(O)[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexane-carboxylic acid |
| 63 | 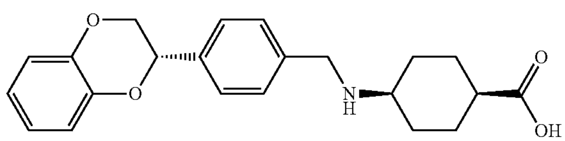 [SMILES: O=C(O)[C@H]1CC[C@@H](NCc2ccc([C@H]3COc4ccccc4O3)cc2)CC1] | cis-4-({4-[(2S)-2,3-dihydro-1,4-benzodioxin-2-yl]benzyl}amino)cyclohexane-carboxylic acid |
| 64 | 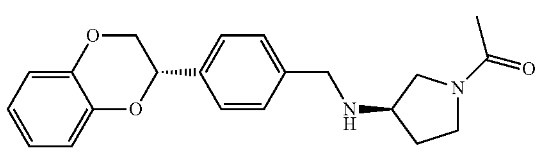 [SMILES: CC(=O)N1CC[C@@H](NCc2ccc([C@H]3COc4ccccc4O3)cc2)C1] | 1-[(3R)-3-({4-[(2S)-2,3-dihydro-1,4-benzodioxin-2-yl]benzyl}amino)pyrrolidin-1-yl]ethanone |
| 65 | 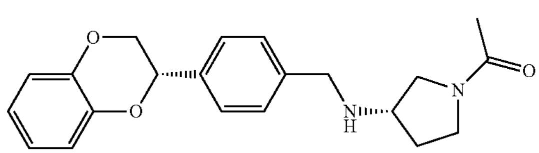 [SMILES: CC(=O)N1CC[C@H](NCc2ccc([C@H]3COc4ccccc4O3)cc2)C1] | 1-[(3S)-3-({4-[(2S)-2,3-dihydro-1,4-benzodioxin-2-yl]benzyl}amino)pyrrolidin-1-yl]ethanone |
| 66 | 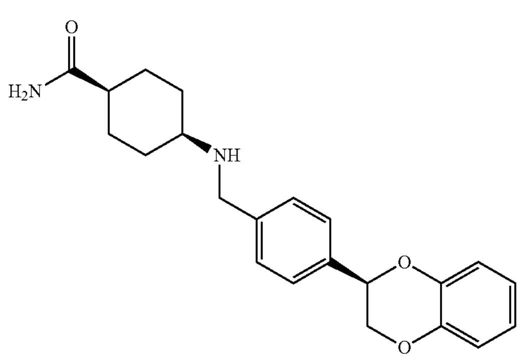 [SMILES: NC(=O)[C@H]1CC[C@@H](NCc2ccc([C@@H]3COc4ccccc4O3)cc2)CC1] | trans-4-({4-[(2S)-2,3-dihydro-1,4-benzodioxin-2-yl]benzyl}amino)cyclohexane-carboxamide |

TABLE 1-continued

Exemplary compounds of the invention.

| Cpd No. | Structure | Name |
|---|---|---|
| 67 | 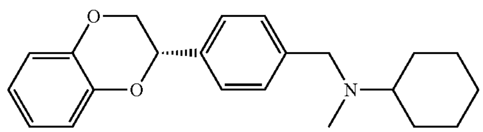 [SMILES: CN(Cc1ccc([C@H]2COc3ccccc3O2)cc1)C1CCCCC1] | N-{4-[(2S)-2,3-dihydro-1,4-benzodioxin-2-yl]benzyl}-N-methylcyclohexanamine |
| 68 | 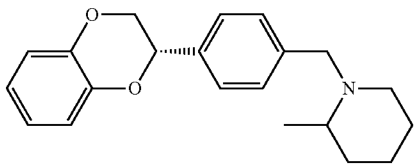 [SMILES: CC1CCCCN1Cc1ccc([C@H]2COc3ccccc3O2)cc1] | 1-{4-[[(2S)-2,3-dihydro-1,4-benzodioxin-2-yl]benzyl}-2-methylpiperidine |
| 69 | 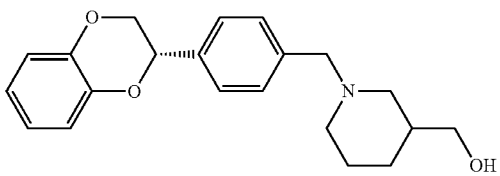 [SMILES: OCC1CCCN(Cc2ccc([C@H]3COc4ccccc4O3)cc2)C1] | (1-{4-[(2S)-2,3-dihydro-1,4-benzodioxin-2-yl]benzyl}piperidin-3-yl)methanol |
| 70 | 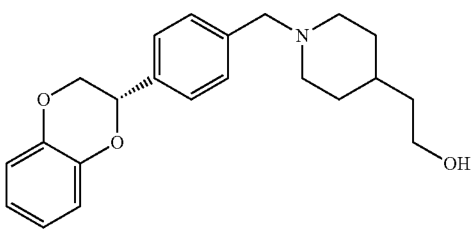 [SMILES: OCCC1CCN(Cc2ccc([C@H]3COc4ccccc4O3)cc2)CC1] | 2-(1-{4-[(2S)-2,3-dihydro-1,4-benzodioxin-2-yl]benzyl}piperidin-4-yl)ethanol |
| 71 | 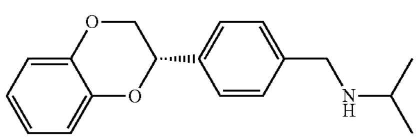 [SMILES: CC(C)NCc1ccc([C@H]2COc3ccccc3O2)cc1] | N-{4-[(2S)-2,3-dihydro-1,4-benzodioxin-2-yl]benzyl}propan-2-amine |
| 72 | 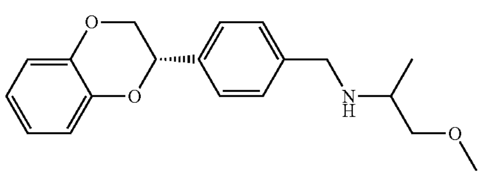 [SMILES: COCC(C)NCc1ccc([C@H]2COc3ccccc3O2)cc1] | N-{4-[(2S)-2,3-dihydro-1,4-benzodioxin-2-yl]benzyl}-1-methoxypropan-2-amine |
| 73 | 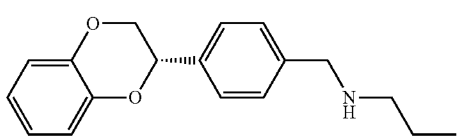 [SMILES: CCCNCc1ccc([C@H]2COc3ccccc3O2)cc1] | N-{4-[(2S)-2,3-dihydro-1,4-benzodioxin-2-yl]benzyl}propan-1-amine |
| 74 | 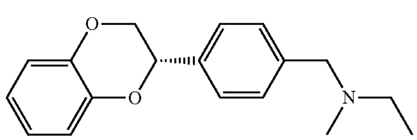 [SMILES: CCN(C)Cc1ccc([C@H]2COc3ccccc3O2)cc1] | N-{4-[(2S)-2,3-dihydro-1,4-benzodioxin-2-yl]benzyl}-N-methylethanamine |
| 75 | 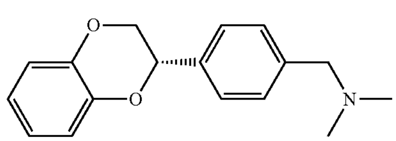 [SMILES: CN(C)Cc1ccc([C@H]2COc3ccccc3O2)cc1] | 1-{4-[(2S)-2,3-dihydro-1,4-benzodioxin-2-yl]phenyl}-N,N-dimethylmethanamine |

TABLE 1-continued

Exemplary compounds of the invention.

| Cpd No. | Structure | Name |
|---|---|---|
| 76 | 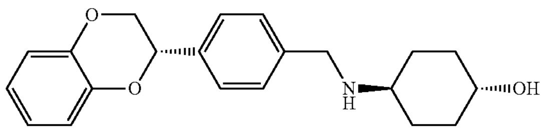 [SMILES: O[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexanol |
| 77 | 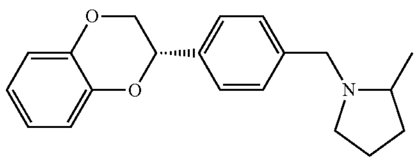 [SMILES: CC1CCCN1Cc1ccc([C@H]2COc3ccccc3O2)cc1] | 1-{4-[(2S)-2,3-dihydro-1,4-benzodioxin-2-yl]benzyl}-2-methylpyrrolidine |
| 78 | 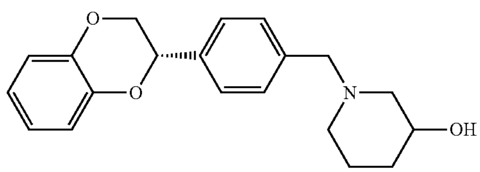 [SMILES: OC1CCCN(Cc2ccc([C@H]3COc4ccccc4O3)cc2)C1] | 1-{4-[(2S)-2,3-dihydro-1,4-benzodioxin-2-yl]benzyl}piperidin-3-ol |
| 79 | 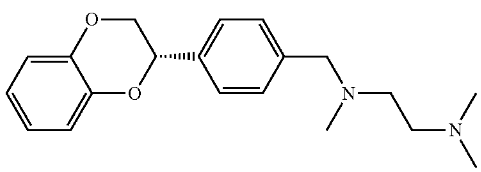 [SMILES: CN(C)CCN(C)Cc1ccc([C@H]2COc3ccccc3O2)cc1] | N-{4-[(2S)-2,3-dihydro-1,4-benzodioxin-2-yl]benzyl}-N,N',N'-trimethylethane-1,2-diamine |
| 80 | 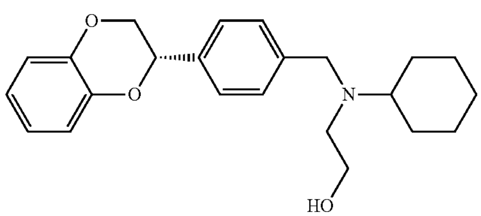 [SMILES: OCCN(Cc1ccc([C@H]2COc3ccccc3O2)cc1)C1CCCCC1] | 2-(cyclohexyl{4-[(2S)-2,3-dihydro-1,4-benzodioxin-2-yl]benzyl}amino)ethanol |
| 81 | 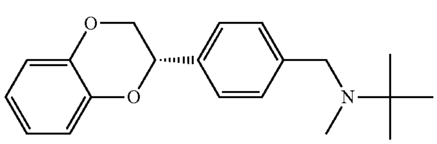 [SMILES: CN(Cc1ccc([C@H]2COc3ccccc3O2)cc1)C(C)(C)C] | N-{4-[(2S)-2,3-dihydro-1,4-benzodioxin-2-yl]benzyl}-N,2-dimethylpropan-2-amine |
| 82 | 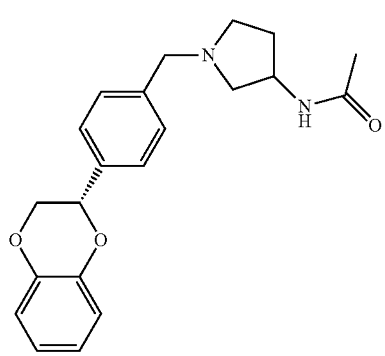 [SMILES: CC(=O)NC1CCN(Cc2ccc([C@H]3COc4ccccc4O3)cc2)C1] | N-(1-{4-[(2S)-2,3-dihydro-1,4-benzodioxin-2-yl]benzyl}pyrrolidin-3-yl)acetamide |

TABLE 1-continued

Exemplary compounds of the invention.

| Cpd No. | Structure | Name |
|---|---|---|
| 83 | 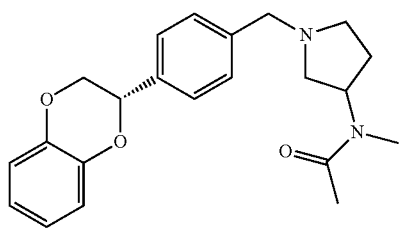 [SMILES: CC(=O)N(C)C1CCN(Cc2ccc([C@H]3COc4ccccc4O3)cc2)C1] | N-(1-{4-[(2S)-2,3-dihydro-1,4-benzodioxin-2-yl]benzyl}pyrrolidin-3-yl)-N-methylacetamide |
| 84 | 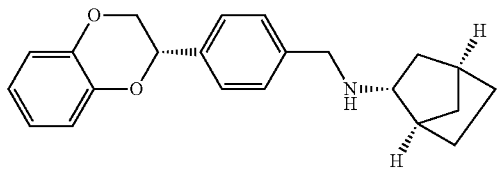 [SMILES: c1ccc2c(c1)OC[C@H](c1ccc(CN[C@@H]3C[C@H]4CC[C@@H]3C4)cc1)O2] | (1R,2R,4S)-N-{4-[(2S)-2,3-dihydro-1,4-benzodioxin-2-yl]benzyl}bicyclo[2.2.1]heptan-2-amine |
| 85 | 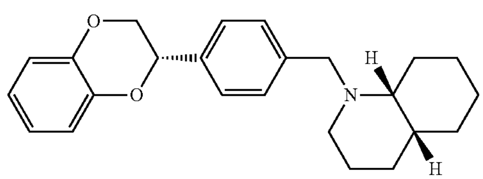 [SMILES: c1ccc2c(c1)OC[C@H](c1ccc(CN3CCC[C@H]4CCCC[C@H]43)cc1)O2] | (4aR,8aS)-1-{4-[(2S)-2,3-dihydro-1,4-benzodioxin-2-yl]benzyl}decahydroquinoline |
| 86 | 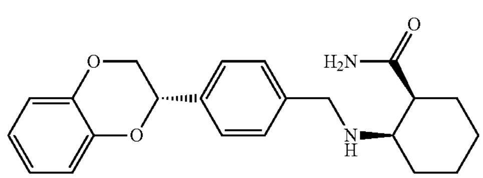 [SMILES: NC(=O)[C@H]1CCCC[C@H]1NCc1ccc([C@H]2COc3ccccc3O2)cc1] | (1S,2R)-2-({4-[(2S)-2,3-dihydro-1,4-benzodioxin-2-yl]benzyl}amino)cyclohexane-carboxamide |
| 87 | 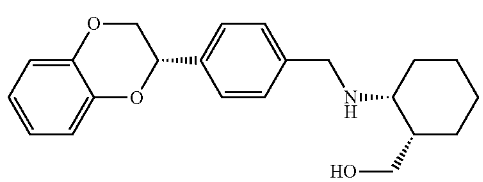 [SMILES: OC[C@H]1CCCC[C@H]1NCc1ccc([C@H]2COc3ccccc3O2)cc1] | [(1S,2R)-2-({4-[(2S)-2,3-dihydro-1,4-benzodioxin-2-yl]benzyl}amino)cyclohexyl]methanol |
| 88 | 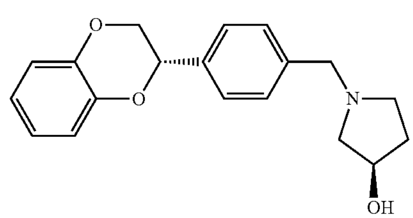 | (3R)-1-{4-[(2S)-2,3-dihydro-1,4-benzodioxin-2-yl]benzyl}pyrrolidin-3-ol |
| 89 | 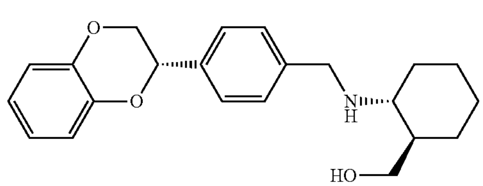 [SMILES: OC[C@@H]1CCCC[C@H]1NCc1ccc([C@H]2COc3ccccc3O2)cc1] | [(1R,2R)-2-({4-[(2S)-2,3-dihydro-1,4-benzodioxin-2-yl]benzyl}amino)cyclohexyl]methanol |

TABLE 1-continued

Exemplary compounds of the invention.

| Cpd No. | Structure | Name |
| --- | --- | --- |
| 90 | 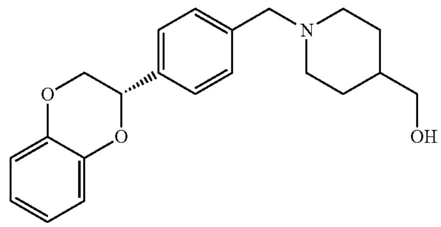 [SMILES: OCC1CCN(Cc2ccc([C@H]3COc4ccccc4O3)cc2)CC1] | (1-{4-[(2S)-2,3-dihydro-1,4-benzodioxin-2-yl]benzyl}piperidin-4-yl)methanol |
| 91 | 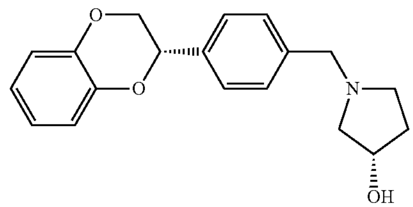 [SMILES: O[C@H]1CCN(Cc2ccc([C@H]3COc4ccccc4O3)cc2)C1] | (3S)-1-{4-[(2S)-2,3-dihydro-1,4-benzodioxin-2-yl]benzyl}pyrrolidin-3-ol |
| 92 | 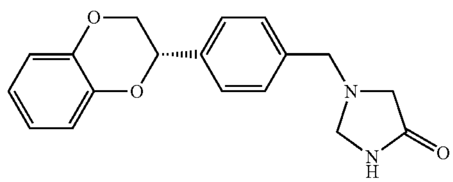 [SMILES: O=C1CN(Cc2ccc([C@H]3COc4ccccc4O3)cc2)CN1] | 1-{4-[(2S)-2,3-dihydro-1,4-benzodioxin-2-yl]benzyl}imidazolidin-4-one |
| 93 | 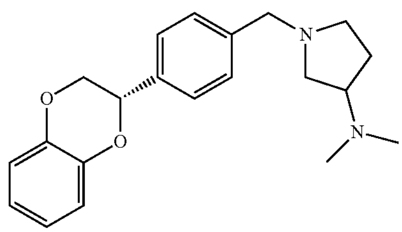 [SMILES: CN(C)C1CCN(Cc2ccc([C@H]3COc4ccccc4O3)cc2)C1] | 1-{4-[(2S)-2,3-dihydro-1,4-benzodioxin-2-yl]benzyl}-N,N-dimethylpyrrolidin-3-amine |
| 94 | 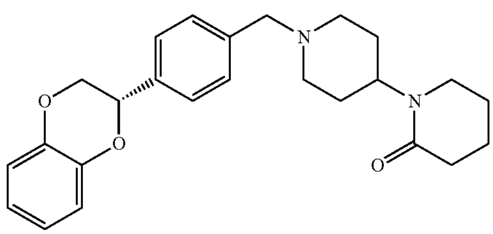 [SMILES: O=C1CCCCN1C1CCN(Cc2ccc([C@H]3COc4ccccc4O3)cc2)CC1] | 1'-{4-[(2S)-2,3-dihydro-1,4-benzodioxin-2-yl]benzyl}-1,4'-bipiperidin-2-one |
| 95 | 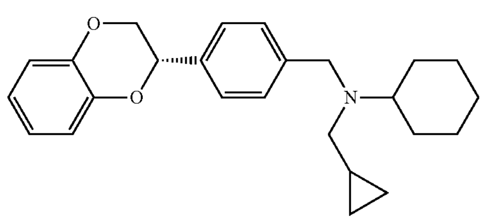 [SMILES: c1ccc2c(c1)OC[C@H](c1ccc(CN(CC3CC3)C3CCCCC3)cc1)O2] | N-(cyclopropylmethyl)-N-(4-[(2S)-2,3-dihydro-1,4-benzodioxin-2-yl]benzyl}cyclohexanamine |
| 96 | 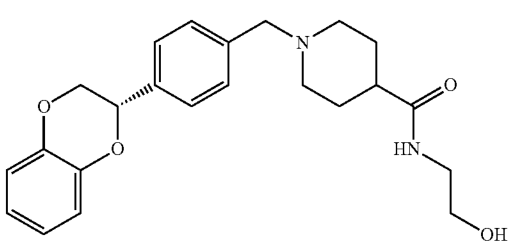 [SMILES: O=C(NCCO)C1CCN(Cc2ccc([C@H]3COc4ccccc4O3)cc2)CC1] | 1-{4-[(2S)-2,3-dihydro-1,4-benzodioxin-2-yl]benzyl}-N-(2-hydroxyethyl)piperidine-4-carboxamide |

TABLE 1-continued

Exemplary compounds of the invention.

| Cpd No. | Structure | Name |
| --- | --- | --- |
| 97 | 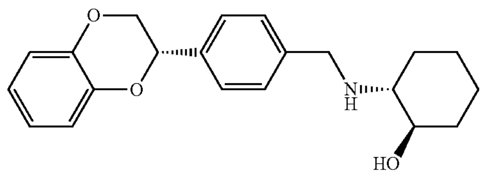 [SMILES: O[C@@H]1CCCC[C@H]1NCc1ccc([C@H]2COc3ccccc3O2)cc1] | (1R,2R)-2-({4-[(2S)-2,3-dihydro-1,4-benzodioxin-2-yl]benzyl}amino)cyclohexanol |
| 98 | 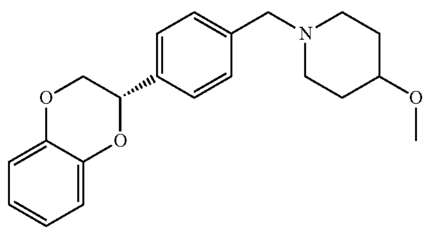 [SMILES: COC1CCN(Cc2ccc([C@H]3COc4ccccc4O3)cc2)CC1] | 1-{4-[(2S)-2,3-dihydro-1,4-benzodioxin-2-yl]benzyl}-4-methoxypiperidine |
| 99 | 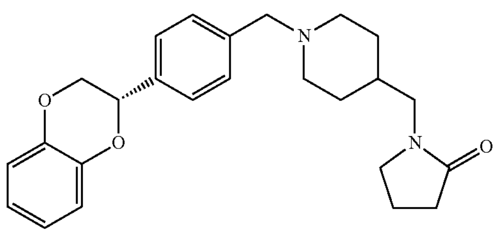 | 1-[(1-{4-[(2S)-2,3-dihydro-1,4-benzodioxin-2-yl]benzyl}piperidin-4-yl)methyl]pyrrolidin-2-one |
| 100 | 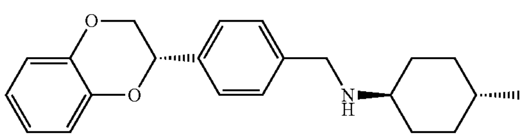 [SMILES: C[C@H]1CC[C@H](NCc2ccc([C@H]3COc4ccccc4O3)cc2)CC1] | trans-N-{4-[(2S)-2,3-dihydro-1,4-benzodioxin-2-yl]benzyl}-4-methylcyclohexanamine |
| 101 | 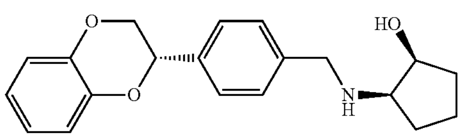 [SMILES: O[C@H]1CCC[C@H]1NCc1ccc([C@H]2COc3ccccc3O2)cc1] | (1S,2R)-2-({4-[(2S)-2,3-dihydro-1,4-benzodioxin-2-yl]benzyl}amino)cyclopentanol |
| 102 | 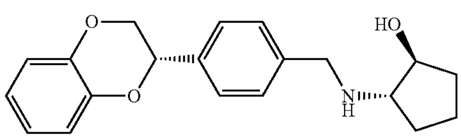 [SMILES: O[C@H]1CCC[C@@H]1NCc1ccc([C@H]2COc3ccccc3O2)cc1] | (1S,2S)-2-({4-[(2S)-2,3-dihydro-1,4-benzodioxin-2-yl]benzyl}amino)cyclopentanol |
| 103 | 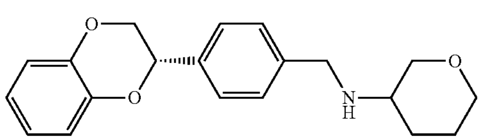 [SMILES: c1ccc2c(c1)OC[C@H](c1ccc(CNC3CCCOC3)cc1)O2] | N-{4-[(2S)-2,3-dihydro-1,4-benzodioxin-2-yl]benzyl}tetrahydro-2H-pyran-3-amine |
| 104 | 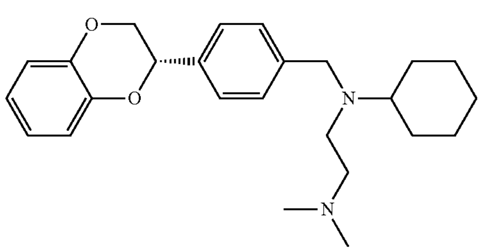 [SMILES: CN(C)CCN(Cc1ccc([C@H]2COc3ccccc3O2)cc1)C1CCCCC1] | N-cyclohexyl-N-{4-[(2S)-2,3-dihydro-1,4-benzodioxin-2-yl]benzyl}-N',N'-dimethylethane-1,2-diamine |

TABLE 1-continued

Exemplary compounds of the invention.

| Cpd No. | Structure | Name |
|---|---|---|
| 105 | 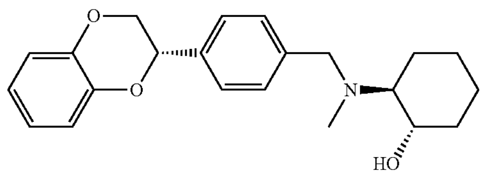 [SMILES: CN(Cc1ccc([C@H]2COc3ccccc3O2)cc1)[C@H]1CCCC[C@@H]1O] | (1S,2S)-2-[{4-[(2S)-2,3-dihydro-1,4-benzodioxin-2-yl]benzyl}(methyl)amino]cyclohexanol |
| 106 | 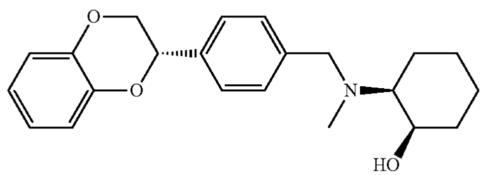 [SMILES: CN(Cc1ccc([C@H]2COc3ccccc3O2)cc1)[C@H]1CCCC[C@H]1O] | (1R,2S)-2-[{4-[(2S)-2,3-dihydro-1,4-benzodioxin-2-yl]benzyl}(methyl)amino]cyclohexanol |
| 107 | 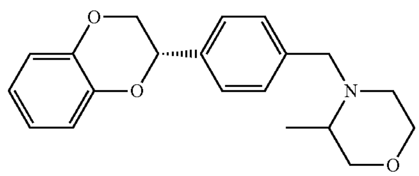 [SMILES: CC1COCCN1Cc1ccc([C@H]2COc3ccccc3O2)cc1] | 4-{4-[(2S)-2,3-dihydro-1,4-benzodioxin-2-yl]benzyl}-3-methylmorpholine |
| 108 | 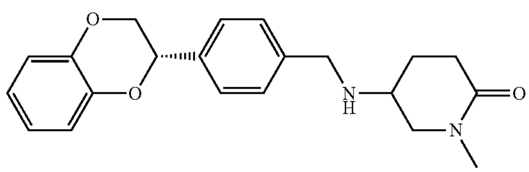 [SMILES: CN1CC(NCc2ccc([C@H]3COc4ccccc4O3)cc2)CCC1=O] | 5-({4-[(2S)-2,3-dihydro-1,4-benzodioxin-2-yl]benzyl}amino)-1-methylpiperidin-2-one |
| 109 | 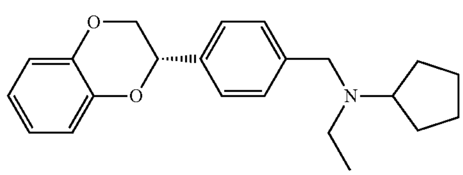 [SMILES: CCN(Cc1ccc([C@H]2COc3ccccc3O2)cc1)C1CCCC1] | N-{4-[(2S)-2,3-dihydro-1,4-benzodioxin-2-yl]benzyl}-N-ethylcyclopentanamine |
| 110 | 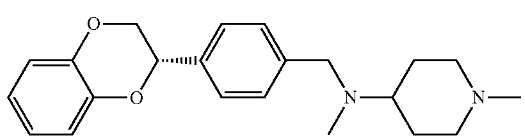 [SMILES: CN1CCC(N(C)Cc2ccc([C@H]3COc4ccccc4O3)cc2)CC1] | N-{4-[(2S)-2,3-dihydro-1,4-benzodioxin-2-yl]benzyl}-N,1-dimethylpiperidin-4-amine |
| 111 | 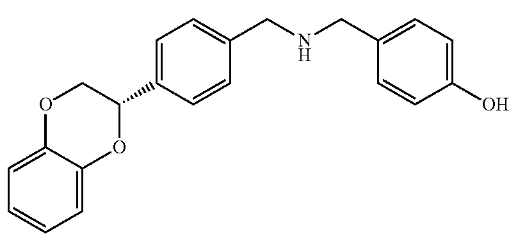 [SMILES: Oc1ccc(CNCc2ccc([C@H]3COc4ccccc4O3)cc2)cc1] | 4-[({4-[(2S)-2,3-dihydro-1,4-benzodioxin-2-yl]benzyl}amino)methyl]phenol |
| 112 | 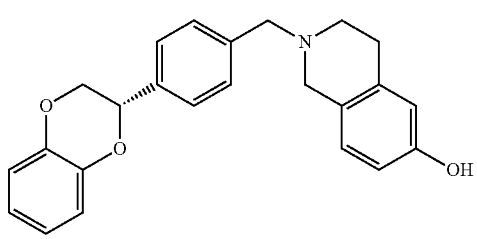 [SMILES: Oc1ccc2c(c1)CCN(Cc1ccc([C@H]3COc4ccccc4O3)cc1)C2] | 2-{4-[(2S)-2,3-dihydro-1,4-benzodioxin-2-yl]benzyl}-1,2,3,4-tetrahydroisoquinolin-6-ol |

TABLE 1-continued

Exemplary compounds of the invention.

| Cpd No. | Structure | Name |
|---|---|---|
| 113 | 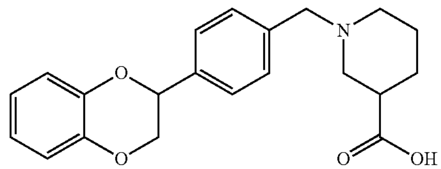 [SMILES: O=C(O)C1CCCN(Cc2ccc(C3COc4ccccc4O3)cc2)C1] | 1-[4-(2,3-dihydro-1,4-benzodioxin-2-yl)benzyl]piperidine-3-carboylic acid |
| 114 | 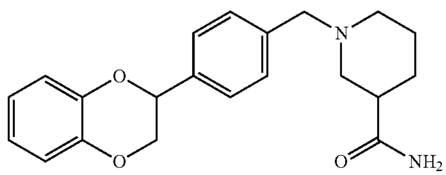 [SMILES: NC(=O)C1CCCN(Cc2ccc(C3COc4ccccc4O3)cc2)C1] | 1-[4-(2,3-dihydro-1,4-benzodioxin-2-yl)benzyl]piperidin-3-carboxamide |
| 115 | 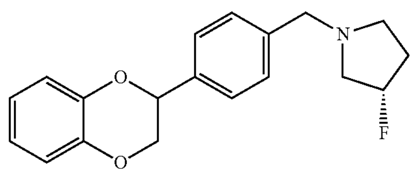 [SMILES: F[C@H]1CCN(Cc2ccc(C3COc4ccccc4O3)cc2)C1] | (3S)-1-[4-(2,3-dihydro-1,4-benzodioxin-2-yl)benzyl]-3-fluoropyrrolidine |
| 116 | 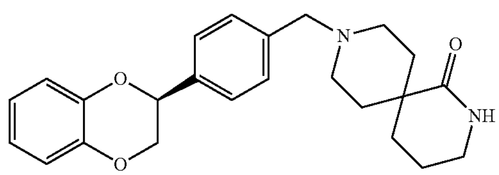 [SMILES: O=C1NCCCC12CCN(Cc1ccc([C@H]3COc4ccccc4O3)cc1)CC2] | 9-{4-[(2S)-2,3-dihydro-1,4-benzodioxin-2-yl]benzyl}-2,9-diazaspiro[5.5]undecan-1-one |
| 117 | 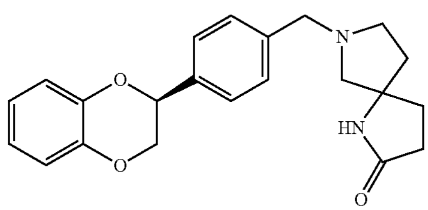 [SMILES: O=C1CCC2(CCN(Cc3ccc([C@H]4COc5ccccc5O4)cc3)C2)N1] | 7-{4-[(2S)-2,3-dihydro-1,4-benzodioxin-2-yl]benzyl}-1,7-diazaspiro[4.4]nonan-2-one |
| 118 | 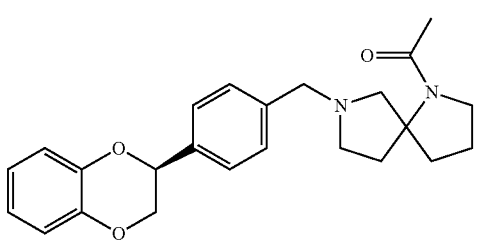 [SMILES: CC(=O)N1CCCC12CCN(Cc1ccc([C@H]3COc4ccccc4O3)cc1)C2] | 1-(7-{4-[(2S)-2,3-dihydro-1,4-benzodioxin-2-yl]benzyl}-1,7-diazaspiro[4.4]non-1-yl)ethanone |
| 119 | 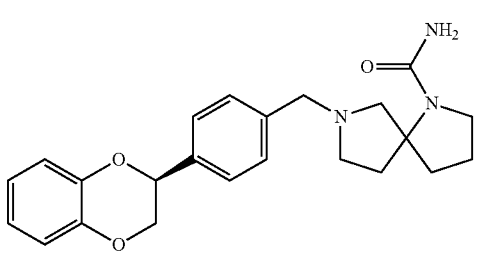 [SMILES: NC(=O)N1CCCC12CCN(Cc1ccc([C@H]3COc4ccccc4O3)cc1)C2] | 7-{4-[(2S)-2,3-dihydro-1,4-benzodioxin-2-yl]benzyl}-1,7-diazaspiro[4.4]nonane-1-carboxamide |

TABLE 1-continued

Exemplary compounds of the invention.

| Cpd No. | Structure | Name |
| --- | --- | --- |
| 120 | 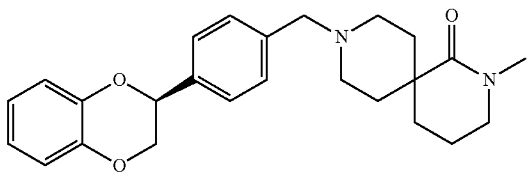 [SMILES: CN1CCCC2(CCN(Cc3ccc([C@H]4COc5ccccc5O4)cc3)CC2)C1=O] | 9-{4-[(2S)-dihydro-1,4-benzodioxin-2-yl]benzyl}-2-methyl-2,9-diazaspiro[5.5]undecan-1-one |
| 121 | 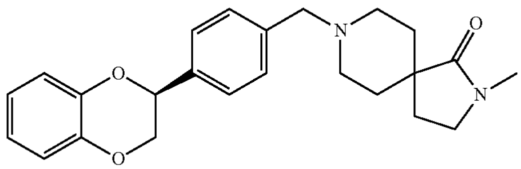 [SMILES: CN1CCC2(CCN(Cc3ccc([C@H]4COc5ccccc5O4)cc3)CC2)C1=O] | 8-{4-[(2S)-2,3-dihydro-1,4-benzodioxin-2-yl]benzyl}-2-methyl-2,8-diazaspiro[4.5]decan-1-one |
| 122 | 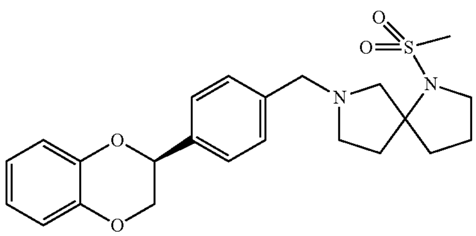 [SMILES: CS(=O)(=O)N1CCCC12CCN(Cc1ccc([C@H]3COc4ccccc4O3)cc1)C2] | 7-{4-[(2S)-2,3-dihydro-1,4-benzodioxin-2-yl]benzyl}-1-(methylsulfonyl)-1,7-diazaspiro[4.4]nonane |
| 123 | 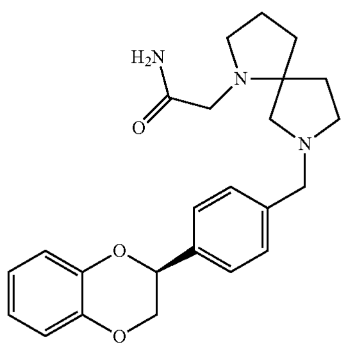 [SMILES: NC(=O)CN1CCCC12CCN(Cc1ccc([C@H]3COc4ccccc4O3)cc1)C2] | 2-(7-{4-[(2S)-2,3-dihydro-1,4-benzodioxin-2-yl]benzyl}-1,7-diazaspiro[4.4]non-1-yl)acetamide |
| 124 | 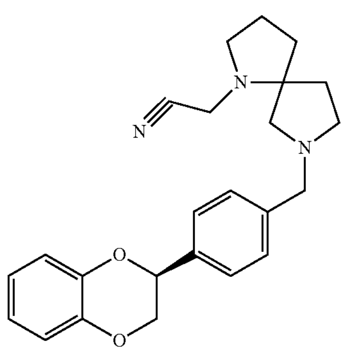 [SMILES: N#CCN1CCCC12CCN(Cc1ccc([C@H]3COc4ccccc4O3)cc1)C2] | (7-{4-[(2S)-2,3-dihydro-1,4-benzodioxin-2-yl]benzyl}-1,7-diazaspiro[4.4]non-1-yl)acetaonitrile |
| 125 | 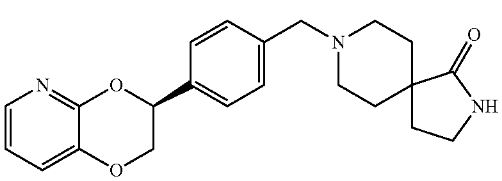 [SMILES: O=C1NCCC12CCN(Cc1ccc([C@H]3COc4cccnc4O3)cc1)CC2] | 8-{4-[(3S)-2,3-dihydro[1,4]dioxino[2,3-b]pyridin-3-yl]benzyl}-2,8-diazaspiro[4.5]decan-1-one |

TABLE 1-continued

Exemplary compounds of the invention.

| Cpd No. | Structure | Name |
| --- | --- | --- |
| 126 | 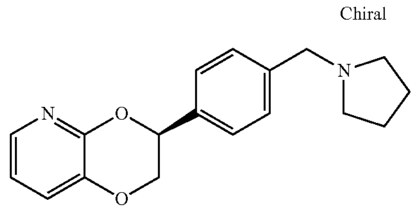 [SMILES: c1cnc2c(c1)OC[C@H](c1ccc(CN3CCCC3)cc1)O2] | (3S)-3-[4-(pyrrolidin-1-ylmethyl)phenyl]-2,3-dihydro[1,4]dioxino[2,3-b]pyridine |
| 127 | 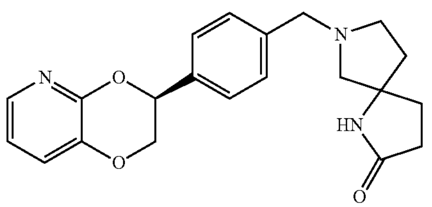 [SMILES: O=C1CCC2(CCN(Cc3ccc([C@H]4COc5cccnc5O4)cc3)C2)N1] | 7-{4-[(3S)-2,3-dihydro[1,4]dioxino[2,3-b]pyridin-3-yl]benzyl}-1,7-diazaspiro[4.4]nonan-2-one |
| 128 | 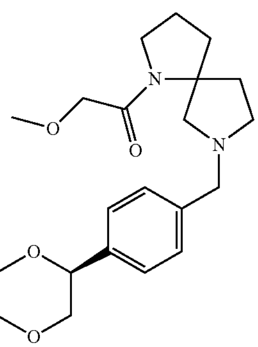 | 1-(7-{4-[(2S)-2,3-dihydro-1,4-benzodioxin-2-yl]benzyl}-1,7-diazaspiro[4.4]non-1-yl)-2-methoxyethanone |
| 129 | 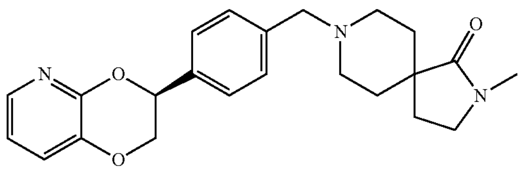 [SMILES: CN1CCC2(CCN(Cc3ccc([C@H]4COc5cccnc5O4)cc3)CC2)C1=O] | 8-{4-[(3S)-2,3-dihydro[1,4]dioxino[2,3-b]pyridin-3-yl]benzyl}-2-methyl-2,8-diazaspiro[4.5]decan-1-one |
| 130 | 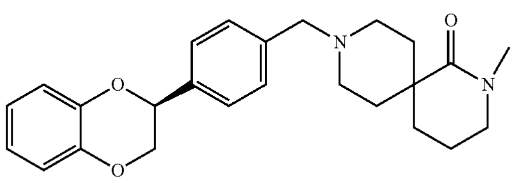 [SMILES: CN1CCCC2(CCN(Cc3ccc([C@H]4COc5ccccc5O4)cc3)CC2)C1=O] | 9-[(S)-4-(2,3-Dihydro-benzo[1,4]dioxin-2-yl)-benzyl]-2-methyl-2,9-diaza-spiro[5.5]undecan-1-one |
| 131 | 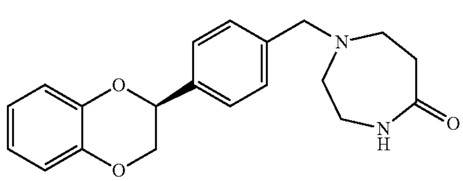 [SMILES: O=C1CCN(Cc2ccc([C@H]3COc4ccccc4O3)cc2)CCN1] | 1-{4-[(2S)-2,3-dihydro-1,4-benzodioxin-2-yl]benzyl}-1,4-diazepan-5-one |
| 132 | 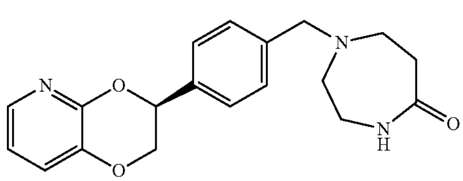 [SMILES: O=C1CCN(Cc2ccc([C@H]3COc4cccnc4O3)cc2)CCN1] | 1-{4-[(3S)-2,3-dihydro[1,4]dioxino[2,3-b]pyridin-3-yl]benzyl}-1,4-diazepan-5-one |

TABLE 1-continued

Exemplary compounds of the invention.

| Cpd No. | Structure | Name |
| --- | --- | --- |
| 133 | 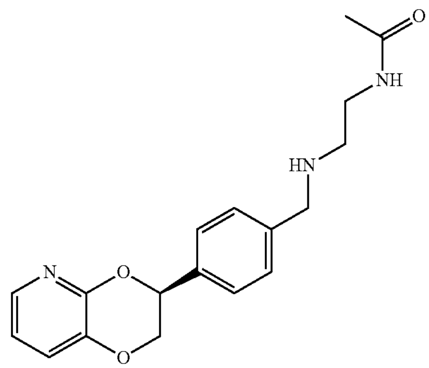 [SMILES: CC(=O)NCCNCc1ccc([C@H]2COc3cccnc3O2)cc1] | N-[2-({4-[(3S)-2,3-dihydro[1,4]dioxino[2,3-b]pyridin-3-yl]benzyl}amino)ethyl]acetamide |
| 134 | 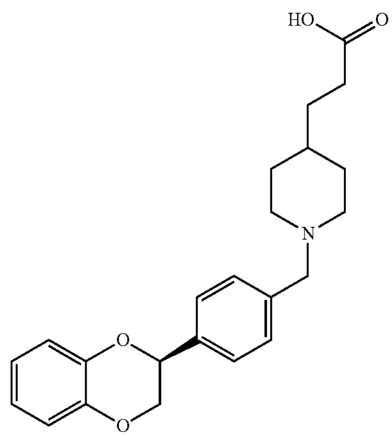 [SMILES: O=C(O)CCC1CCN(Cc2ccc([C@H]3COc4ccccc4O3)cc2)CC1] | 3-(1-{4-[(2S)-2,3-dihydro-1,4-benzodioxin-2-yl]benzyl}piperidin-4-yl)propanoic acid |
| 135 | 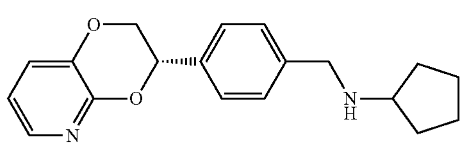 [SMILES: c1cnc2c(c1)OC[C@H](c1ccc(CNC3CCCC3)cc1)O2] | N-{4-[(3S)-2,3-dihydro[1,4]dioxino[2,3-b]pyridin-3-yl]benzyl}cyclopentanamine |
| 136 | 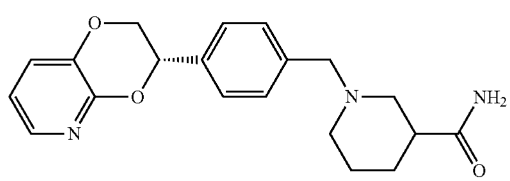 [SMILES: NC(=O)C1CCCN(Cc2ccc([C@H]3COc4cccnc4O3)cc2)C1] | 1-{4-[(3S)-2,3-dihydro[1,4]dioxino[2,3-b]pyridin-3-yl]benzyl}piperidine-3-carboxamide |
| 137 | 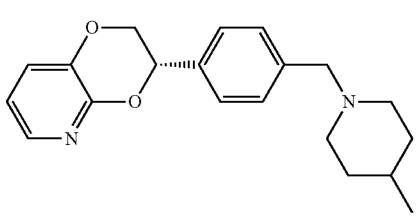 [SMILES: CC1CCN(Cc2ccc([C@H]3COc4cccnc4O3)cc2)CC1] | (3S)-3-{4-[(4-methylpiperidin-1-yl)methyl]phenyl}-2,3-dihydro[1,4]dioxino[2,3-b]pyridine |
| 138 | 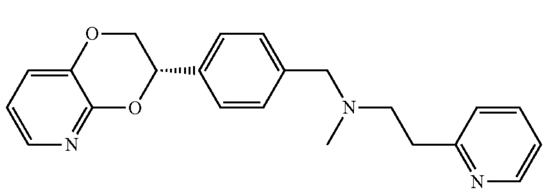 [SMILES: CN(CCc1ccccn1)Cc1ccc([C@H]2COc3cccnc3O2)cc1] | N-{4-[(3S)-2,3-dihydro[1,4]dioxino[2,3-b]pyridin-3-yl]benzyl}-N-methyl-2-(pyridin-2-yl)ethanamine |

TABLE 1-continued

Exemplary compounds of the invention.

| Cpd No. | Structure | Name |
|---|---|---|
| 139 | 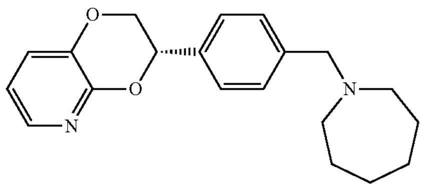 [SMILES: c1cnc2c(c1)OC[C@H](c1ccc(CN3CCCCCC3)cc1)O2] | (3S)-3-[4-(azepan-1-ylmethyl)phenyl]-2,3-dihydro[1,4]dioxino[2,3-b]pyridine |
| 140 | 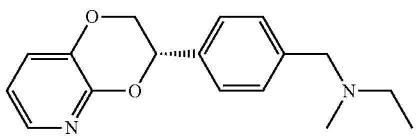 [SMILES: CCN(C)Cc1ccc([C@H]2COc3cccnc3O2)cc1] | N-{4-[(3S)-2,3-dihydro[1,4]dioxino[2,3-b]pyridin-3-yl]benzyl}-N-methylethanamine |
| 141 | 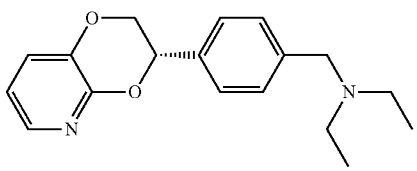 [SMILES: CCN(CC)Cc1ccc([C@H]2COc3cccnc3O2)cc1] | N-{4-[(3S)-2,3-dihydro[1,4]dioxino[2,3-b]pyridin-3-yl]benzyl}-N-ethylethanamine |
| 142 | 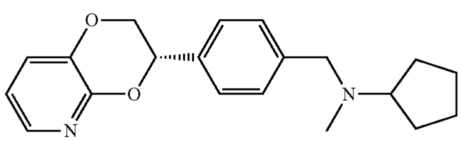 [SMILES: CN(Cc1ccc([C@H]2COc3cccnc3O2)cc1)C1CCCC1] | N-{4-[(3S)-2,3-dihydro[1,4]dioxino[2,3-b]pyridin-3-yl]benzyl}-N-methylcyclopentanamine |
| 143 | 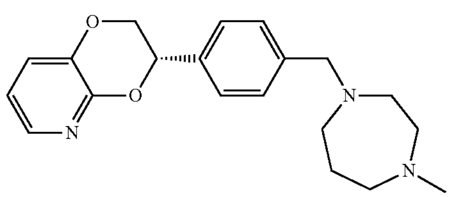 [SMILES: CN1CCCN(Cc2ccc([C@H]3COc4cccnc4O3)cc2)CC1] | (3S)-3-{4-[(4-methyl-1,4-diazepan-1-yl)methyl]phenyl}-2,3-dihydro[1,4]dioxino[2,3-b]pyridine |
| 144 | 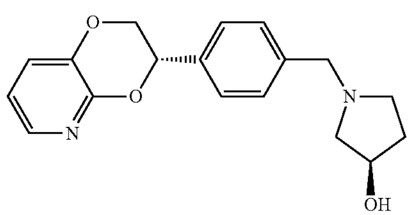 [SMILES: O[C@@H]1CCN(Cc2ccc([C@H]3COc4cccnc4O3)cc2)C1] | (3R)-1-{4-[(3S)-2,3-dihydro[1,4]dioxino[2,3-b]pyridin-3-yl]benzyl}pyrrolidin-3-ol |
| 145 | 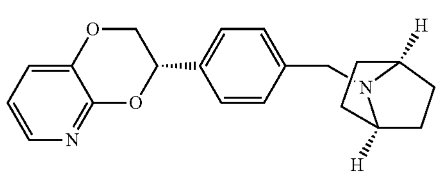 [SMILES: c1cnc2c(c1)OC[C@H](c1ccc(CN3[C@H]4CC[C@@H]3CC4)cc1)O2] | (3S)-3-{4-[(1s,4s)-7-azabicyclo[2.2.1]hept-7-ylmethyl]phenyl}-2,3-dihydro[1,4]dioxino[2,3-b]pyridine |
| 146 | 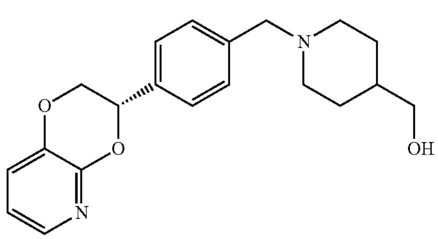 [SMILES: OCC1CCN(Cc2ccc([C@H]3COc4cccnc4O3)cc2)CC1] | (1-{4-[(3S)-2,3-dihydro[1,4]dioxino[2,3-b]pyridin-3-yl]benzyl}piperidin-4-yl)methanol |

TABLE 1-continued

Exemplary compounds of the invention.

| Cpd No. | Structure | Name |
|---|---|---|
| 147 | 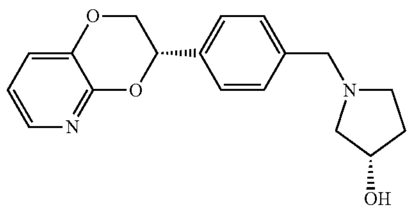 [SMILES: O[C@H]1CCN(Cc2ccc([C@H]3COc4cccnc4O3)cc2)C1] | (3S)-1-{4-[(3S)-2,3-dihydro[1,4]dioxino[2,3-b]pyridin-3-yl]benzyl}pyrrolidin-3-ol |
| 148 | 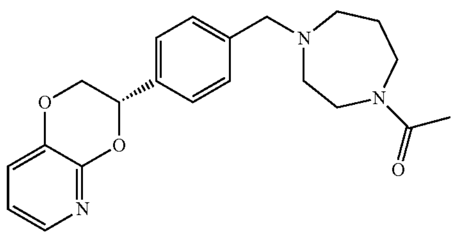 | 1-(4-{4-[(3S)-2,3-dihydro[1,4]dioxino[2,3-b]pyridin-3-yl]benzyl}-1,4-diazepan-1-yl)ethanone |
| 149 | 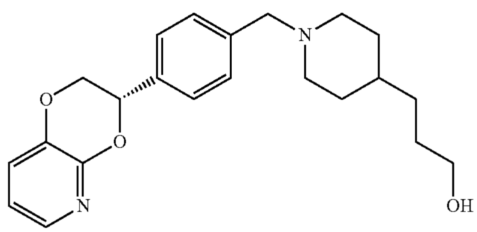 [SMILES: OCCCC1CCN(Cc2ccc([C@H]3COc4cccnc4O3)cc2)CC1] | 3-(1-{4-[(3S)-2,3-dihydro[1,4]dioxino[2,3-b]pyridin-3-yl]benzyl}piperidin-4-yl)propan-1-ol |
| 150 | 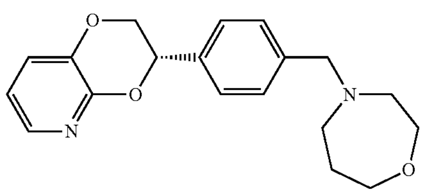 [SMILES: c1cnc2c(c1)OC[C@H](c1ccc(CN3CCCOCC3)cc1)O2] | (3S)-3-[4-(1,4-oxazepan-4-ylmethyl)phenyl]-2,3-dihydro[1,4]dioxino[2,3-b]pyridine |
| 151 | 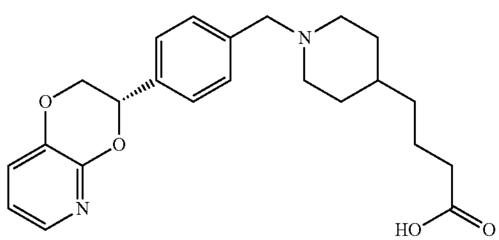 | 4-(1-{4-[(3S)-2,3-dihydro[1,4]dioxino[2,3-b]pyridin-3-yl]benzyl}piperidin-4-yl)butanoic acid |
| 152 | 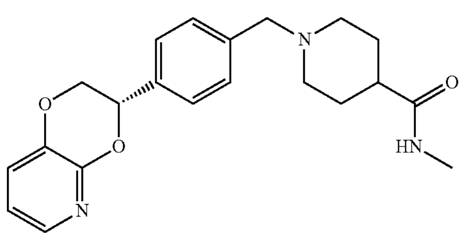 [SMILES: CNC(=O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}-N-methylpiperidine-4-carboxamide |
| 153 | 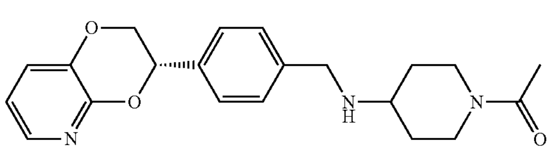 [SMILES: CC(=O)N1CCC(NCc2ccc([C@H]3COc4cccnc4O3)cc2)CC1] | 1-[4-({4-[(3S)-2,3-dihydro[1,4]dioxino[2,3-b]pyridin-3-yl]benzyl}amino)piperidin-1-yl]ethanone |

TABLE 1-continued

Exemplary compounds of the invention.

| Cpd No. | Structure | Name |
|---|---|---|
| 154 | 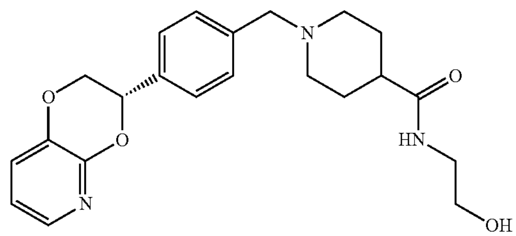 [SMILES: O=C(NCCO)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}-N-(2-hydroxyethyl)piperidine-4-carboxamide |
| 155 | 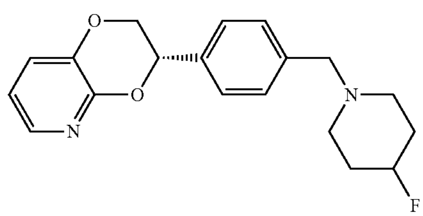 [SMILES: FC1CCN(Cc2ccc([C@H]3COc4cccnc4O3)cc2)CC1] | (3S)-3-{4-[(4-fluoropiperidin-1-yl)methyl]phenyl}-2,3-dihydro[1,4]dioxino[2,3-b]pyridine |
| 156 | 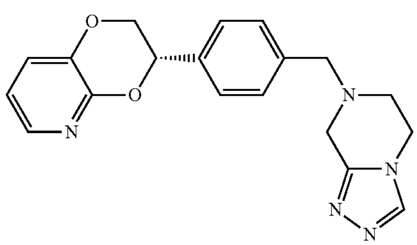 [SMILES: c1cnc2c(c1)OC[C@H](c1ccc(CN3CCn4cnnc4C3)cc1)O2] | (3S)-3-[4-(5,6-dihydro[1,2,4]triazolo[4,3-a]pyrazin-7(8H)-ylmethyl)phenyl]-2,3-dihydro[1,4]dioxino[2,3-b]pyridine |
| 157 | 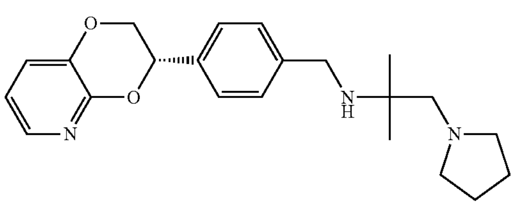 [SMILES: CC(C)(CN1CCCC1)NCc1ccc([C@H]2COc3cccnc3O2)cc1] | N-{4-[(3S)-2,3-dihydro[1,4]dioxino[2,3-b]pyridin-3-yl]benzyl}-2-methyl-1-(pyrrolidin-1-yl)propan-2-amine |
| 158 | 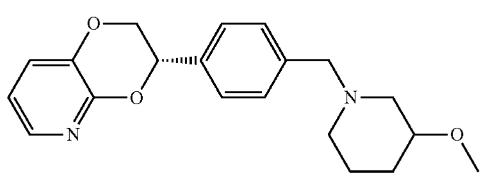 [SMILES: COC1CCCN(Cc2ccc([C@H]3COc4cccnc4O3)cc2)C1] | (3S)-3-{4-[(3-methoxypiperidin-1-yl)methyl]phenyl}-2,3-dihydro[1,4]dioxino[2,3-b]pyridine |
| 159 | 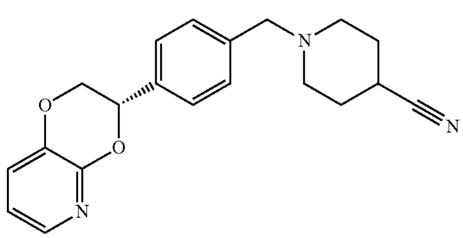 [SMILES: N#CC1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carbonitrile |
| 160 | 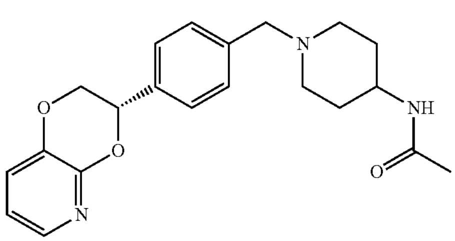 [SMILES: CC(=O)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)acetamide |

TABLE 1-continued

Exemplary compounds of the invention.

| Cpd No. | Structure | Name |
|---|---|---|
| 161 | 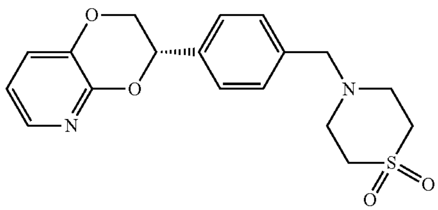 [SMILES: O=S1(=O)CCN(Cc2ccc([C@H]3COc4cccnc4O3)cc2)CC1] | (3S)-3-{4-[(1,1-dioxidothiomorpholin-4-yl)methyl]phenyl}-2,3-dihydro[1,4]dioxino[2,3-b]pyridine |
| 162 | 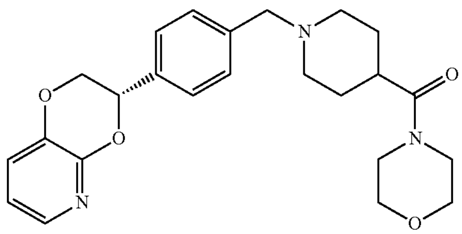 [SMILES: O=C(C1CCN(Cc2ccc([C@H]3COc4cccnc4O3)cc2)CC1)N1CCOCC1] | (1-{4-[(3S)-2,3-dihydro[1,4]dioxino[2,3-b]pyridin-3-yl]benzyl}piperidin-4-yl)(morpholin-4-yl)methanone |
| 163 | 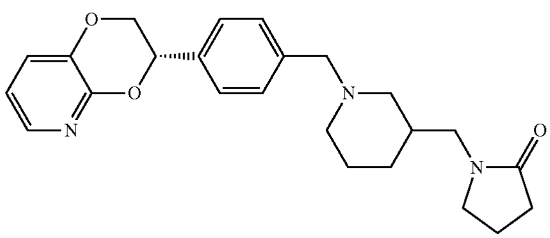 [SMILES: O=C1CCCN1CC1CCCN(Cc2ccc([C@H]3COc4cccnc4O3)cc2)C1] | 1-[(1-{4-[(3S)-2,3-dihydro[1,4]dioxino[2,3-b]pyridin-3-yl]benzyl}piperidin-3-yl)methyl]pyrrolidin-2-one |
| 164 | 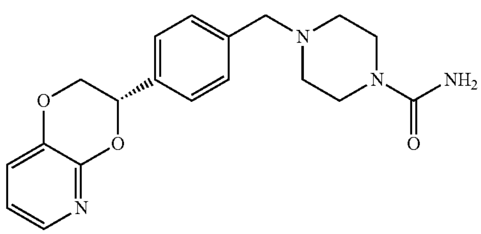 [SMILES: NC(=O)N1CCN(Cc2ccc([C@H]3COc4cccnc4O3)cc2)CC1] | 4-{4-[(3S)-2,3-dihydro[1,4]dioxino[2,3-b]pyridin-3-yl]benzyl}piperazine-1-carboxamide |
| 165 | 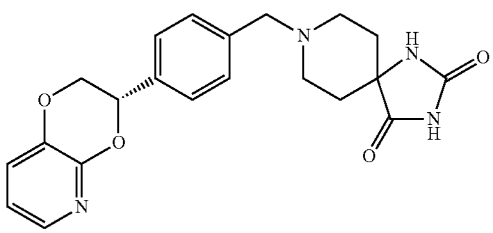 [SMILES: O=C1NC(=O)C2(CCN(Cc3ccc([C@H]4COc5cccnc5O4)cc3)CC2)N1] | 8-{4-[(3S)-2,3-dihydro[1,4]dioxino[2,3-b]pyridin-3-yl]benzyl}-1,3,8-triazaspiro[4.5]decane-2,4-dione |
| 166 | 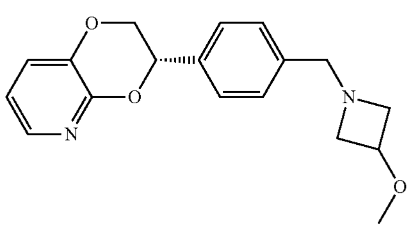 [SMILES: COC1CN(Cc2ccc([C@H]3COc4cccnc4O3)cc2)C1] | (3S)-3-{4-[(3-methoxyazetidin-1-yl)methyl]phenyl}-2,3-dihydro[1,4]dioxino[2,3-b]pyridine |
| 167 | 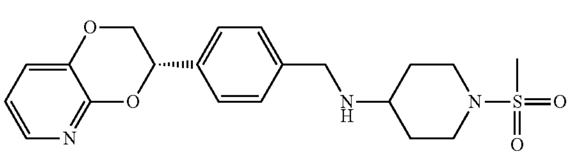 [SMILES: CS(=O)(=O)N1CCC(NCc2ccc([C@H]3COc4cccnc4O3)cc2)CC1] | N-{4-[(3S)-2,3-dihydro[1,4]dioxino[2,3-b]pyridin-3-yl]benzyl}-1-(methylsulfonyl)piperidin-4-amine |

TABLE 1-continued

Exemplary compounds of the invention.

| Cpd No. | Structure | Name |
|---|---|---|
| 168 | 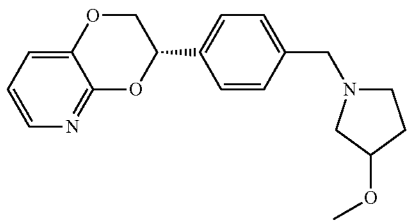 | (3S)-3-{4-[(3-methoxypyrrolidin-1-yl)methyl]phenyl}-2,3-dihydro[1,4]dioxino[2,3-b]pyridine |
| 169 | 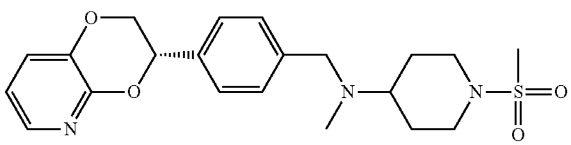 [SMILES: CN(Cc1ccc([C@H]2COc3cccnc3O2)cc1)C1CCN(S(C)(=O)=O)CC1] | N-{4-[(3S)-2,3-dihydro[1,4]dioxino[2,3-b]pyridin-3-yl]benzyl}-N-methyl-1-(methylsulfonyl)piperidin-4-amine |
| 170 | 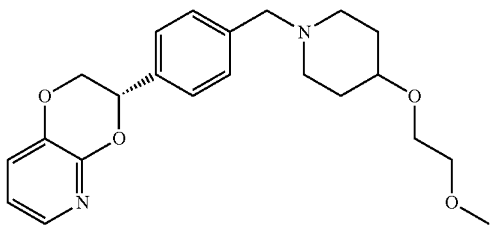 [SMILES: COCCOC1CCN(Cc2ccc([C@H]3COc4cccnc4O3)cc2)CC1] | (3S)-3-(4-{[4-(2-methoxyethoxy)piperidin-1-yl]methyl}phenyl)-2,3-dihydro[1,4]dioxino[2,3-b]pyridine |
| 171 | 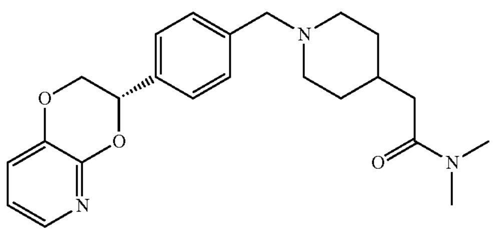 [SMILES: CN(C)C(=O)CC1CCN(Cc2ccc([C@H]3COc4cccnc4O3)cc2)CC1] | 2-(1-{4-[(3S)-2,3-dihydro[1,4]dioxino[2,3-b]pyridin-3-yl]benzyl}piperidin-4-yl)-N,N-dimethylacetamide |
| 172 | 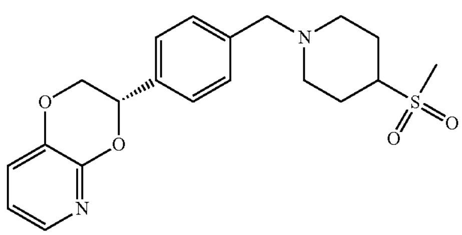 [SMILES: CS(=O)(=O)C1CCN(Cc2ccc([C@H]3COc4cccnc4O3)cc2)CC1] | (3S)-3-(4-{[4-(methylsulfonyl)piperidin-1-yl]methyl}phenyl)-2,3-dihydro[1,4]dioxino[2,3-b]pyridine |
| 173 | 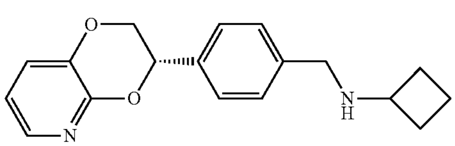 [SMILES: c1cnc2c(c1)OC[C@H](c1ccc(CNC3CCC3)cc1)O2] | N-{4-[(3S)-2,3-dihydro[1,4]dioxino[2,3-b]pyridin-3-yl]benzyl}cyclobutanamine |
| 174 | 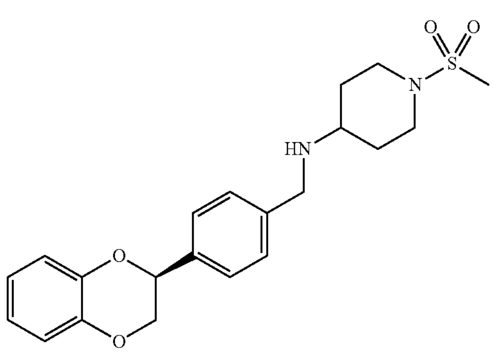 [SMILES: CS(=O)(=O)N1CCC(NCc2ccc([C@H]3COc4ccccc4O3)cc2)CC1] | N-{4-[(2S)-2,3-dihydro-1,4-benzodioxin-2-yl]benzyl}-1-(methylsulfonyl)piperidin-4-amine |

TABLE 1-continued
Exemplary compounds of the invention.
| Cpd No. | Structure | Name |
|---|---|---|
| 175 | 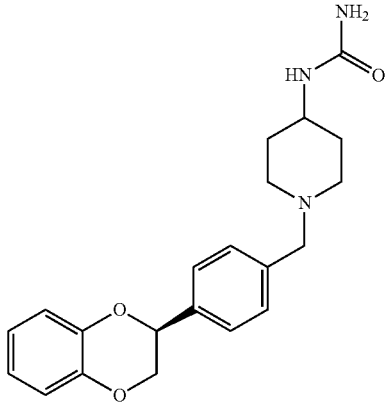 [SMILES: NC(=O)NC1CCN(Cc2ccc([C@H]3COc4ccccc4O3)cc2)CC1] | 1-(1-{4-[(2S)-2,3-dihydro-1,4-benzodioxin-2-yl]benzyl}piperidin-4-yl)urea |
| 176 | 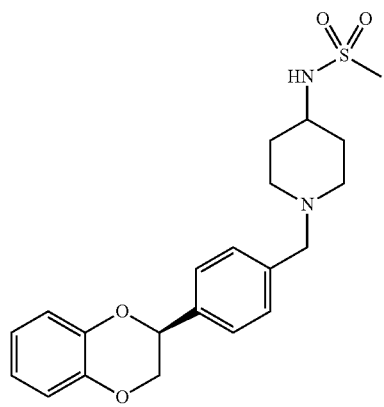 [SMILES: CS(=O)(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)methanesulfonamide |
| 177 | 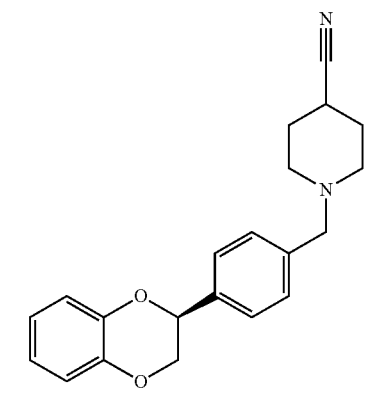 [SMILES: N#CC1CCN(Cc2ccc([C@H]3COc4ccccc4O3)cc2)CC1] | 1-{4-[(2S)-2,3-dihydro-1,4-benzodioxin-2-yl]benzyl}piperidin-4-carbonitrile |

TABLE 1-continued
Exemplary compounds of the invention.
| Cpd No. | Structure | Name |
|---|---|---|
| 178 | 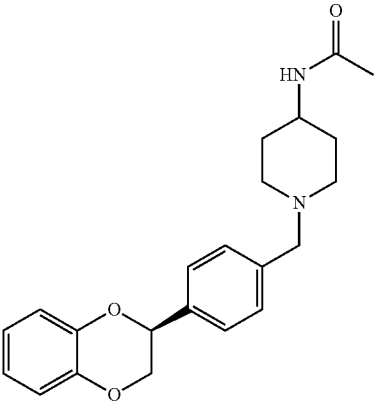 [SMILES: CC(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)acetamide |
| 179 | 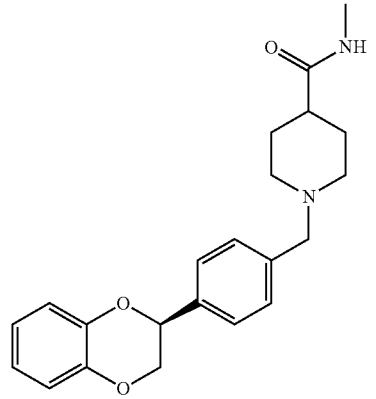 [SMILES: CNC(=O)C1CCN(Cc2ccc([C@H]3COc4ccccc4O3)cc2)CC1] | 1-{4-[(2S)-2,3-dihydro-1,4-benzodioxin-2-yl]benzyl}-N-methylpiperidine-4-carboxamide |
| 180 | 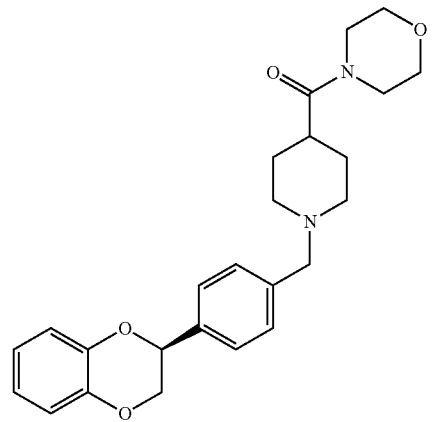 [SMILES: O=C(C1CCN(Cc2ccc([C@H]3COc4ccccc4O3)cc2)CC1)N1CCOCC1] | (1-{4-[(2S)-2,3-dihydro-1,4-benzodioxin-2-yl]benzyl}piperidin-4-yl)(morpholin-4-yl)methanone |

TABLE 1-continued

Exemplary compounds of the invention.

| Cpd No. | Structure | Name |
| --- | --- | --- |
| 181 | 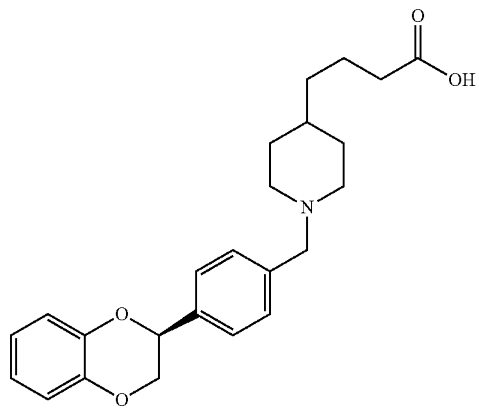 [SMILES: O=C(O)CCCC1CCN(Cc2ccc([C@H]3COc4ccccc4O3)cc2)CC1] | 4-(1-{4-[(2S)-2,3-dihydro-1,4-benzodioxin-2-yl]benzyl}piperidin-4-yl)butanoic acid |
| 182 | 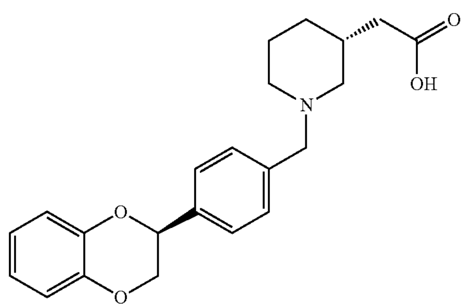 [SMILES: O=C(O)C[C@H]1CCCN(Cc2ccc([C@H]3COc4ccccc4O3)cc2)C1] | [(3R)-1-{4-[(2S)-2,3-dihydro-1,4-benzodioxin-2-yl]benzyl}piperidin-3-yl]acetic acid |
| 183 | 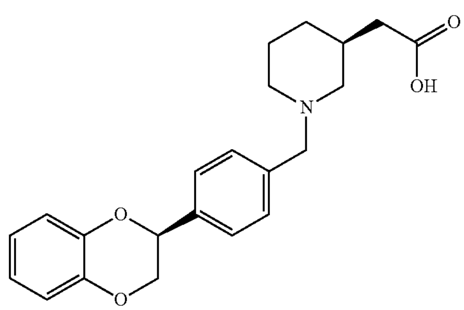 [SMILES: O=C(O)C[C@@H]1CCCN(Cc2ccc([C@H]3COc4ccccc4O3)cc2)C1] | [(3S)-1-{4-[(2S)-2,3-dihydro-1,4-benzodioxin-2-yl]benzyl}piperidin-3-yl]acetic acid |
| 184 | 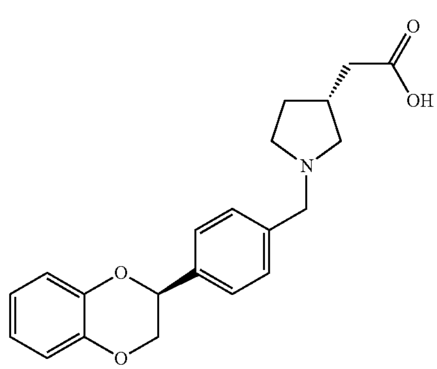 [SMILES: O=C(O)C[C@H]1CCN(Cc2ccc([C@H]3COc4ccccc4O3)cc2)C1] | [(3R)-1-{4-[(2S)-2,3-dihydro-1,4-benzodioxin-2-yl]benzyl}pyrrolidin-3-yl]acetic acid |

TABLE 1-continued
Exemplary compounds of the invention.
| Cpd No. | Structure | Name |
|---|---|---|
| 185 | 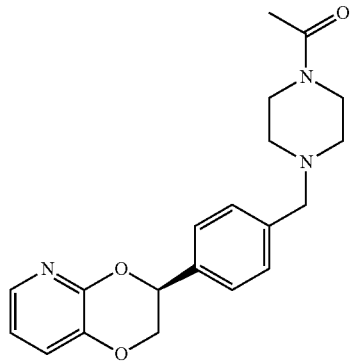 [SMILES: CC(=O)N1CCN(Cc2ccc([C@H]3COc4cccnc4O3)cc2)CC1] | 1-(4-{4-[(3S)-2,3-dihydro[1,4]dioxino[2,3-b]pyridin-3-yl]benzyl}piperazin-1-yl)ethanone |
| 186 | 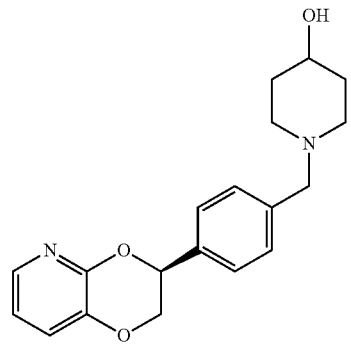 [SMILES: OC1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidin-4-ol |
| 187 | 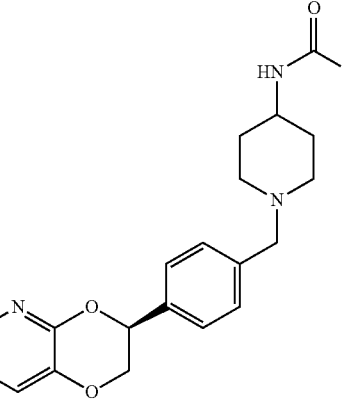 | 1-(1-{4-[(3S)-2,3-dihydro[1,4]dioxino[2,3-b]pyridin-3-yl]benzyl}piperidin-4-yl)urea |
| 188 | 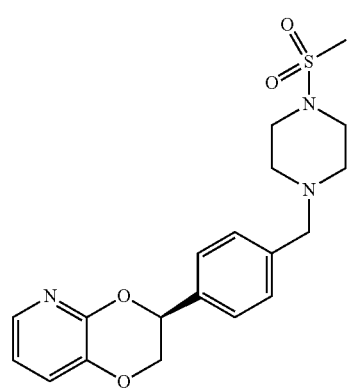 [SMILES: CS(=O)(=O)N1CCN(Cc2ccc([C@H]3COc4cccnc4O3)cc2)CC1] | (3S)-3-(4-{[4-(methylsulfonyl)piperazin-1-yl]methyl}phenyl)-2,3-dihydro[1,4]dioxino[2,3-b]pyridine |

TABLE 1-continued

Exemplary compounds of the invention.

| Cpd No. | Structure | Name |
|---|---|---|
| 189 | 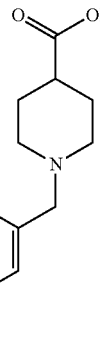 | 1-{4-[(3S)-2,3-dihydro[1,4]dioxino[2,3-b]pyridin-3-yl]benzyl}piperidine-4-carboxylic acid |
| 190 | 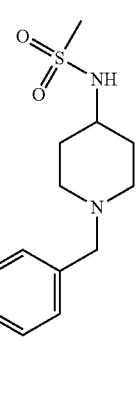 | N-(1-{4-[(3S)-2,3-dihydro[1,4]dioxino[2,3-b]pyridin-3-yl]benzyl}piperidin-4-yl)methanesulfonamide |
| 191 | 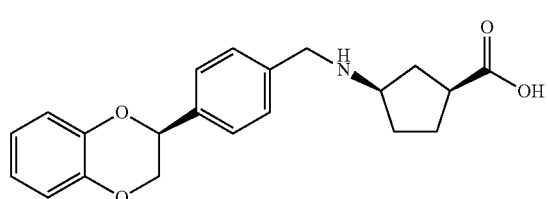 | (1S,3R)-3-({4-[(2S)-2,3-dihydro-1,4-benzodioxin-2-yl]benzyl}amino)cyclopentane-carboxylic acid |
| 192 | 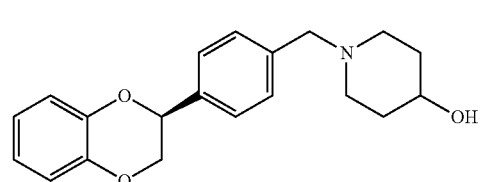 | 1-{4-[(2S)-2,3-dihydro-1,4-benzodioxin-2-yl]benzyl}piperidin-4-ol |
| 193 | 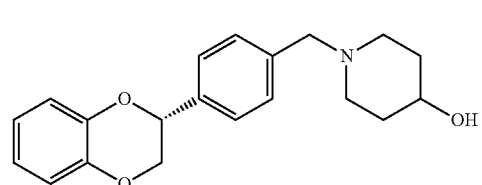 | 1-{4-[(2R)-2,3-dihydro-1,4-benzodioxin-2-yl]benzyl}piperidin-4-ol |
| 194 | 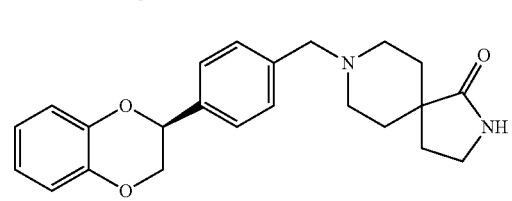 [SMILES: O=C1NCCC12CCN(Cc1ccc([C@H]3COc4ccccc4O3)cc1)CC2] | 8-{4-[(2S)-2,3-dihydro-1,4-benzodioxin-2-yl]benzyl}-2,8-diazaspiro[4.5]decan-1-one |

TABLE 1-continued

Exemplary compounds of the invention.

| Cpd No. | Structure | Name |
|---|---|---|
| 195 | 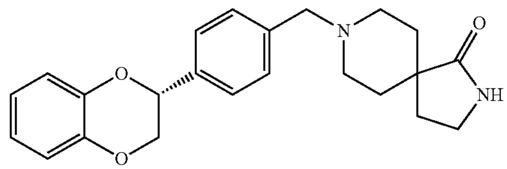 | 8-{4-[(2R)-2,3-dihydro-1,4-benzodioxin-2-yl]benzyl}-2,8-diazaspiro[4.5]decan-1-one |
| 196 | 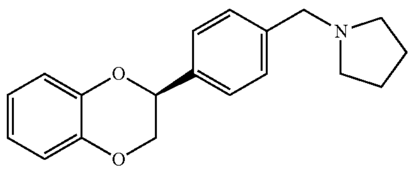 [SMILES: c1ccc2c(c1)OC[C@H](c1ccc(CN3CCCC3)cc1)O2] | 1-{4-[(2S)-2,3-dihydro-1,4-benzodioxin-2-yl]benzyl}pyrrolidine |
| 197 | 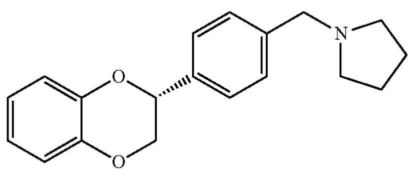 [SMILES: c1ccc2c(c1)OC[C@@H](c1ccc(CN3CCCC3)cc1)O2] | 1-{4-[(2R)-2,3-dihydro-1,4-benzodioxin-2-yl]benzyl}pyrrolidine |
| 198 | 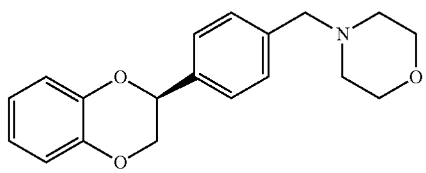 [SMILES: c1ccc2c(c1)OC[C@H](c1ccc(CN3CCOCC3)cc1)O2] | 4-{4-[(2S)-2,3-dihydro-1,4-benzodioxin-2-yl]benzyl}morpholine |
| 199 | 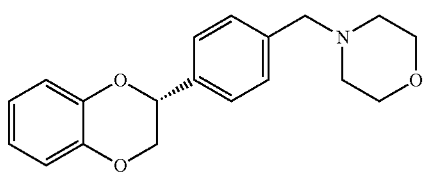 | 4-{4-[(2R)-2,3-dihydro-1,4-benzodioxin-2-yl]benzyl}morpholine |
| 200 | 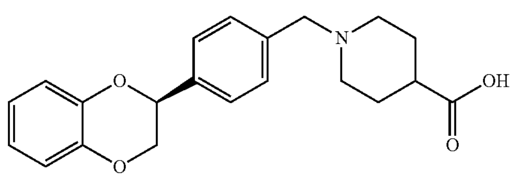 [SMILES: O=C(O)C1CCN(Cc2ccc([C@H]3COc4ccccc4O3)cc2)CC1] | 1-{4-[(2S)-2,3-dihydro-1,4-benzodioxin-2-yl]benzyl}piperidine-4-carboxylic acid |
| 201 | Chiral | 1-{4-[(2R)-2,3-dihydro-1,4-benzodioxin-2-yl]benzyl}piperidine-4-carboxylic acid |
| 202 | 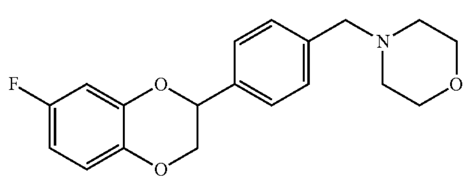 [SMILES: Fc1ccc2c(c1)OC(c1ccc(CN3CCOCC3)cc1)CO2] | 4-[4-(7-fluoro-2,3-dihydro-1,4-benzodioxin-2-yl)benzyl]morpholine |

TABLE 1-continued

Exemplary compounds of the invention.

| Cpd No. | Structure | Name |
|---|---|---|
| 203 | 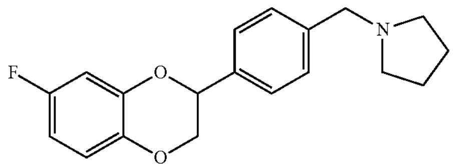 [SMILES: Fc1ccc2c(c1)OC(c1ccc(CN3CCCC3)cc1)CO2] | 1-[4-(7-fluoro-2,3-dihydro-1,4-benzodioxin-2-yl)benzyl]pyrrolidine |
| 204 | 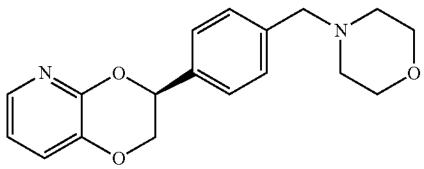 [SMILES: c1cnc2c(c1)OC[C@H](c1ccc(CN3CCOCC3)cc1)O2] | (3S)-3-[4-(morpholin-4-ylmethyl)phenyl]-2,3-dihydro[1,4]dioxino[2,3-b]pyridine |
| 205 | 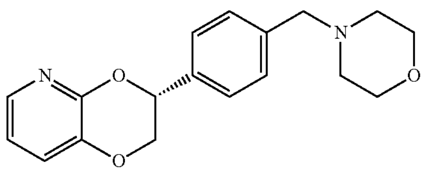 [SMILES: c1cnc2c(c1)OC[C@@H](c1ccc(CN3CCOCC3)cc1)O2] | (3R)-3-[4-(morpholin-4-ylmethyl)phenyl]-2,3-dihydro[1,4]dioxino[2,3-b]pyridine |
| 206 | 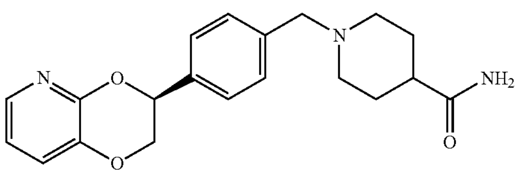 [SMILES: NC(=O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carboxamide |
| 207 | 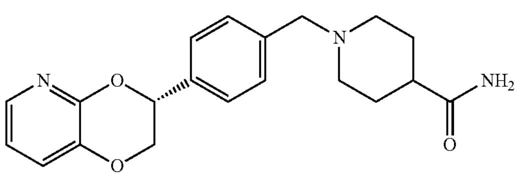 [SMILES: NC(=O)C1CCN(Cc2ccc([C@@H]3COc4cccnc4O3)cc2)CC1] | 1-{4-[(3R)-2,3-dihydro[1,4]dioxino[2,3-b]pyridin-3-yl]benzyl}piperidine-4-carboxamide |
| 208 | 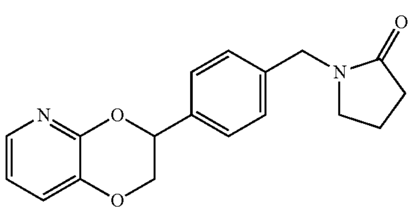 [SMILES: O=C1CCCN1Cc1ccc(C2COc3cccnc3O2)cc1] | 1-[4-(2,3-dihydro[1,4]dioxino[2,3-b]pyridin-3-yl)benzyl]pyrrolidin-2-one |
| 209 | 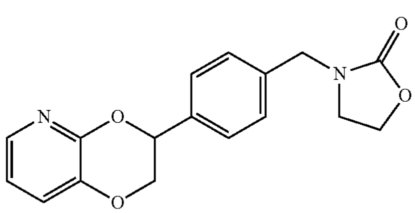 [SMILES: O=C1OCCN1Cc1ccc(C2COc3cccnc3O2)cc1] | 3-[4-(2,3-dihydro[1,4]dioxino[2,3-b]pyridin-3-yl)benzyl]-1,3-oxazolidin-2-one |
| 210 | 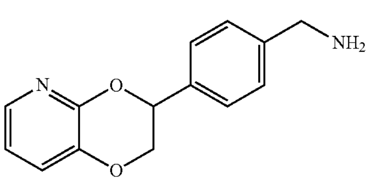 [SMILES: NCc1ccc(C2COc3cccnc3O2)cc1] | 1-[4-(2,3-dihydro[1,4]dioxino[2,3-b]pyridin-3-yl)phenyl]methanamine |

TABLE 1-continued

Exemplary compounds of the invention.

| Cpd No. | Structure | Name |
| --- | --- | --- |
| 211 | 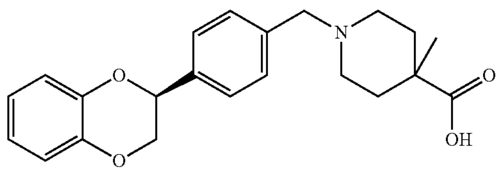 [SMILES: CC1(C(=O)O)CCN(Cc2ccc([C@H]3COc4ccccc4O3)cc2)CC1] | 1-{4-[(2S)-2,3-dihydro-1,4-benzodioxin-2-yl]benzyl}-4-methylpiperidine-4-carboxylic acid |
| 212 | 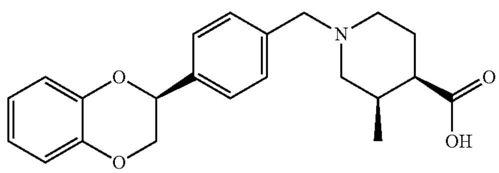 [SMILES: C[C@H]1CN(Cc2ccc([C@H]3COc4ccccc4O3)cc2)CC[C@H]1C(=O)O] | (3R,4R)-1-{4-[(2S)-2,3-dihydro-1,4-benzodioxin-2-yl]benzyl}-3-methylpiperidine-4-carboxylic acid |
| 213 | 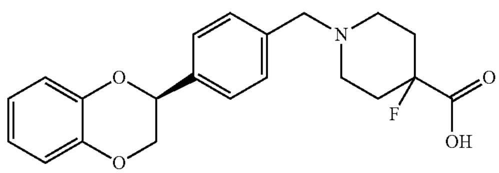 [SMILES: O=C(O)C1(F)CCN(Cc2ccc([C@H]3COc4ccccc4O3)cc2)CC1] | 1-{4-[(2S)-2,3-dihydro-1,4-benzodioxin-2-yl]benzyl}-4-fluoropiperidine-4-carboxylic acid |
| 214 | 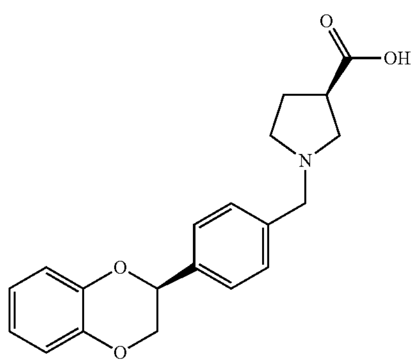 [SMILES: O=C(O)[C@@H]1CCN(Cc2ccc([C@H]3COc4ccccc4O3)cc2)C1] | (3R)-1-{4-[(2S)-2,3-dihydro-1,4-benzodioxin-2-yl]benzyl}pyrrolidine-3-carboxylic acid |
| 215 | 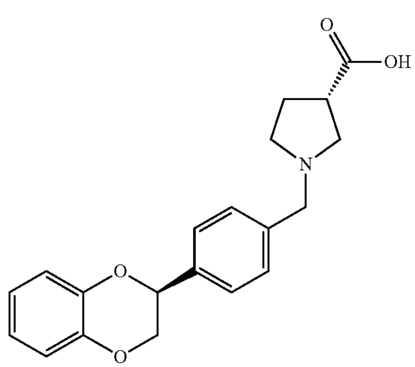 [SMILES: O=C(O)[C@H]1CCN(Cc2ccc([C@H]3COc4ccccc4O3)cc2)C1] | (3S)-1-{4-[(2S)-2,3-dihydro-1,4-benzodioxin-2-yl]benzyl}pyrrolidine-3-carboxylic acid |
| 216 | 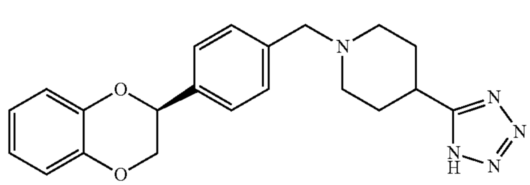 [SMILES: c1ccc2c(c1)OC[C@H](c1ccc(CN3CCC(c4nnn[nH]4)CC3)cc1)O2] | 1-{4-[(2S)-2,3-dihydro-1,4-benzodioxin-2-yl]benzyl}-4-(1H-tetrazol-5-yl)piperidine |

TABLE 1-continued
Exemplary compounds of the invention.
| Cpd No. | Structure | Name |
|---|---|---|
| 217 | 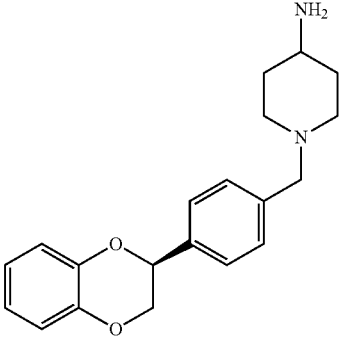 [SMILES: NC1CCN(Cc2ccc([C@H]3COc4ccccc4O3)cc2)CC1] | 1-{4-[(2S)-2,3-dihydro-1,4-benzodioxin-2-yl]benzyl}piperidin-4-amine |
| 218 | 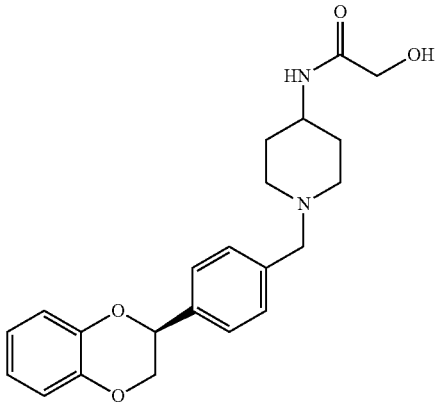 [SMILES: O=C(CO)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-hydroxyacetamide |
| 219 | 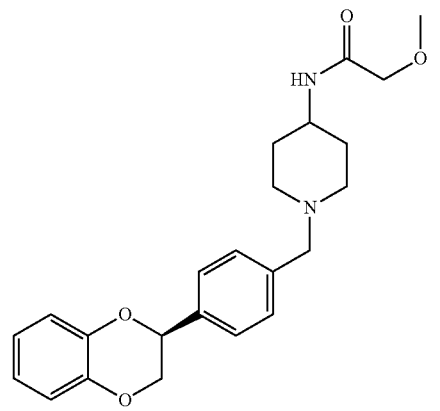 [SMILES: COCC(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-methoxyacetamide |
| 220 | 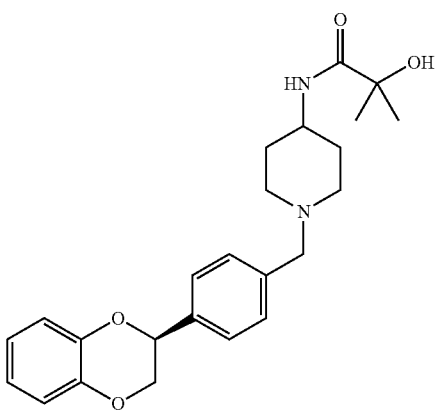 [SMILES: CC(C)(O)C(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-hydroxy-2-methylpropanamide |

TABLE 1-continued

Exemplary compounds of the invention.

| Cpd No. | Structure | Name |
|---|---|---|
| 221 | 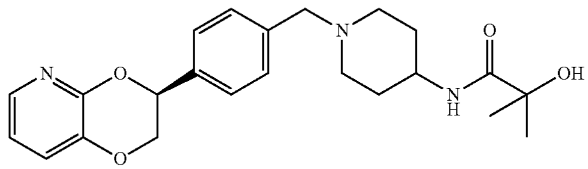 [SMILES: CC(C)(O)C(=O)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)-2-hydroxy-2-methylpropanamide |
| 222 | 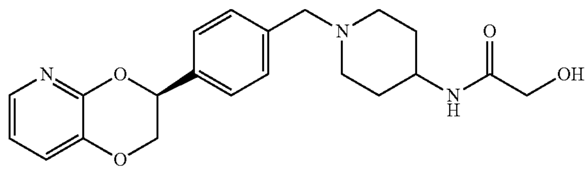 [SMILES: O=C(CO)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)-2-hydroxyacetamide |
| 223 | 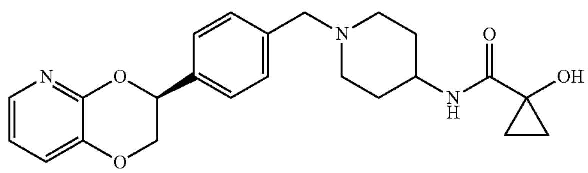 [SMILES: O=C(NC1CCN(Cc2ccc([C@H]3COc4cccnc4O3)cc2)CC1)C1(O)CC1] | N-(1-{4-[(3S)-2,3-dihydro[1,4]dioxino[2,3-b]pyridin-3-yl]benzyl}piperidin-4-yl)-1-hydroxycyclopropanecarboxamide |
| 224 | 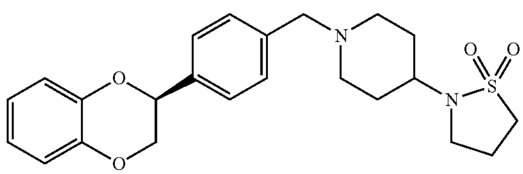 [SMILES: O=S1(=O)CCCN1C1CCN(Cc2ccc([C@H]3COc4ccccc4O3)cc2)CC1] | 1-{4-[(2S)-2,3-dihydro-1,4-benzodioxin-2-yl]benzyl}-4-(1,1-dioxido-1,2-thiazolidin-2-yl)piperidine |
| 225 | 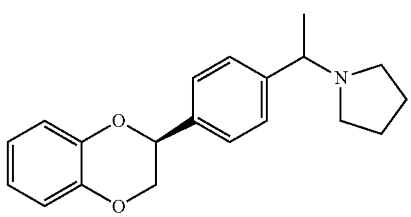 [SMILES: CC(c1ccc([C@H]2COc3ccccc3O2)cc1)N1CCCC1] | 1-(1-{4-[(2S)-2,3-dihydro-1,4-benzodioxin-2-yl]phenyl}ethyl)pyrrolidine |
| 226 | 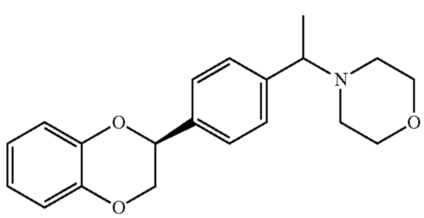 [SMILES: CC(c1ccc([C@H]2COc3ccccc3O2)cc1)N1CCOCC1] | 4-(1-{4-[(2S)-2,3-dihydro-1,4-benzodioxin-2-yl]phenyl}ethyl)morpholine |
| 227 | 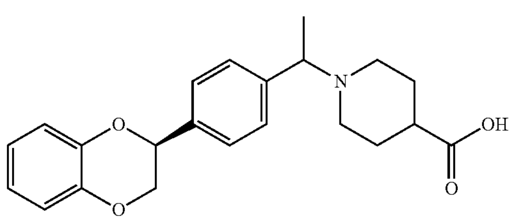 [SMILES: CC(c1ccc([C@H]2COc3ccccc3O2)cc1)N1CCC(C(=O)O)CC1] | 1-(1-{4-[(2S)-2,3-dihydro-1,4-benzodioxin-2-yl]phenyl}ethyl)piperidine-4-carboxylic acid |
| 228 | 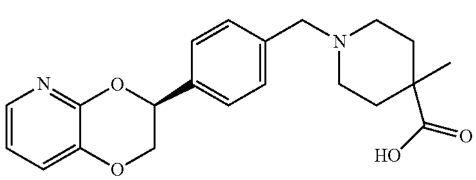 [SMILES: CC1(C(=O)O)CCN(Cc2ccc([C@H]3COc4cccnc4O3)cc2)CC1] | 1-{4-[(3S)-2,3-dihydro[1,4]dioxino[2,3-b]pyridin-3-yl]benzyl}-4-methylpiperidine-4-carboxylic acid |

TABLE 1-continued

Exemplary compounds of the invention.

| Cpd No. | Structure | Name |
|---|---|---|
| 229 | 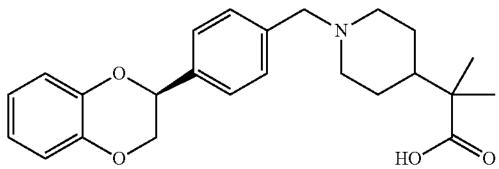 [SMILES: CC(C)(C(=O)O)C1CCN(Cc2ccc([C@H]3COc4ccccc4O3)cc2)CC1] | 2-(1-{4-[(2S)-2,3-dihydro-1,4-benzodioxin-2-yl]benzyl}piperidin-4-yl)-2-methylpropanoic acid |
| 230 | 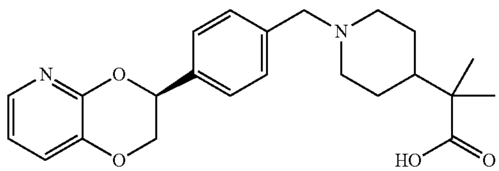 [SMILES: CC(C)(C(=O)O)C1CCN(Cc2ccc([C@H]3COc4cccnc4O3)cc2)CC1] | 2-(1-{4-[(3S)-2,3-dihydro[1,4]dioxino[2,3-b]pyridin-3-yl]benzyl}piperidin-4-yl)-2-methylpropanoic acid |
| 231 | 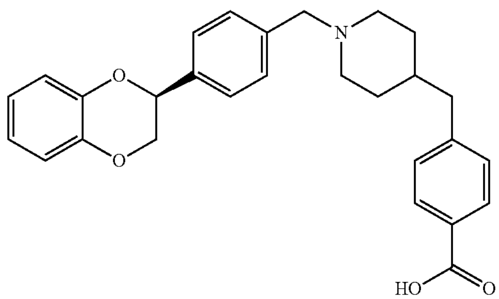 [SMILES: O=C(O)c1ccc(CC2CCN(Cc3ccc([C@H]4COc5ccccc5O4)cc3)CC2)cc1] | 4-[(1-{4-[(2S)-2,3-dihydro-1,4-benzodioxin-2-yl]benzyl}piperidin-4-yl)methyl]benzoic acid |
| 232 | 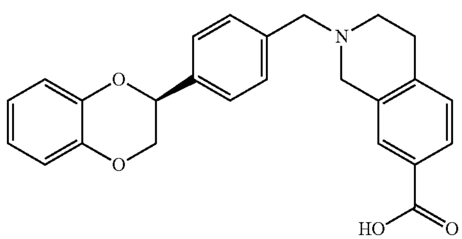 [SMILES: O=C(O)c1ccc2c(c1)CN(Cc1ccc([C@H]3COc4ccccc4O3)cc1)CC2] | 2-{4-[(2S)-2,3-dihydro-1,4-benzodioxin-2-yl]benzyl}-1,2,3,4-tetrahydroisoquinoline-7-carboxylic acid |
| 233 | 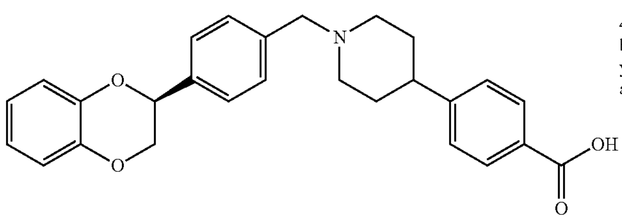 [SMILES: O=C(O)c1ccc(C2CCN(Cc3ccc([C@H]4COc5ccccc5O4)cc3)CC2)cc1] | 4-(1-{4-[(2S)-2,3-dihydro-1,4-benzodioxin-2-yl]benzyl}piperidin-4-yl)benzoic acid |
| 234 | 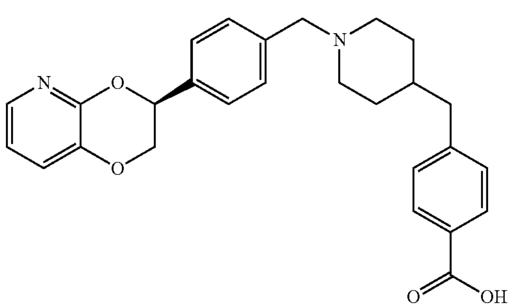 [SMILES: O=C(O)c1ccc(CC2CCN(Cc3ccc([C@H]4COc5cccnc5O4)cc3)CC2)cc1] | 4-[(1-{4-[(3S)-2,3-dihydro[1,4]dioxino[2,3-b]pyridin-3-yl]benzyl}piperidin-4-yl)methyl]benzoic acid |

TABLE 1-continued

Exemplary compounds of the invention.

| Cpd No. | Structure | Name |
|---|---|---|
| 235 | 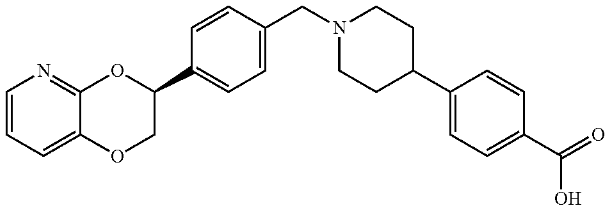 [SMILES: O=C(O)c1ccc(C2CCN(Cc3ccc([C@H]4COc5cccnc5O4)cc3)CC2)cc1] | 4-(1-{4-[(3S)-2,3-dihydro[1,4]dioxino[2,3-b]pyridin-3-yl]benzyl}piperidin-4-yl)benzoic acid |
| 236 | 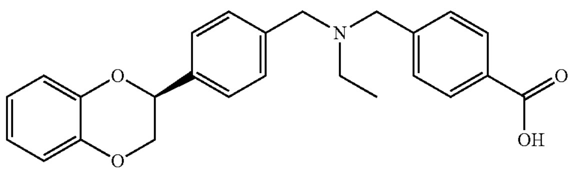 [SMILES: CCN(Cc1ccc(C(=O)O)cc1)Cc1ccc([C@H]2COc3ccccc3O2)cc1] | 4-{[[{4-[(2S)-2,3-dihydro-1,4-benzodioxin-2-yl]benzyl}(ethyl)amino]methyl}benzoic acid |
| 237 | 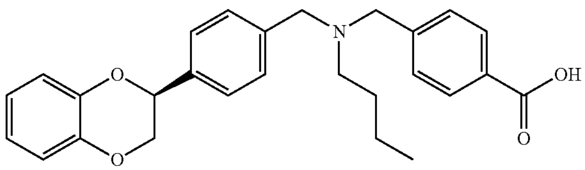 [SMILES: CCCCN(Cc1ccc(C(=O)O)cc1)Cc1ccc([C@H]2COc3ccccc3O2)cc1] | 4-[(butyl{4-[(2S)-2,3-dihydro-1,4-benzodioxin-2-yl]benzyl}amino)methyl]benzoic acid |
| 238 | 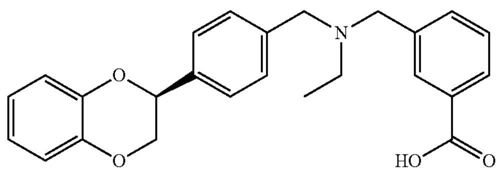 [SMILES: CCN(Cc1ccc([C@H]2COc3ccccc3O2)cc1)Cc1cccc(C(=O)O)c1] | 3-{[[{4-[(2S)-2,3-dihydro-1,4-benzodioxin-2-yl]benzyl}(ethyl)amino]methyl}benzoic acid |
| 239 | 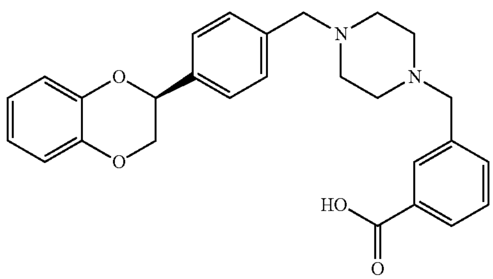 [SMILES: O=C(O)c1cccc(CN2CCN(Cc3ccc([C@H]4COc5ccccc5O4)cc3)CC2)c1] | 3-[(4-{4-[(2S)-2,3-dihydro-1,4-benzodioxin-2-yl]benzyl}piperazin-1-yl)methyl]benzoic acid |

In one embodiment, the invention relates to any of the compounds depicted in Table 1, and pharmaceutically acceptable salts thereof.

In another embodiment, the invention relates to a compound selected from the group consisting of:
4-(1-{4-[(2S)-2,3-dihydro-1,4-benzodioxin-2-yl]benzyl}piperidin-4-yl)butanoic acid;
4-(1-{4-[(3S)-2,3-dihydro[1,4]dioxino[2,3-b]pyridin-3-yl]benzyl}piperidin-4-yl)benzoic acid;
(3S)-3-{4-[(1s,4s)-7-azabicyclo[2.2.1]hept-7-ylmethyl]phenyl}-2,3-dihydro[1,4]dioxino[2,3-b]pyridine;
N-(1-{4-[(3S)-2,3-dihydro[1,4]dioxino[2,3-b]pyridin-3-yl]benzyl}piperidin-4-yl)methanesulfonamide;
(3S)-3-[4-(azepan-1-ylmethyl)phenyl]-2,3-dihydro[1,4]dioxino[2,3-b]pyridine;
1-{4-[(2S)-2,3-dihydro-1,4-benzodioxin-2-yl]benzyl}-2-methylpiperidine;
7-{4-[(2S)-2,3-dihydro-1,4-benzodioxin-2-yl]benzyl}-1,7-diazaspiro[4.4]nonane-1-carboxamide;
7-{4-[(3S)-2,3-dihydro[1,4]dioxino[2,3-b]pyridin-3-yl]benzyl}-1,7-diazaspiro[4.4]nonan-2-one;
1-{4-[(2S)-2,3-dihydro-1,4-benzodioxin-2-yl]benzyl}piperidine-4-carboxylic acid;
(1-{4-[(2S)-2,3-dihydro-1,4-benzodioxin-2-yl]benzyl}piperidin-4-yl)(morpholin-4-yl)methanone;
8-{4-[(3S)-2,3-dihydro[1,4]dioxino[2,3-b]pyridin-3-yl]benzyl}-1,3,8-triazaspiro[4.5]decane-2,4-dione;
(3S)-3-{4-[(3-methoxypiperidin-1-yl)methyl]phenyl}-2,3-dihydro[1,4]dioxino[2,3-b]pyridine;
N-(1-{4-[(2S)-2,3-dihydro-1,4-benzodioxin-2-yl]benzyl}pyrrolidin-3-yl)-N-methylacetamide;
1-{4-[(2S)-2,3-dihydro-1,4-benzodioxin-2-yl]benzyl}-4-(1,1-dioxido-1,2-thiazolidin-2-yl)piperidine;
(3R)-1-{4-[(3S)-2,3-dihydro[1,4]dioxino[2,3-b]pyridin-3-yl]benzyl}pyrrolidin-3-ol;
N-(1-{4-[(3S)-2,3-dihydro[1,4]dioxino[2,3-b]pyridin-3-yl]benzyl}piperidin-4-yl)-2-hydroxyacetamide;
4-[(1-{4-[(3S)-2,3-dihydro[1,4]dioxino[2,3-b]pyridin-3-yl]benzyl}piperidin-4-yl)methyl]benzoic acid;
(1-{4-[(3S)-2,3-dihydro[1,4]dioxino[2,3-b]pyridin-3-yl]benzyl}piperidin-4-yl)(morpholin-4-yl)methanone;

(3S)-3-[4-(morpholin-4-ylmethyl)phenyl]-2,3-dihydro[1,4]dioxino[2,3-b]pyridine;

8-{4-[(2S)-2,3-dihydro-1,4-benzodioxin-2-yl]benzyl}-2,8-diazaspiro[4.5]decan-1-one;

1-{4-[(3S)-2,3-dihydro[1,4]dioxino[2,3-b]pyridin-3-yl]benzyl}piperidine-4-carbonitrile;

1-{4-[(2S)-2,3-dihydro-1,4-benzodioxin-2-yl]benzyl}-N-methylpiperidine-4-carboxamide;

8-{4-[(3S)-2,3-dihydro[1,4]dioxino[2,3-b]pyridin-3-yl]benzyl}-2,8-diazaspiro[4.5]decan-1-one;

N-(1-{4-[(3S)-2,3-dihydro[1,4]dioxino[2,3-b]pyridin-3-yl]benzyl}piperidin-4-yl)-2-hydroxy-2-methylpropanamide;

N-(1-{4-[(3S)-2,3-dihydro[1,4]dioxino[2,3-b]pyridin-3-yl]benzyl}piperidin-4-yl)-1-hydroxycyclopropanecarboxamide;

N-{4-[(2S)-2,3-dihydro-1,4-benzodioxin-2-yl]benzyl}-N-ethylcyclopentanamine;

1-{4-[(3S)-2,3-dihydro[1,4]dioxino[2,3-b]pyridin-3-yl]benzyl}-N-methylpiperidine-4-carboxamide;

N-{4-[(3S)-2,3-dihydro[1,4]dioxino[2,3-b]pyridin-3-yl]benzyl}-N-methylcyclopentanamine;

1-[(1-{4-[(3S)-2,3-dihydro[1,4]dioxino[2,3-b]pyridin-3-yl]benzyl}piperidin-3-yl)methyl]pyrrolidin-2-one;

1-{4-[(2S)-2,3-dihydro-1,4-benzodioxin-2-yl]benzyl}-2-methylpyrrolidine;

N-{4-[(3S)-2,3-dihydro[1,4]dioxino[2,3-b]pyridin-3-yl]benzyl}-2-methyl-1-(pyrrolidin-1-yl)propan-2-amine;

N-cyclohexyl-N-{4-[(2S)-2,3-dihydro-1,4-benzodioxin-2-yl]benzyl}-N',N'-dimethylethane-1,2-diamine;

N-(1-{4-[(3S)-2,3-dihydro[1,4]dioxino[2,3-b]pyridin-3-yl]benzyl}piperidin-4-yl)acetamide;

N-{4-[(3S)-2,3-dihydro[1,4]dioxino[2,3-b]pyridin-3-yl]benzyl}-N-methyl-2-(pyridin-2-yl)ethanamine;

(3S)-3-[4-(pyrrolidin-1-ylmethyl)phenyl]-2,3-dihydro[1,4]dioxino[2,3-b]pyridine;

1-{4-[(3S)-2,3-dihydro[1,4]dioxino[2,3-b]pyridin-3-yl]benzyl}piperidine-3-carboxamide;

1-{4-[(3S)-2,3-dihydro[1,4]dioxino[2,3-b]pyridin-3-yl]benzyl}piperidine-4-carboxamide;

N-(1-{4-[(2S)-2,3-dihydro-1,4-benzodioxin-2-yl]benzyl}pyrrolidin-3-yl)acetamide;

1-{4-[(3S)-2,3-dihydro[1,4]dioxino[2,3-b]pyridin-3-yl]benzyl}-N-(2-hydroxyethyl)piperidine-4-carboxamide;

(3S)-3-[4-(1,4-oxazepan-4-ylmethyl)phenyl]-2,3-dihydro[1,4]dioxino[2,3-b]pyridine;

1-{4-[(2S)-2,3-dihydro-1,4-benzodioxin-2-yl]benzyl}-N-(2-hydroxyethyl)piperidine-4-carboxamide;

4-(1-{4-[(2S)-2,3-dihydro-1,4-benzodioxin-2-yl]benzyl}piperidin-4-yl)benzoic acid;

1-(1-{4-[(2S)-2,3-dihydro-1,4-benzodioxin-2-yl]benzyl}piperidin-4-yl)urea;

7-{4-[(2S)-2,3-dihydro-1,4-benzodioxin-2-yl]benzyl}-1,7-diazaspiro[4.4]nonan-2-one;

8-{4-[(3S)-2,3-dihydro[1,4]dioxino[2,3-b]pyridin-3-yl]benzyl}-2-methyl-2,8-diazaspiro[4.5]decan-1-one;

1-{4-[(3S)-2,3-dihydro[1,4]dioxino[2,3-b]pyridin-3-yl]benzyl}piperidin-4-ol;

N-(1-{4-[(2S)-2,3-dihydro-1,4-benzodioxin-2-yl]benzyl}piperidin-4-yl)methanesulfonamide;

3-(1-{4-[(3S)-2,3-dihydro[1,4]dioxino[2,3-b]pyridin-3-yl]benzyl}piperidin-4-yl)propan-1-ol;

(3S)-3-{4-[(4-methylpiperidin-1-yl)methyl]phenyl}-2,3-dihydro[1,4]dioxino[2,3-b]pyridine;

N-{4-[(3S)-2,3-dihydro[1,4]dioxino[2,3-b]pyridin-3-yl]benzyl}-N-ethylethanamine;

N-{4-[(3S)-2,3-dihydro[1,4]dioxino[2,3-b]pyridin-3-yl]benzyl}-1-(methylsulfonyl)piperidin-4-amine;

(3S)-3-{4-[(4-fluoropiperidin-1-yl)methyl]phenyl}-2,3-dihydro[1,4]dioxino[2,3-b]pyridine;

1-(4-{4-[(3S)-2,3-dihydro[1,4]dioxino[2,3-b]pyridin-3-yl]benzyl}-1,4-diazepan-1-yl)ethanone;

[(3R)-1-{4-[(2S)-2,3-dihydro-1,4-benzodioxin-2-yl]benzyl}piperidin-3-yl]acetic acid;

(1-{4-[(3S)-2,3-dihydro[1,4]dioxino[2,3-b]pyridin-3-yl]benzyl}piperidin-4-yl)-methanol;

4-[(1-{4-[(2S)-2,3-dihydro-1,4-benzodioxin-2-yl]benzyl}piperidin-4-yl)methyl]benzoic acid;

(3S)-3-{4-[(4-methyl-1,4-diazepan-1-yl)methyl]phenyl}-2,3-dihydro[1,4]dioxino[2,3-b]pyridine;

(3S)-3-{4-[(3-methoxypyrrolidin-1-yl)methyl]phenyl}-2,3-dihydro[1,4]dioxino[2,3-b]pyridine; and N-[4-[(2S)-2,3-dihydro-1,4-benzodioxin-2-yl]benzyl]-N,2-dimethylpropan-2-amine; or a pharmaceutically salt thereof of each of the foregoing.

In another embodiment, the invention relates to a compound selected from the group consisting of:

(3S)-3-[4-(azepan-1-ylmethyl)phenyl]-2,3-dihydro[1,4]dioxino[2,3-b]pyridine;

N-{4-[(3S)-2,3-dihydro[1,4]dioxino[2,3-b]pyridin-3-yl]benzyl}-N-methylcyclopentanamine;

N-(1-{4-[(3S)-2,3-dihydro[1,4]dioxino[2,3-b]pyridin-3-yl]benzyl}piperidin-4-yl)methanesulfonamide;

(3S)-3-{4-[(3-methoxypiperidin-1-yl)methyl]phenyl}-2,3-dihydro[1,4]dioxino[2,3-b]pyridine;

(3S)-3-{4-[(4-methylpiperidin-1-yl)methyl]phenyl}-2,3-dihydro[1,4]dioxino[2,3-b]pyridine;

N-(1-{4-[(3S)-2,3-dihydro[1,4]dioxino[2,3-b]pyridin-3-yl]benzyl}piperidin-4-yl)acetamide;

(3S)-3-{4-[(1s,4s)-7-azabicyclo[2.2.1]hept-7-ylmethyl]phenyl}-2,3-dihydro[1,4]dioxino[2,3-b]pyridine;

(3S)-3-[4-(pyrrolidin-1-ylmethyl)phenyl]-2,3-dihydro[1,4]dioxino[2,3-b]pyridine;

N-{4-[(3S)-2,3-dihydro[1,4]dioxino[2,3-b]pyridin-3-yl]benzyl}-N-ethylethanamine;

N-(1-{4-[(2S)-2,3-dihydro-1,4-benzodioxin-2-yl]benzyl}pyrrolidin-3-yl)-N-methylacetamide;

N-{4-[(3S)-2,3-dihydro[1,4]dioxino[2,3-b]pyridin-3-yl]benzyl}-2-methyl-1-(pyrrolidin-1-yl)propan-2-amine;

1-{4-[(3S)-2,3-dihydro[1,4]dioxino[2,3-b]pyridin-3-yl]benzyl}piperidin-4-ol;

8-{4-[(3S)-2,3-dihydro[1,4]dioxino[2,3-b]pyridin-3-yl]benzyl}-2,8-diazaspiro[4.5]decan-1-one;

(1-{4-[(3S)-2,3-dihydro[1,4]dioxino[2,3-b]pyridin-3-yl]benzyl}piperidin-4-yl)(morpholin-4-yl)methanone;

N-(1-{4-[(2S)-2,3-dihydro-1,4-benzodioxin-2-yl]benzyl}pyrrolidin-3-yl)acetamide;

1-{4-[(3S)-2,3-dihydro[1,4]dioxino[2,3-b]pyridin-3-yl]benzyl}-N-methylpiperidine-4-carboxamide;

7-{4-[(3S)-2,3-dihydro[1,4]dioxino[2,3-b]pyridin-3-yl]benzyl}-1,7-diazaspiro[4.4]nonan-2-one;

(3S)-3-[4-(1,4-oxazepan-4-ylmethyl)phenyl]-2,3-dihydro[1,4]dioxino[2,3-b]pyridine;

3-(1-{4-[(3S)-2,3-dihydro[1,4]dioxino[2,3-b]pyridin-3-yl]benzyl}piperidin-4-yl)propan-1-ol;

8-{4-[(3S)-2,3-dihydro[1,4]dioxino[2,3-b]pyridin-3-yl]benzyl}-2-methyl-2,8-diazaspiro[4.5]decan-1-one;

(3S)-3-{4-[(4-methyl-1,4-diazepan-1-yl)-methyl]phenyl}-2,3-dihydro[1,4]dioxino[2,3-b]pyridine;

4-(1-{4-[(2S)-2,3-dihydro-1,4-benzodioxin-2-yl]benzyl}piperidin-4-yl)benzoic acid;

(3R)-1-{4-[(3S)-2,3-dihydro[1,4]dioxino[2,3-b]pyridin-3-yl]benzyl}pyrrolidin-3-ol;

1-(4-{4-[(3S)-2,3-dihydro[1,4]dioxino[2,3-b]pyridin-3-yl]benzyl}-1,4-diazepan-1-yl)ethanone;

1-{4-[(3S)-2,3-dihydro[1,4]dioxino[2,3-b]pyridin-3-yl]benzyl}piperidine-4-carbonitrile;
N-(1-{4-[(3S)-2,3-dihydro[1,4]dioxino[2,3-b]pyridin-3-yl]benzyl}piperidin-4-yl)-2-hydroxy-2-methylpropanamide;
1-{4-[(3S)-2,3-dihydro[1,4]dioxino[2,3-b]pyridin-3-yl]benzyl}piperidine-3-carboxamide;
(1-{4-[(3S)-2,3-dihydro[1,4]dioxino[2,3-b]pyridin-3-yl]benzyl}piperidin-4-yl)-methanol;
8-{4-[(3S)-2,3-dihydro[1,4]dioxino[2,3-b]pyridin-3-yl]benzyl}-1,3,8-triazaspiro[4.5]decane-2,4-dione;
N-(1-{4-[(3S)-2,3-dihydro[1,4]dioxino[2,3-b]pyridin-3-yl]benzyl}piperidin-4-yl)-1-hydroxycyclopropanecarboxamide;
1-{4-[(2S)-2,3-dihydro-1,4-benzodioxin-2-yl]benzyl}-N-(2-hydroxyethyl)piperidine-4-carboxamide;
N-{4-[(3S)-2,3-dihydro[1,4]dioxino[2,3-b]pyridin-3-yl]benzyl}-1-(methylsulfonyl)piperidin-4-amine;
1-{4-[(3S)-2,3-dihydro[1,4]dioxino[2,3-b]pyridin-3-yl]benzyl}piperidine-4-carboxamide;
4-(1-{4-[(3S)-2,3-dihydro[1,4]dioxino[2,3-b]pyridin-3-yl]benzyl}piperidin-4-yl)benzoic acid;
1-{4-[(2S)-2,3-dihydro-1,4-benzodioxin-2-yl]benzyl}-2-methylpyrrolidine;
1-[(1-{4-[(3S)-2,3-dihydro[1,4]dioxino[2,3-b]pyridin-3-yl]benzyl}piperidin-3-yl)methyl]pyrrolidin-2-one;
7-{4-[(2S)-2,3-dihydro-1,4-benzodioxin-2-yl]benzyl}-1,7-diazaspiro[4.4]nonan-2-one;
1-(1-{4-[(2S)-2,3-dihydro-1,4-benzodioxin-2-yl]benzyl}piperidin-4-yl)urea;
N-{4-[(2S)-2,3-dihydro-1,4-benzodioxin-2-yl]benzyl}-N-ethylcyclopentanamine;
N-{4-[(3S)-2,3-dihydro[1,4]dioxino[2,3-b]pyridin-3-yl]benzyl}-N-methyl-2-(pyridin-2-yl)ethanamine;
1-{4-[(2S)-2,3-dihydro-1,4-benzodioxin-2-yl]benzyl}-2-methylpiperidine;
1-{4-[(2S)-2,3-dihydro-1,4-benzodioxin-2-yl]benzyl}piperidine-4-carboxylic acid;
4-[(1-{4-[(3S)-2,3-dihydro[1,4]dioxino[2,3-b]pyridin-3-yl]benzyl}piperidin-4-yl)methyl]benzoic acid;
(3S)-3-[4-(morpholin-4-ylmethyl)phenyl]-2,3-dihydro[1,4]dioxino[2,3-b]pyridine;
(3S)-3-{4-[(4-fluoropiperidin-1-yl)methyl]phenyl}-2,3-dihydro[1,4]dioxino[2,3-b]pyridine;
(1-{4-[(2S)-2,3-dihydro-1,4-benzodioxin-2-yl]benzyl}piperidin-4-yl)(morpholin-4-yl)methanone;
8-{4-[(2S)-2,3-dihydro-1,4-benzodioxin-2-yl]benzyl}-2,8-diazaspiro[4.5]decan-1-one;
N-(1-{4-[(3S)-2,3-dihydro[1,4]dioxino[2,3-b]pyridin-3-yl]benzyl}piperidin-4-yl)-2-hydroxyacetamide;
4-[(1-{4-[(2S)-2,3-dihydro-1,4-benzodioxin-2-yl]benzyl}piperidin-4-yl)methyl]benzoic acid;
N-(1-{4-[(2S)-2,3-dihydro-1,4-benzodioxin-2-yl]benzyl}piperidin-4-yl)methanesulfonamide;
1-{4-[(2S)-2,3-dihydro-1,4-benzodioxin-2-yl]benzyl}-N-methylpiperidine-4-carboxamide;
4-(1-{4-[(2S)-2,3-dihydro-1,4-benzodioxin-2-yl]benzyl}piperidin-4-yl)butanoic acid;
7-{4-[(2S)-2,3-dihydro-1,4-benzodioxin-2-yl]benzyl}-1,7-diazaspiro[4.4]nonane-1-carboxamide;
N-cyclohexyl-N-{4-[(2S)-2,3-dihydro-1,4-benzodioxin-2-yl]benzyl}-N',N'-dimethylethane-1,2-diamine;
[(3R)-1-{4-[(2S)-2,3-dihydro-1,4-benzodioxin-2-yl]benzyl}piperidin-3-yl]acetic acid;
1-{4-[(2S)-2,3-dihydro-1,4-benzodioxin-2-yl]benzyl}-4-(1,1-dioxido-1,2-thiazolidin-2-yl)piperidine; and
1-{4-[(3S)-2,3-dihydro[1,4]dioxino[2,3-b]pyridin-3-yl]benzyl}-N-(2-hydroxyethyl)piperidine-4-carboxamide; or
a pharmaceutically acceptable salt thereof of each of the foregoing.

In another embodiment, the invention relates a pharmaceutical composition comprising one or more compounds of formula (I) as defined in any of the embodiments above, or a pharmaceutically acceptable salt thereof, and a pharmaceutically acceptable carrier or excipient.

All terms as used herein in this specification, unless otherwise stated, shall be understood in their ordinary meaning as known in the art. Other more specific definitions are as follows:

The term "$(C_1-C_6)$alkyl" refers to branched and unbranched alkyl groups having from 1 to 6 carbon atoms. Examples of —$(C_1-C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1-C_6)$alkyl group can be the point of attachment to another group or moiety.

The term "$(C_3-C_6)$cycloalkyl" refers to a nonaromatic 3- to 6-membered monocyclic carbocyclic radical. Examples of "$(C_3-C_6)$cycloalkyls" include cyclopropyl, cyclobutyl, cyclohexyl, cyclopentyl and cyclohexyl.

As used herein, the term "$(C_6-C_{10})$aryl" refers to an aromatic hydrocarbon rings containing from six to ten carbon ring and includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "4 to 11-membered heterocycle" includes stable nonaromatic 4 to 8-membered monocyclic heterocyclic radical or a stable nonaromatic 6 to 11-membered fused bicyclic, bridged bicyclic or spirocyclic heterocyclic radical. The 4 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4- to 8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. As used herein, the term "5 to 11-membered heteroaryl" includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocyclyl or heteroaryl contains a S ring atom, such S ring atom can be present in the ring in its divalent, tetravalent, or hexavalent form, i.e., —S—, —S(O)— or S(O)₂—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S.

The term "halo" or "halogen" refers to fluoro, chloro, bromo or iodo.

The symbol

means point of attachment of a group R to a moiety.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms to or internal carbon atoms within a branched or unbranched carbon chain. Such groups can be substituted as herein above described by groups such as oxo to result in definitions such as but not limited to: alkoxycarbonyl, acyl, amido and thioxo.

For all compounds disclosed in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The compounds of the invention are only those which are contemplated to be 'chemically stable' as will be appreciated by those skilled in the art. For example, a compound which would have a 'dangling valency', or a 'carbanion' is not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$)alkyl)$^{4+}$ salts.

In addition, within the scope of the invention is use of prodrugs of compounds of the to invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the general methods, examples presented below, and methods known to those of ordinary skill in the art and reported in the chemical literature. In each of the schemes below, the groups $R^1$ to $R^3$ and A are as defined above for the compound of formula (I), unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section.

Scheme 1 below depicts the general synthetic procedure for making the compounds of formula (I) wherein X is CH ("the benzodioxane LTAH₄ inhibitors").

Scheme 1: General synthetic scheme for making benzodioxane LTA4H inhibitors

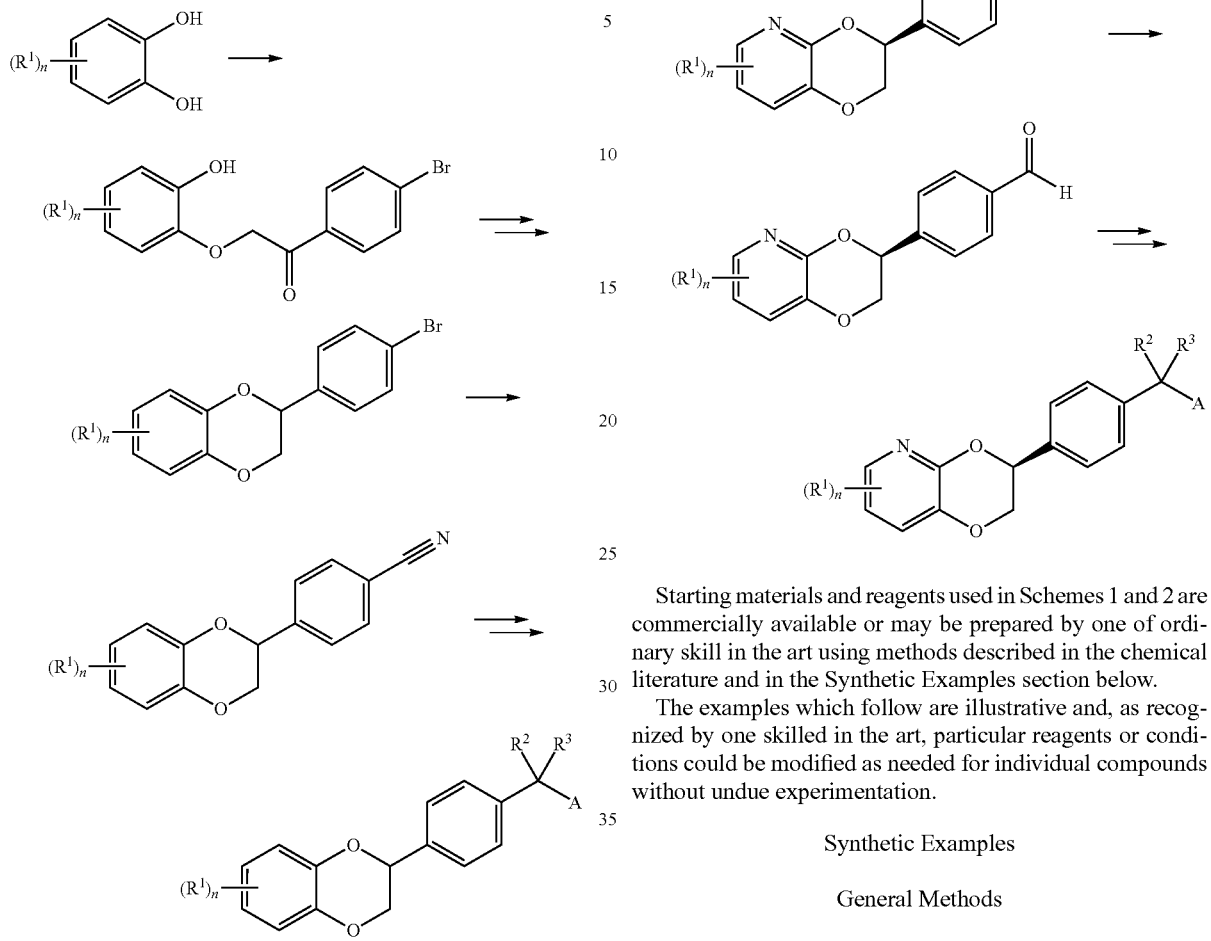

Scheme 2 below depicts the general synthetic procedure for making the compounds of formula (I) wherein X is N ("the 8-azabenzodioxane LTAH4 inhibitors").

Scheme 2: General synthetic scheme for 8-azabenzodioxane LTA4H inhibitors

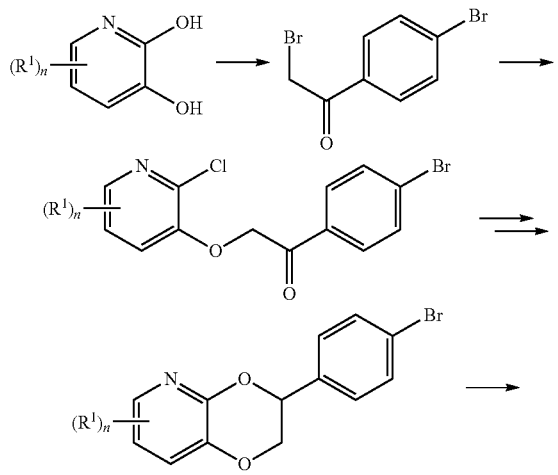

Starting materials and reagents used in Schemes 1 and 2 are commercially available or may be prepared by one of ordinary skill in the art using methods described in the chemical literature and in the Synthetic Examples section below.

The examples which follow are illustrative and, as recognized by one skilled in the art, particular reagents or conditions could be modified as needed for individual compounds without undue experimentation.

Synthetic Examples

General Methods

Unless noted otherwise, all reactions are run at room temperature (about 25° C.), under inert atmosphere (e.g., Argon, $N_2$), and under anhydrous conditions. All compounds are characterized by at least one of the following methods: $^1$H NMR, HPLC, HPLC-MS, and melting point.

Typically, reaction progress is monitored by thin layer chromatography (TLC) or HPLC-MS. Intermediates and products are purified using at least one of the following methods:

Flash chromatography on silica gel,
Recrystallization,
Chiral HPLC using a 20×500 mm Chiralpak AD-H column, or 20×500 mm
Chiralpak OD-H column, and eluting with an isocratic mixture of isopropanol in heptanes with 0.1% diethylamine (DEA) at 7.5 mL/min,
20×250 mm Chiralcel OD-H column, and eluting with an isocratic mixture of isopropanol in heptanes at 7.5 mL/min,
Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or
Reversed phase HPLC using a C18 semi-preparative column eluting with a gradient of MeCN+0.1% TFA/H$_2$O+0.1% TFA, or MeCN+0.1% formic acid/H$_2$O+0.1% formic acid.

The reported MS data is for observed [M+H]$^+$. For bromine containing compounds, the [M+H]$^+$ is either reported for one or both of the bromine isotopes (i.e., $^{79}$Br and $^{81}$Br).

LC/MS methods used in to characterize and isolate the compounds of the inventions are described in Tables 2a and 2b below.

TABLE 2a

LC/MS Methods and retention times (RT).

| LC/MS Method | Time (min) | Mobile Phase H$_2$O (0.1% FA) | CH$_3$CN (0.1% FA) | Flow (mL/min) | Column |
|---|---|---|---|---|---|
| 1 | 0 | 95 | 5 | 2.5 | Agilent Zorbax C18 |
|  | 1.7 | 5 | 95 | 2.5 | SB 3.5 um 4.6 × |
|  | 2 | 5 | 95 | 2.5 | 30 mm cartridge |
|  | 2.1 | 95 | 5 | 2.5 |  |
|  | 2.3 | 95 | 5 | 2.5 |  |
| 2 | 0 | 70 | 30 | 2.5 | Agilent Zorbax C18 |
|  | 1.7 | 5 | 95 | 2.5 | SB 3.5 um 4.6 × |
|  | 2 | 5 | 95 | 2.5 | 30 mm cartridge |
|  | 2.1 | 70 | 30 | 2.5 |  |
|  | 2.3 | 70 | 30 | 2.5 |  |
| 3 | 0 | 99 | 1 | 2.5 | Agilent Zorbax C18 |
|  | 1.7 | 50 | 50 | 2.5 | SB 3.5 um 4.6 × |
|  | 2 | 5 | 95 | 2.5 | 30 mm cartridge |
|  | 2.1 | 5 | 95 | 2.5 |  |
|  | 2.3 | 99 | 1 | 2.5 |  |
| 4 | 0 | 95 | 5 | 1.5 | Agilent Zorbax Eclipse |
|  | 7 | 5 | 95 | 1.5 | XDB-C8 5 um 4.6 × |
|  | 9 | 5 | 95 | 1.5 | 150 mm |
|  | 9.3 | 95 | 5 | 1.5 |  |
|  | 10 | 95 | 5 | 1.5 |  |
| 5 | 0 | 99 | 1 | 2.5 | Agilent Zorbax C18 |
|  | 1.6 | 80 | 20 | 2.5 | SB 3.5 um 4.6 × |
|  | 1.7 | 5 | 95 | 2.5 | 30 mm cartridge |
|  | 2 | 5 | 95 | 2.5 |  |
|  | 2.1 | 99 | 1 | 2.5 |  |
|  | 2.3 | 99 | 1 | 2.5 |  |
| 6 | 0 | 99 | 1 | 1.5 | Agilent Zorbax Eclipse |
|  | 2 | 80 | 20 | 1.5 | XDB-C8 5 um 4.6 × |
|  | 7 | 5 | 95 | 1.5 | 150 mm column |
|  | 9 | 5 | 95 | 1.5 |  |
|  | 9.3 | 99 | 1 | 1.5 |  |
|  | 10 | 99 | 1 | 1.5 |  |
| 7 | 0 | 88 | 12 | 1.5 | Agilent SB-C18 1.8 um |
|  | 0.25 | 70 | 30 | 1.5 | 3 × 50 mm column |
|  | 0.3 | 60 | 40 | 1.5 |  |
|  | 1.19 | 5 | 95 | 1.5 |  |
|  | 1.75 | 0 | 100 | 1.5 |  |
| 8 | 0 | 60 | 40 | 1.5 | Agilent Eclipse C8 1.8 |
|  | 1.19 | 15 | 85 | 1.5 | um 3 × 50 mm column |
|  | 1.75 | 0 | 100 | 1.5 |  |
| 9 | 0 | 95 | 5 | 1.5 | Agilent SB-AQ 1.8 um |
|  | 0.25 | 50 | 50 | 1.5 | 3 × 50 mm column |
|  | 0.3 | 70 | 30 | 1.5 |  |
|  | 1.3 | 10 | 90 | 1.5 |  |
|  | 1.7 | 0 | 100 | 1.5 |  |
| 10 | 0 | 95 | 5 | 1.5 | Agilent SB-C18 1.8 um |
|  | 3.8 | 10 | 90 | 1.5 | 3 × 50 mm column |
|  | 4.5 | 0 | 100 | 1.5 |  |

TABLE 2b

LC/MS Methods and retention times (RT).

| LC/MS Method | Time (min) | Mobile Phase 95% H$_2$O 2 + 5% CH$_3$CN (0.05% Formic Acid) | CH$_3$CN (0.05% Formic Acid) | Flow (mL/min) | Column |
|---|---|---|---|---|---|
| 11 | 0 | 90 | 10 | 0.8 | BEH 2.1 × 50 |
|  | 1.19 | 5 | 95 | 0.8 | mm C18, 1.7 um |
|  | 1.7 | 5 | 95 | 0.8 | particle diameter |
| 12 | 0 | 90 | 10 | 0.8 | BEH 2.1 × 50 |
|  | 1.19 | 0 | 100 | 0.8 | mm C18, 1.7 um |
|  | 1.7 | 0 | 100 | 0.8 | particle diameter |
| 13 | 0 | 95 | 5 | 0.6 | Waters HSS T3 |
|  | 4.45 | 0 | 100 | 0.6 | 2.1 × 100 mm |
|  | 5 | 0 | 100 | 0.6 | 18 um column |
| 14 | 0 | 100 | 0 | 0.6 | Waters HSS T3 |
|  | 1 | 100 | 0 | 0.6 | 2.1 × 100 mm |
|  | 4.45 | 0 | 100 | 0.6 | 18 um column |
|  | 5 | 0 | 100 |  |  |
| 15 | 0 | 90 | 10 | 0.6 | BEH 2.1 × 50 |
|  | 4.45 | 0 | 100 | 0.6 | mm C18, 1.7 um |
|  | 4.58 | 0 | 100 | 0.6 | particle diameter |

Synthesis of Intermediates

Preparation of (S)-4-(2,3-Dihydro-benzo[1,4]dioxin-2-yl)-benzaldehyde (A)

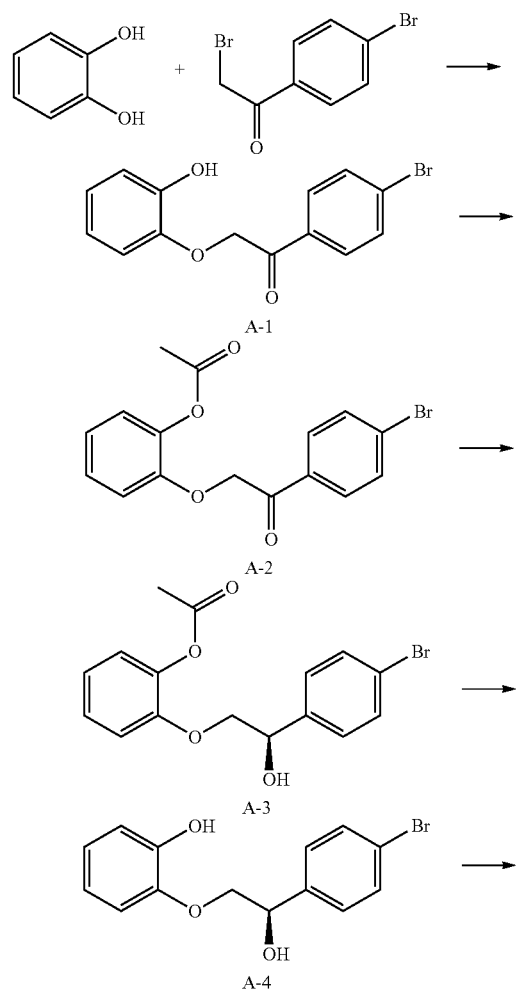

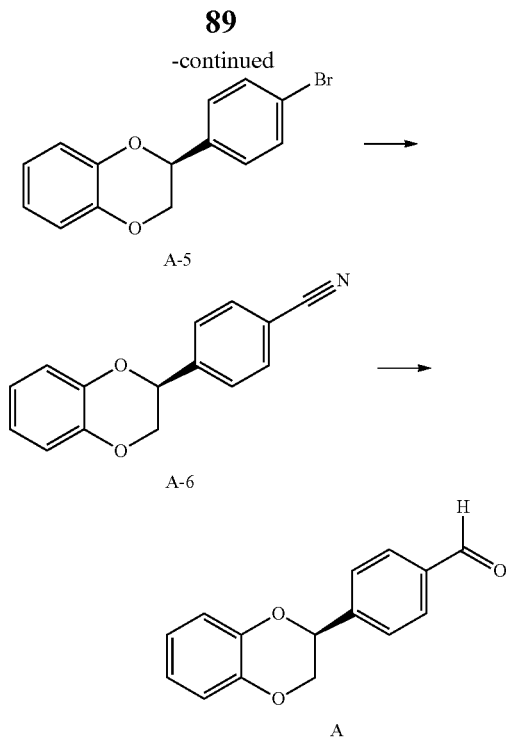

To a stirred solution of pyrocatechol (23.8 g, 216 mmol) in acetone (300 mL) is added cesium carbonate (84.4 g, 259 mmol) and 2-Bromo-1-(4-bromo-phenyl)-ethanone (60 g, 216 mmol) at room temperature. The reaction is stirred at room temperature for 1 hour then water (200 mL) is added. The precipitate is filtered and triturated with EtOAc (150 mL) to give A-1 as a solid.

To a solution of A-1 (50.0 g, 163 mmol) in anhydrous THF (375 mL) is added acetic anhydride (23.0 mL, 244 mmol), TEA (34.0 mL, 244 mmol), and DMAP (199 mg, 1.63 mmol). The reaction mixture is stirred at 40° C. for 45 min, cooled to room temperature and diluted with EtOAc (250 mL). The organic solution is washed with water (2×100 mL), 0.25N HCl (100 mL), saturated sodium bicarbonate solution (100 mL), and brine (100 mL), and dried over $Na_2SO_4$. After removal of volatile solvent, the residue is triturated with 5% EtOAc in heptane (1500 mL). The solid is filtered and air dried to give A-2. To degassed DMF (500 mL) is added A-2 (41.0 g, 117 mmol), (1S,2S)-(+)-N-(4-Toluenesulfonyl)-1,2-diphenylethylenediamine (756 mg, 2.10 mmol) and Pentamethylcyclopentadienylrhodium(III)dichloride (Cp*RhCl$_2$) dimer (319 mg, 0.520 mmol). The resulting mixture is stirred at 0° C. for 20 minutes under argon sparging and treated dropwise with formic acid/triethylamine complex (5:2, 31 mL, 72 mmol). The reaction mixture is stirred under argon at 0° C. for 2 hours, diluted with EtOAc (600 mL), and washed with half-saturated sodium bicarbonate solution, saturated sodium bicarbonate, and brine. The organic layer is dried over $Na_2SO_4$ and concentrated. The residue is purified through a pad of silica gel (400 mL), eluting with EtOAc/heptane (1:1, 3 L) to give A-3 as a solid.

To a MeOH solution (125 mL) of A-3 (24.6 g, 69.0 mmol) is added a solution of LiOH.H$_2$O (5.8 g, 137 mmol) in water (125 mL). The mixture is stirred at 60° C. for 30 min, cooled to room temperature and concentrated. The residue is diluted with water and neutralized with 1N aqueous HCl to a pH of 6. The resulting mixture is extracted with EtOAc (3×150 mL). The combined organic extracts are washed by saturated sodium bicarbonate solution, brine, dried over $Na_2SO_4$, filtered and concentrated to give A-4 as an oil.

To a 0° C. solution of triphenylphosphine (32.7 g, 125 mmol) and diisopropyl azodicarboxylate (24.7 mL, 125 mmol) in THF (anhydrous, 400 mL) is added a solution of A-4 (35 g, 113 mmol) in THF (anhydrous, 200 mL) over 30 min. The resulting solution is warmed to room temperature, stirred for 1 hour, and concentrated. The residue is vigorously stirred in heptane (1.8 L) for 2 hours. The precipitate is filtered, and rinsed with heptane. The filtrate is concentrated and purified by flash column chromatography on silica gel (0-10% EtOAc in heptane) to give A-5 as a solid.

To an argon-degassed solution of A-5 (30.7 g, 105 mmol) in DMF (anhydrous, 400 mL) is added Zn(CN)$_2$ (12.4 g, 105 mmol), tris(dibenzylideneacetone)dipalladium(0) (Pd$_2$(dba)$_3$) (2.9 g, 3.2 mmol), and 1,1'-bis(diphenylphosphino)ferrocene (dppf) (3.5 g, 6.3 mmol). The resulting mixture is sparged with argon and stirred at 80° C. overnight. The reaction is cooled to room temperature and filtered through a pad of Diatomaceous earth, and rinsed with EtOAc. The filtrate is diluted with water (400 mL) and extracted with EtOAc (2×400 mL). The combined organic extracts are washed with brine and stirred with activated carbon (80 g). After 30 min, the mixture is filtered through a pad of Diatomaceous earth and concentrated. The residue is triturated with 2% EtOAc in heptane (1 L), and filtered to give A-6 as a solid.

A solution of A-6 (11.1 g, 46.7 mmol) in THF (anhydrous, 400 mL) at 0° C. is treated dropwise with DIBAL-H (25 wt % in toluene, 77.8 mL, 117 mmol). The reaction is stirred at 0° C. for 30 min, warmed to room temperature and stirred for 2 hours. The reaction is cooled down to 0° C. and quenched with EtOAc (250 mL) followed by saturated potassium sodium tartrate solution (400 mL). The mixture is diluted with EtOAc (300 mL) and water (300 mL) and stirred for 30 min. The organic layer is separated and washed with water, 1N HCl solution, and brine, and dried over $Na_2SO_4$. After filtering through a pad of Diatomaceous earth, the filtrate is concentrated and purified by flash column chromatography on silica gel (0-30% EtOAc in heptane) to give the title product as a solid.

Preparation of (±)-4-(2,3-Dihydro-benzo[1,4]dioxin-2-yl)-benzaldehyde (B)

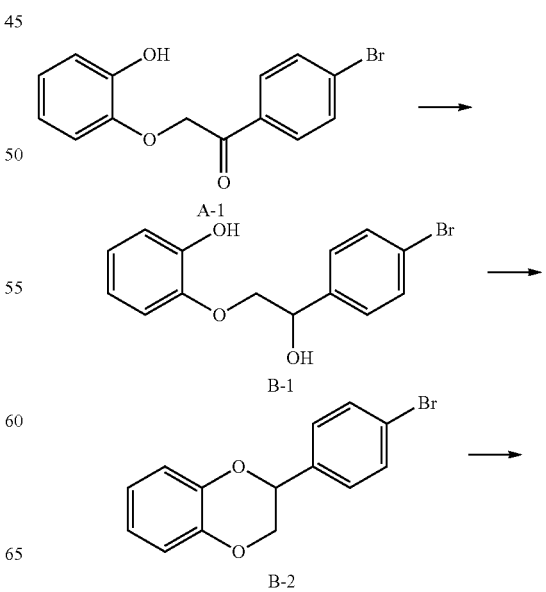

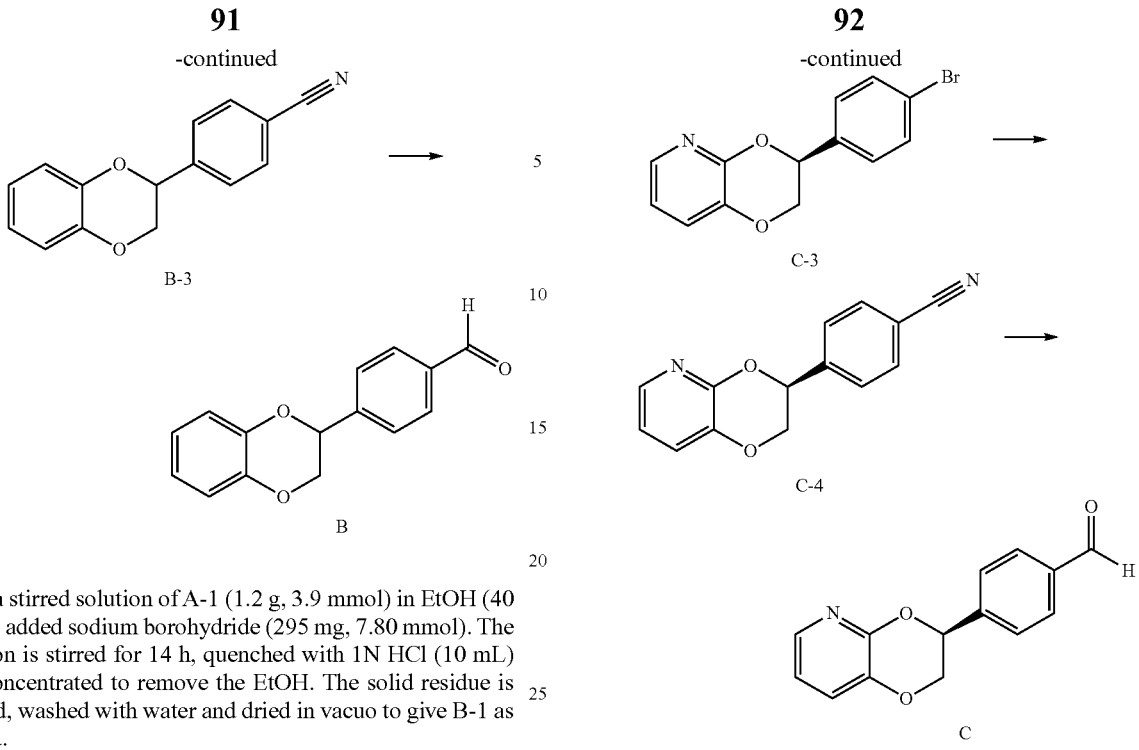

To a stirred solution of A-1 (1.2 g, 3.9 mmol) in EtOH (40 mL) is added sodium borohydride (295 mg, 7.80 mmol). The reaction is stirred for 14 h, quenched with 1N HCl (10 mL) and concentrated to remove the EtOH. The solid residue is filtered, washed with water and dried in vacuo to give B-1 as a solid.

The title product is synthesized from B-1 according to the procedure described for the synthesis of A from A-4.

Preparation of (S)-4-(2,3-Dihydro-[1,4]dioxino[2,3-b]pyridin-3-yl)-benzaldehyde (C)

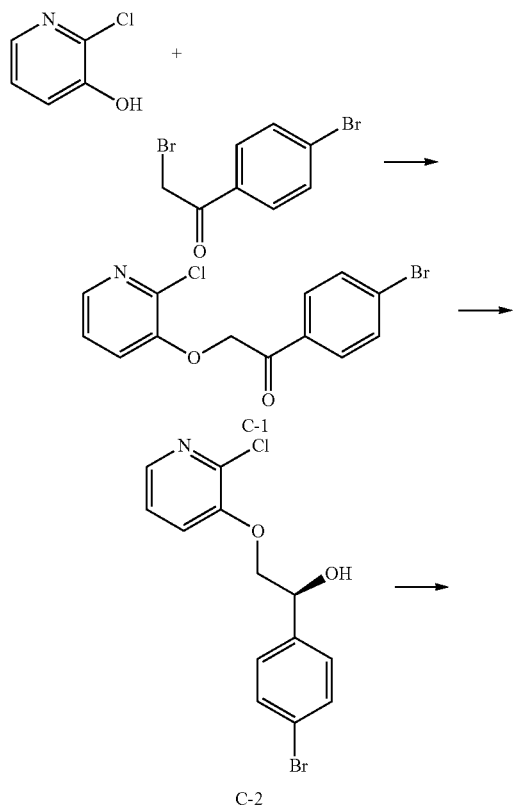

To a solution of 2-chloro-3-hydroxy-pyridine (25.0 g, 193 mmol) and 2,4'-dibromo-acetophenone (53.6 g, 193 mmol) in acetone (400 mL) is added $Cs_2CO_3$ (75.4 g, 232 mmol), and the suspension is stirred at room temperature for 1 h. The reaction is poured into 1 L of water with stirring. Filtration of the mixture gives C-1 as a solid.

A solution of C-1 (30.0 g, 91.9 mmol), Cp*RhCl₂ dimer (0.57 g, 0.92 mmol) and N-((1R,2R)-2-Amino-1,2-diphenyl-ethyl)-4-methyl-benzenesulfonamide (1.0 g, 2.8 mmol) in anhydrous DMF (400 mL) is cooled to 0° C. and sparged with argon for 20 minutes before the dropwise addition of formic acid: TEA mixture (5:2 mixture; 28.2 mL). The reaction is stirred at 0° C. with Argon sparging for 1 hr. The reaction mixture is slowly added to 1.5 L of vigorously stirred water. Filtration gives C-2 as a solid.

A solution of C-2 (10.0 g, 30.4 mmol) in DME (350 mL) is heated to 60° C., KHMDS (61.5 mL, 0.5M in toluene) is added slowly and the resulting solution is stirred for 30 minutes. The reaction is cooled to room temperature, quenched with water, concentrated in vacuo and extracted with EtOAc. The combined organics are washed with brine, dried over $Na_2SO_4$, filtered and concentrated. The residue is purified by flash column chromatography (0-40% EtOAc in heptanes) to give C-3 as a solid.

To a degassed solution of C-3 (5.50 g, 18.8 mmol) in anhydrous DMF (100 mL) is added $Zn(CN)_2$ (2.2 g, 18.8 mmol) and dppf (1.0 g, 1.9 mmol) followed by $Pd_2(dba)_3$ (0.86 g, 0.90 mmol), and the reaction is warmed to 80° C. overnight. The reaction is then cooled to room temperature and stirred for 48 h. The mixture is filtered through a bed of Diatomaceous earth, and the filtrate slowly poured into 1 L of vigorously stirred water.

The resulting solid is isolated by filtration and purified by flash chromatography on silica gel (0-40% EtOAc in heptanes) to give C-4 as a solid.

A solution of C-4 (3.5 g, 14.7 mmol) in 125 mL of THF is cooled down to 0° C. in a ice bath. 25 mL of 1.5M DIBAL-H (36.7 mmol, 2.5 eq) solution in toluene is added dropwise via addition funnel (over 15 min) The reaction is stirred at 0° C.

for 30 min and then allowed to warm to room temperature. The reaction mixture is stirred for 2 h at room temperature. The reaction is cooled to 0° C. and carefully quenched with EtOAc (200 mL total), followed by 100 mL of water and 400 mL of saturated aqueous Rochelle's salt solution, and the mixture is stirred for 5 minutes. The entire mixture is transferred to a separatory funnel and the layers are separated. The aqueous layer is extracted with 100 mL of EtOA twice, and the extracts are combined and washed with 0.5 N HCl (100 mL). Some product is observed in the acid layer. Acid layer is cooled to 0° C., neutralized with saturated $NaHCO_3$, and extracted with EtOAc twice. The organic layers are combined, washed with brine, and dried over anhydrous $Na_2SO_4$, and evaporated. The resulting residue is purified by flash chromatography eluting with 0-80% EtOAc/Heptane to give the title compound as a solid.

Preparation of (±)-4-(2,3-Dihydro-[1,4]dioxino[2,3-b]pyridin-3-yl)-benzaldehyde (D)

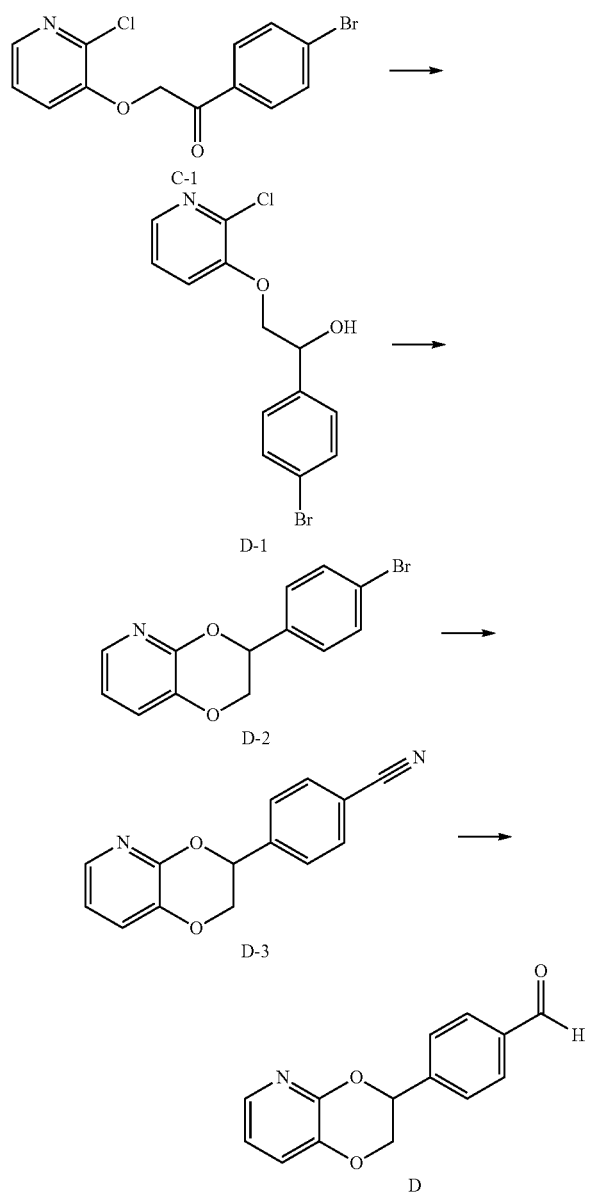

Compound D-1 is synthesized from C-1 according to the procedure described for the synthesis of B-1.

The title compound is synthesized from D-1 according to the procedure described for the synthesis of C from C-2.

Preparation of 2,2,2-trifluoro-1-piperidin-4-yl-ethanol (E)

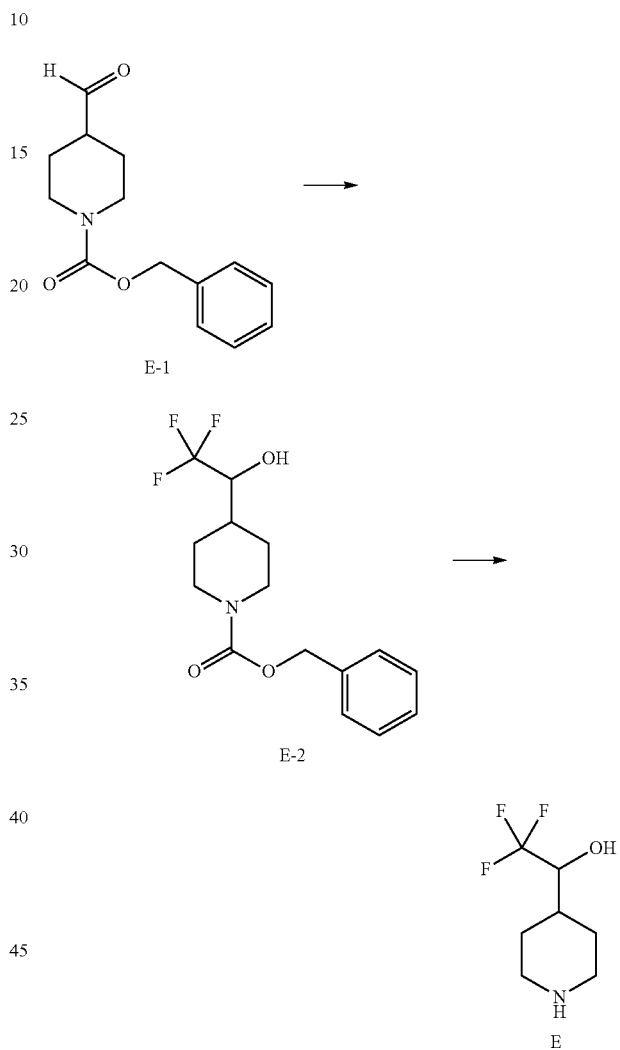

A solution of E-1 (500 mg, 2.00 mmol) and trimethyl (trifluoromethyl)silane ($TMSCF_3$) (863 mg, 6.00 mmol) in dry DMF (2 mL) is cooled to −25° C. and treated with 1,3-bis(1-adamantyl)imidazol-2-ylidene (3.4 mg, 0.010 mmol). The mixture is warmed to room temperature, stirred for 1 h, and treated with 2N HCl (2 mL). Upon completion, the mixture is neutralized with NaOH (5M, 0.7 mL), concentrated, and purified by reversed phase HPLC (10-90% $MeCN/H_2O$ gradient) to provide E-2 (LC/MS Method 1; RT=0.88 min.; ES+ m/z $[M+H]^+$ 318.2).

A mixture of E-2 (524 mg, 1.65 mmol) and 10% palladium on carbon (200 mg) in MeOH (16 mL) is stirred under an atmosphere of $H_2$ at room temperature for 15 h. The mixture is filtered through Diatomaceous earth, and the filter pad is washed with MeOH. The filtrate is concentrated to provide the title product.

Preparation of 1,1,1,3,3,3-Hexafluoro-2-piperidin-4-yl-propan-2-ol (F)

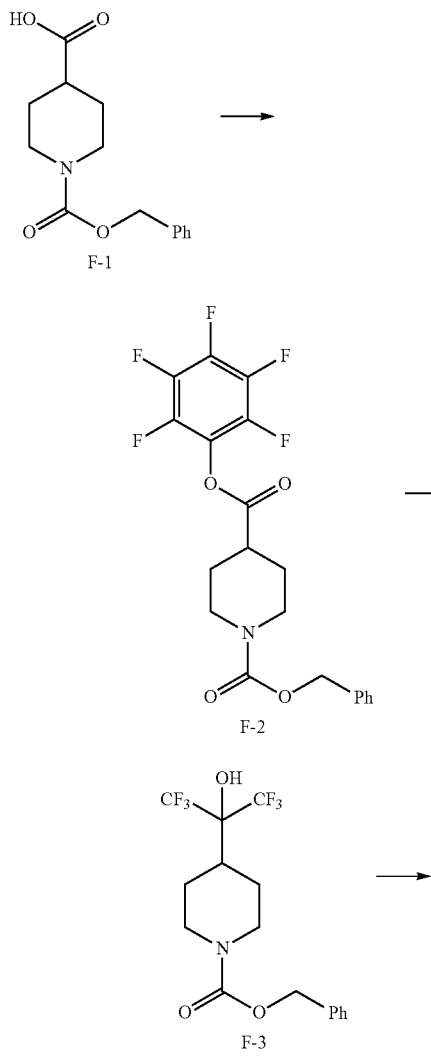

A solution of piperidine-1,4-dicarboxylic acid monobenzyl ester (1.0 g, 3.80 mmol), 2,3,4,5,6-pentafluoro-phenol (0.77 g, 4.18 mmol) and dicyclohexyl-carbodiimide (0.86 g, 4.18 mmol) in dioxane (12 mL) is stirred at room temperature for 16 h. The mixture is filtered and concentrated in vacuo. The residue is purified by flash chromatography (EtOAc/heptane) to give F-2.

To a solution of F-2 (200 mg, 0.47 mmol) in DME (1.0 mL) is added TMSCF$_3$ (139 mg, 0.98 mol) and tetramethylammonium fluoride (43 mg, 0.47 mmol) at −50° C. The resulting mixture is allowed to warm to room temperature and stirred for 16 h. The mixture is concentrated in vacuo and the residue is purified by reverse HPLC (30-95%, MeCN/Water) to give F-3.

A mixture of F-3 (670 mg, 1.74 mmol) and 10% palladium on carbon (210 mg) in MeOH (17 mL) is stirred under an atmosphere of H$_2$ at room temperature for 15 h. The mixture is filtered through Diatomaceous earth and the filter pad is washed with MeOH. The filtrate is concentrated to provide the title product (F).

Preparation of 4-methyl-piperidine-carboxylic acid methyl ester hydrochloride (I-1)

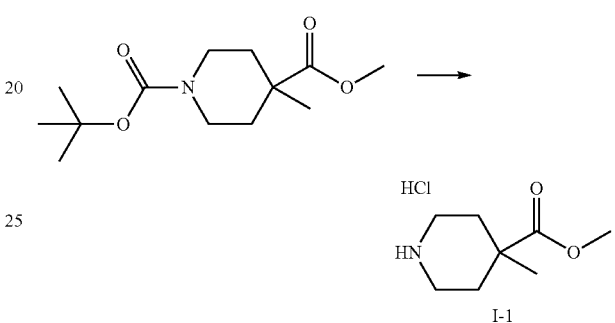

To a stirred solution of 4-methyl-piperidine-1,4-dicarboxylic acid mono-tert-butyl ester (1.00 g, 4.10 mmol) in MeOH (2 mL) is added HCl (5 ml, 4 M in dioxane). After 18 h, the mixture is evaporated to dryness, the residue is dissolved in MeOH (3 mL), and the stirred solution is treated with Et$_2$O (45 ml). The resulting solid is filtered and dried to give the title compound.

The following intermediates are also prepared according to the procedure described for the synthesis of I-1:

| Intermediate # | Structure |
|---|---|
| I-2 | 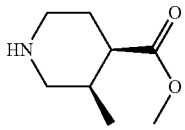 |
| I-3 | 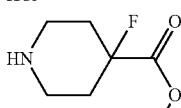 |
| I-4 | 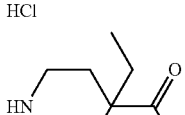 |

-continued

| Intermediate # | Structure |
|---|---|
| I-5 | HCl 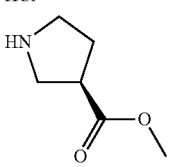 |
| I-6 | HCl 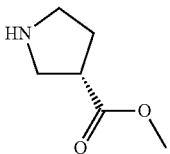 |

Synthesis of Compounds of Formula I

General Method A Through E

Protocols for Reductive Amination

Example of General Method A

Preparation of 8-[(S)-4-(2,3-Dihydro-[1,4]dioxino[2,3-b]pyridin-3-yl)-benzyl]-2,8-diaza-spiro[4.5]decan-1-one Example 125

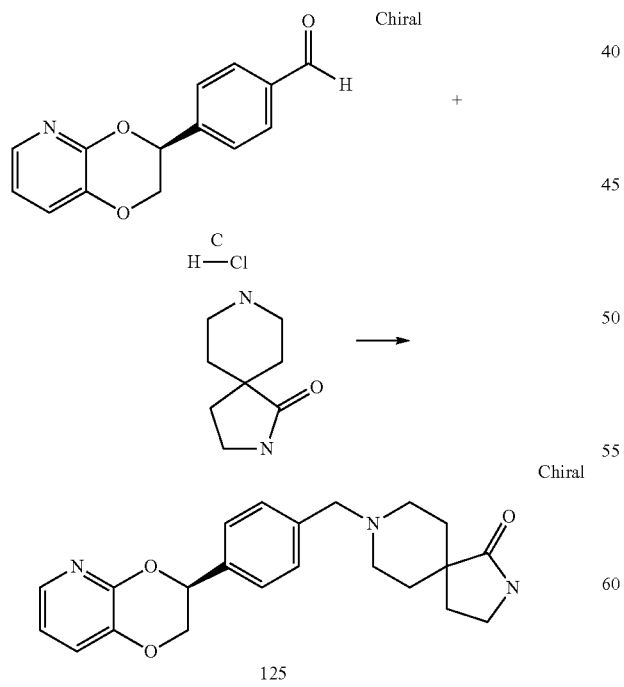

125

TEA (0.12 mL, 0.83 mmol) is added to a mixture of C (100 mg, 0.42 mmol) and 2,8-Diaza-spiro[4.5]decan-1-one;

hydrochloride (158 mg, 0.83 mmol) in 2 mL of DCM One drop of acetic acid is added, and the mixture is stirred for 10 min, sodiumacetoxyborohydride (132 mg, 0.83 mmol) is added, and the resulting mixture is stirred for 24 h. The solvent is evaporated and the crude mixture is dissolved in 2 ml of MeCN/H$_2$O (1:1). The mixture is purified on a reverse phase C18 semi-preparative HPLC to column eluting with a gradient of 0-95% MeCN/H$_2$O to give the title product.

Example of General Method B

Preparation of (±)-4-[4-(2,3-Dihydro-benzo[1,4]dioxin-2-yl)-benzyl]-piperazine-1-carboxylic acid tert-butyl ester

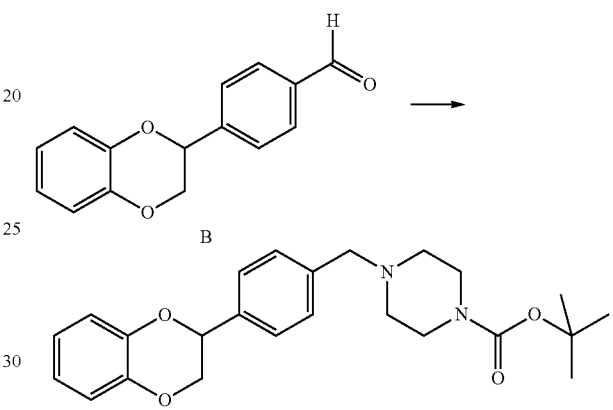

B

To a solution of B (100 mg, 0.420 mmol), and piperazine-1-carboxylic acid tert-butyl ester (93 mg, 0.50 mmol) in DCE (4 mL) is added acetic acid (50 mg, 0.83 mmol). The mixture is stirred at room temperature for 10 min, treated with sodium triacetoxyborohydride (141 mg, 0.67 mmol), and stirred at room temperature for 16 hours. The reaction is diluted with saturated aqueous sodium bicarbonate (5 mL) and extracted with EtOAc (5 mL×3). The combined organic layers is washed with brine, dried over Na$_2$SO$_4$, filtered and concentrated. The residue is purified on a reversed phase C18 semi-preparative HPLC column eluting with a gradient of 5-85% MeCN+0.1% TFA/H$_2$O+0.1% TFA). The combined fractions are concentrated and basified by saturated aqueous sodium bicarbonate (5 mL) and extracted with EtOAc (5 mL×3). The combined organic phases is washed by brine, dried over Na$_2$SO$_4$, filtered, and concentrated to give the title product.

Example of General Method C

Preparation of 4-{1-[(S)-4-(2,3-Dihydro-benzo[1,4]dioxin-2-yl)-benzyl]-piperidin-4-ylmethyl}-benzoic acid methyl ester

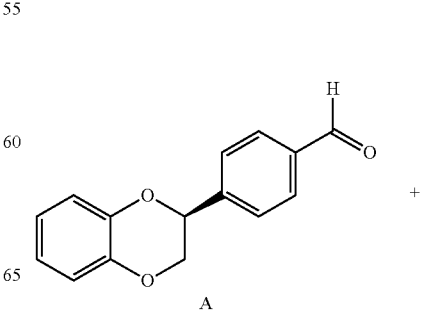

A

-continued

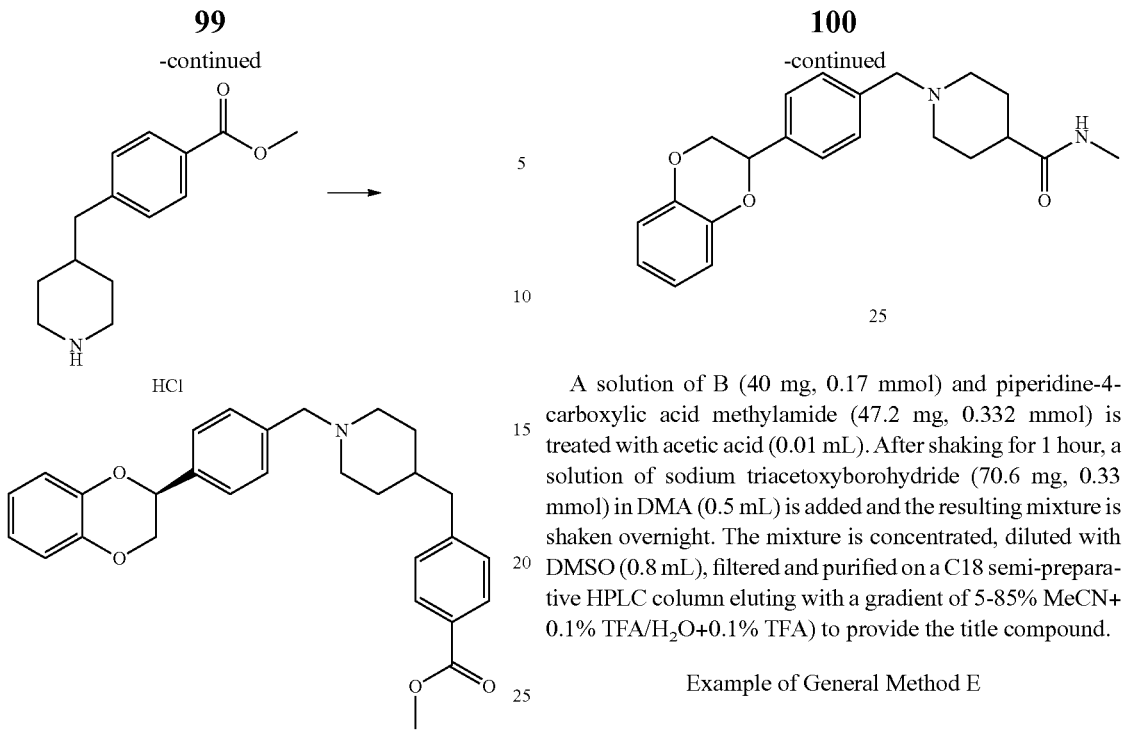

A solution of A (100 mg, 0.42 mmol), 4-piperidin-4-ylm-ethyl-benzoic acid methyl ester hydrochloride (146 mg, 0.54 mmol), sodium cyanoborohydride (52 mg, 0.83 mmol), and TEA (0.08 mL, 0.54 mmol) in THF (5 mL) is treated with 2 drops of acetic acid, and stirred at room temperature for 16 h. The mixture is concentrated, and the residue is purified by flash chromatography eluting with a gradient of 0-10% MeOH in DCM to give the title compound.

Example of General Method D

Preparation of 1-[4-(2,3-Dihydro-benzo[1,4]dioxin-2-yl)-benzyl]-piperidine-4-carboxylic acid methylamide Example 25

-continued

A solution of B (40 mg, 0.17 mmol) and piperidine-4-carboxylic acid methylamide (47.2 mg, 0.332 mmol) is treated with acetic acid (0.01 mL). After shaking for 1 hour, a solution of sodium triacetoxyborohydride (70.6 mg, 0.33 mmol) in DMA (0.5 mL) is added and the resulting mixture is shaken overnight. The mixture is concentrated, diluted with DMSO (0.8 mL), filtered and purified on a C18 semi-preparative HPLC column eluting with a gradient of 5-85% MeCN+ 0.1% TFA/H$_2$O+0.1% TFA) to provide the title compound.

Example of General Method E

Preparation of 4-{[(S)-4-(2,3-Dihydro-benzo[1,4]dioxin-2-yl)-benzylamino]-methyl}-benzoic acid methyl ester

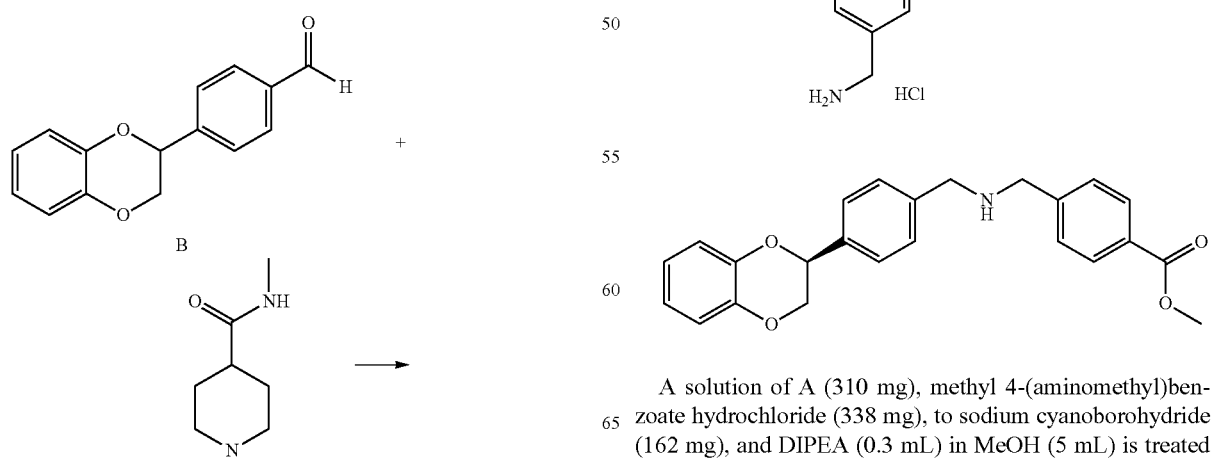

A solution of A (310 mg), methyl 4-(aminomethyl)benzoate hydrochloride (338 mg), to sodium cyanoborohydride (162 mg), and DIPEA (0.3 mL) in MeOH (5 mL) is treated with 2 drops of acetic acid, and the resulting mixture is stirred at room temperature for 16 h. The mixture is concentrated, and the residue is purified by flash chromatography eluting with a gradient of 0-10% MeOH in DCM to give the title compound.

Table 3 provides a summary of the key reagents used to prepare Examples 1-191 according to general methods A, B, C, D, E, or F as depicted in the reaction below.

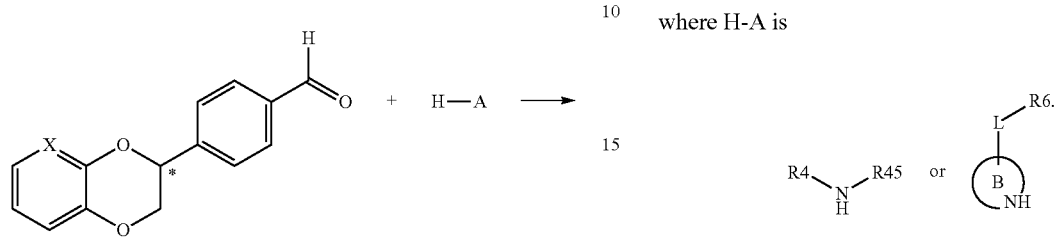

-continued

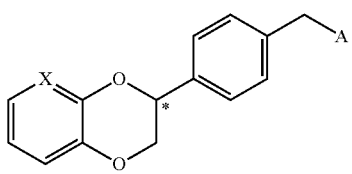

where H-A is

TABLE 3

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 1 | CH | racemic | pyrrolidine | B | 10 | 296.2 | 1.20 |
| 2 | CH | racemic | morpholine | B | 10 | 312.2 | 1.20 |
| 3 | CH | racemic | 4,4-dimethylpiperidine | B | 10 | 338.4 | 1.20 |
| 4 | CH | racemic | spiro piperidine-pyrrolidinone | B | 10 | 379.4 | 1.10 |
| 5 | CH | racemic | 4-fluoropiperidine | B | 10 | 328.4 | 1.11 |
| 6 | CH | racemic | azabicyclic | B | 10 | 322.4 | 1.13 |
| 7 | CH | racemic | thiomorpholine dioxide | B | 10 | 360.4 | 1.40 |
| 8 | CH | S | N,N-dimethylpiperidine-4-carboxamide | B | 10 | 381.3 | 0.67 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 9 | CH | racemic | pyrrolidine-3-OH | B | 10 | 312.4 | 1.04 |
| 10 | CH | racemic | 3-((2-oxopyrrolidin-1-yl)methyl)piperidine | B | 10 | 407.4 | 1.14 |
| 11 | CH | racemic | 4-acetylpiperazine | B | 10 | 353.40 | 1.47 |
| 12 | CH | racemic | 2-(pyrrolidin-1-yl)-2-oxoethylamine | B | 10 | 353.40 | 1.57 |
| 13 | CH | S | 1-(methylsulfonyl)-N,N-dimethylpiperidin-4-amine | A | 10 | 417.40 | 1.62 |
| 14 | CH | S | 1-acetyl-N,N-dimethylpiperidin-4-amine | A | 10 | 381.40 | 1.57 |
| 15 | N | racemic | pyrrolidine | B | 10 | 297.40 | 0.97 |
| 16 | CH | racemic | 5,6,7,8-tetrahydro-[1,2,4]triazolo[4,3-a]pyrazine | B | 10 | 349.40 | 2.14 |
| 17 | N | racemic | thiomorpholine-1,1-dioxide | B | 10 | 361.20 | 1.66 |
| 18 | N | racemic | morpholine | B | 10 | 313.40 | 0.89 |

TABLE 3-continued

Examples synthesized by General Method A, B, C, D, E, or F

| Ex # | X | Chirality at * | —A | Synthesis Method | LC/MS Method | [M + H]⁺ | Rt (min) |
|---|---|---|---|---|---|---|---|
| 19 | CH | S | piperidine-3-carboxylic acid (S) | C | 1 | 354.52 | 0.55 |
| 20 | CH | S | piperidine-3-carboxylic acid (S) | C | 1 | 354.24 | 0.56 |
| 21 | CH | S | 4-(2,2,2-trifluoro-1-hydroxyethyl)piperidine | C | 1 | 408.26 | 0.71 |
| 22 | CH | S | 4-(1,1,1,3,3,3-hexafluoro-2-hydroxypropan-2-yl)piperidine | C | 1 | 476.23 | 0.77 |
| 23 | CH | racemic | tert-butylamine | D | 11 | 298.2 | 0.7 |
| 24 | CH | racemic | (S)-sec-butylamine | D | 11 | 298.2 | 0.73 |
| 25 | CH | racemic | N-methyl piperidine-4-carboxamide | D | 11 | 367.3 | 0.66 |
| 26 | CH | racemic | 4-(piperidin-4-yl)butanoic acid | D | 11 | 396.3 | 0.73 |
| 27 | CH | racemic | (piperidin-4-yl)methanol | D | 11 | 340.2 | 0.66 |
| 28 | CH | racemic | 2-(piperidin-4-yl)propan-2-ol | D | 11 | 368.3 | 0.72 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 29 | CH | racemic | piperidine-CH2CH2CH2OH | D | 11 | 368.5 | 0.7 |
| 30 | CH | racemic | N-methyl-1,4-diazepane | D | 11 | 339.2 | 0.56 |
| 31 | CH | racemic | N-acetyl-1,4-diazepane | D | 11 | 367.2 | 0.65 |
| 32 | CH | racemic | 1,4-oxazepane | D | 11 | 326.2 | 0.67 |
| 33 | CH | racemic | N-methyl-N-(2-methoxyethyl)amine | D | 11 | 314.2 | 0.71 |
| 34 | CH | racemic | 3-hydroxypyrrolidine | D | 11 | 312.2 | 0.65 |
| 35 | CH | racemic | 1,3,8-triazaspiro[4.5]decane-2,4-dione | D | 11 | 394.2 | 0.65 |
| 36 | CH | racemic | 3-methoxyazetidine | D | 11 | 312.4 | 0.68 |
| 37 | CH | racemic | 4-(morpholine-4-carbonyl)piperidine | D | 11 | 423.3 | 0.69 |
| 38 | CH | racemic | 4-(N,N-dimethylacetamido)piperidine | D | 11 | 395.3 | 0.70 |
| 39 | CH | racemic | 4-(methylsulfonyl)piperidine | D | 11 | 388.2 | 0.66 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 40 | CH | racemic | azepane | D | 11 | 324.3 | 0.79 |
| 41 | CH | racemic | HN-cyclopentyl | D | 11 | 310.2 | 0.78 |
| 42 | CH | racemic | N-methyl-N-(2-(pyridin-2-yl)ethyl)amine | D | 11 | 361.2 | 0.79 |
| 43 | CH | racemic | HN-CH2-cyclopropyl | D | 11 | 296.2 | 0.75 |
| 44 | CH | racemic | 4-hydroxy-4-phenylpiperidine | D | 11 | 402.3 | 0.82 |
| 45 | CH | racemic | N,N-diethylamine | D | 11 | 298.2 | 0.75 |
| 46 | CH | racemic | 3-cyanoazetidine | D | 11 | 306.8 | 0.73 |
| 47 | CH | racemic | 3-methoxypyrrolidine | D | 11 | 326.2 | 0.74 |
| 48 | CH | racemic | 4-(methylsulfonamido)piperidine | D | 11 | 403.2 | 0.71 |
| 49 | CH | racemic | N-(2-methyl-1-(pyrrolidin-1-yl)propan-2-yl)amine | D | 11 | 367.2 | 0.68 |
| 50 | CH | racemic | 4-((2-oxopyrrolidin-1-yl)methyl)piperidine | D | 11 | 407.3 | 0.73 |
| 51 | CH | racemic | N,N-dimethylpiperidine-4-carboxamide | D | 11 | 381.3 | 0.73 |

TABLE 3-continued

Examples synthesized by General Method A, B, C, D, E, or F

| Ex # | X | Chirality at * | —A | Synthesis Method | LC/MS Method | [M + H]⁺ | Rt (min) |
|---|---|---|---|---|---|---|---|
| 52 | CH | racemic | piperidine-C(O)NH-CH₂CH₂OH | D | 11 | 397.3 | 0.67 |
| 53 | CH | racemic | piperidine-NH-C(O)NH₂ | D | 11 | 368.2 | 0.67 |
| 54 | CH | racemic | NH-CH₂-(3-pyridyl) | D | 11 | 333.2 | 0.66 |
| 55 | CH | racemic | HN-CH₂-(1-methylimidazol-4-yl) | D | 11 | 336.2 | 0.59 |
| 56 | CH | S | 1,2,3,4-tetrahydroisoquinoline-4-carboxylic acid (N-linked) | D | 11 | 402.3 | 0.75 |
| 57 | CH | S | trans-3-aminocyclopentanecarboxylic acid | D | 11 | 354.1 | 0.63 |
| 58 | CH | S | 3-amino-4,4-dimethylpentanoic acid | D | 11 | 370.2 | 0.70 |
| 59 | CH | S | 1-aminocyclopentanecarboxylic acid | D | 11 | 354.2 | 0.66 |
| 60 | CH | S | sarcosine (N-methylglycine) | D | 11 | 314.3 | 0.63 |
| 61 | CH | S | pyrrolidine-3-carboxylic acid (N-linked) | D | 11 | 340.1 | 0.61 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 62 | CH | S | HN-cyclohexyl-COOH | D | 11 | 367.9 | 0.61 |
| 63 | CH | S | HN-cyclohexyl-COOH | D | 11 | 368.2 | 0.64 |
| 64 | CH | S | HN-pyrrolidine-N-acetyl | D | 11 | 353.8 | 0.63 |
| 65 | CH | S | HN-pyrrolidine-N-acetyl | D | 11 | 353.1 | 0.63 |
| 66 | CH | S | HN-cyclohexyl-CONH2 | D | 11 | 367.1 | 0.64 |
| 67 | CH | S | N(Me)-cyclohexyl | D | 11 | 337.8 | 0.78 |
| 68 | CH | S | 2-methylpiperidinyl | D | 11 | 323.9 | 0.73 |
| 69 | CH | S | 3-(hydroxymethyl)piperidinyl | D | 11 | 339.8 | 0.66 |
| 70 | CH | S | 4-(2-hydroxyethyl)piperidinyl | D | 11 | 353.9 | 0.67 |
| 71 | CH | S | NH-isopropyl | D | 11 | 284.3 | 0.68 |
| 72 | CH | S | NH-CH(CH3)-CH2-OMe | D | 11 | 313.6 | 0.70 |

TABLE 3-continued
Examples synthesized by General Method A, B, C, D, E, or F
| Ex # | X | Chirality at * | —A | Synthesis Method | LC/MS Method | [M + H]+ | Rt (min) |
|---|---|---|---|---|---|---|---|
| 73 | CH | S | 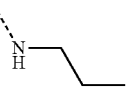 | D | 11 | 283.8 | 0.7 |
| 74 | CH | S | 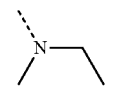 | D | 11 | 283.9 | 0.67 |
| 75 | CH | S | 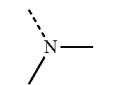 | D | 11 | 269.8 | 0.65 |
| 76 | CH | S |  | D | 11 | 340.2 | 0.65 |
| 77 | CH | S | 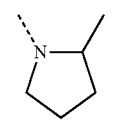 | D | 11 | 310.2 | 0.70 |
| 78 | CH | S | 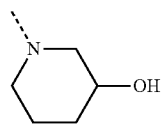 | D | 11 | 325.9 | 0.65 |
| 79 | CH | S | 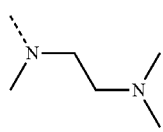 | D | 11 | 327.1 | 0.61 |
| 80 | CH | S | 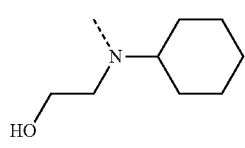 | D | 11 | 367.9 | 0.76 |
| 81 | CH | S | 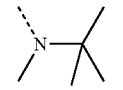 | D | 11 | 311.7 | 0.71 |
| 82 | CH | S | 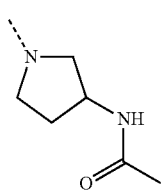 | D | 11 | 352.9 | 0.64 |
| 83 | CH | S | 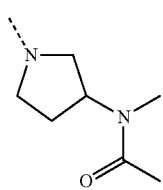 | D | 11 | 366.9 | 0.67 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 84 | CH | S | | D | 11 | 336.2 | 0.73 |
| 85 | CH | S | | D | 11 | 363.8 | 0.76 |
| 86 | CH | S | | D | 11 | 366.9 | 0.63 |
| 87 | CH | S | | D | 11 | 354.4 | 0.68 |
| 88 | CH | S | | D | 11 | 313.3 | 0.64 |
| 89 | CH | S | | D | 11 | 353.9 | 0.70 |
| 90 | CH | S | | D | 11 | 340.8 | 0.59 |
| 91 | CH | S | | D | 11 | 311.8 | 0.57 |
| 92 | CH | S | | D | 11 | 311.1 | 0.75 |

TABLE 3-continued

Examples synthesized by General Method A, B, C, D, E, or F

| Ex # | X | Chirality at * | —A | Synthesis Method | LC/MS Method | [M + H]⁺ | Rt (min) |
|---|---|---|---|---|---|---|---|
| 93 | CH | S | | D | 11 | 339.1 | 0.49 |
| 94 | CH | S | | D | 11 | 407.2 | 0.63 |
| 95 | CH | S | | D | 11 | 377.8 | 0.78 |
| 96 | CH | S | | D | 11 | 397.3 | 0.56 |
| 97 | CH | S | | D | 11 | 339.8 | 0.65 |
| 98 | CH | S | | D | 11 | 340.2 | 0.63 |
| 99 | CH | S | | D | 11 | 407.4 | 0.62 |
| 100 | CH | S | | D | 11 | 338.2 | 0.76 |
| 101 | CH | S | | D | 11 | 325.8 | 0.62 |
| 102 | CH | S | | D | 11 | 325.7 | 0.6 |
| 103 | CH | S | | D | 11 | 326.3 | 0.61 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 104 | CH | S | | D | 11 | 395.2 | 0.8 |
| 105 | CH | S | | D | 11 | 353.9 | 0.66 |
| 106 | CH | S | | D | 11 | 353.9 | 0.67 |
| 107 | CH | S | | D | 11 | 325.9 | 0.61 |
| 108 | CH | S | | D | 11 | 352.9 | 0.56 |
| 109 | CH | S | | D | 11 | 338.4 | 0.71 |
| 110 | CH | S | | D | 11 | 353.1 | 0.44 |
| 111 | CH | S | | D | 11 | 348.1 | 0.64 |
| 112 | CH | S | | D | 11 | 374.1 | 0.66 |
| 113 | CH | Racemic | | A | 13 | 354.4 | 1.1 |
| 114 | CH | Racemic | | A | 13 | 353.4 | 1.0 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 115 | CH | Racemic | | A | 13 | 314.4 | 1.0 |
| 116 | CH | S | | A | 12 | 393.1 | 1.3 |
| 117 | CH | S | | A | 13 | 365.4 | 1.3 |
| 118 | CH | S | | A | 13 | 393.4 | 1.2 |
| 119 | CH | S | | A | 13 | 393.4 | 1.1 |
| 120 | CH | S | | A | 7 | 407.3 | 0.7 |
| 121 | CH | S | | A | 13 | 393.4 | 1.1 |
| 122 | CH | S | | A | 7 | 429.5 | 0.7 |
| 123 | CH | S | | A | 7 | 408.3 | 0.6 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 124 | CH | S | | A | 7 | 390.3 | 0.7 |
| 125 | N | S | | A | 11 | 380.4 | 0.4 |
| 126 | N | S | | A | 11 | 297.2 | 0.4 |
| 127 | N | S | | A | 11 | 366.2 | 0.4 |
| 128 | CH | S | | A | 11 | 423.3 | 0.6 |
| 129 | N | S | | A | 11 | 394.2 | 0.4 |
| 130 | N | S | | A | 11 | 408.3 | 0.5 |
| 131 | CH | S | | A | 11 | 339.2 | 0.6 |
| 132 | N | S | | A | 13 | 340.2 | 0.9 |
| 133 | N | S | | A | 11 | 328.2 | 0.4 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 134 | CH | S | piperidine-CH2CH2COOH | A | 13 | 382.4 | 0.6 |
| 135 | N | S | cyclopentylamine | D | 11 | 311.1 | 0.52 |
| 136 | N | S | piperidine-3-carboxamide | D | 11 | 354.1 | 0.42 |
| 137 | N | S | 4-methylpiperidine | D | 11 | 325.1 | 0.53 |
| 138 | N | S | N-methyl-N-(2-pyridin-2-ylethyl)amine | D | 11 | 362.1 | 0.51 |
| 139 | N | S | azepane | D | 11 | 325.1 | 0.52 |
| 140 | N | S | N-ethyl-N-methylamine | D | 11 | 285.3 | 0.43 |
| 141 | N | S | diethylamine | D | 11 | 299.1 | 0.47 |
| 142 | N | S | N-cyclopentyl-N-methylamine | D | 11 | 325.1 | 0.53 |
| 143 | N | S | 4-methyl-1,4-diazepane | D | 11 | 340.1 | 0.31 |
| 144 | N | S | (3S)-3-hydroxypyrrolidine | D | 11 | 313.1 | 0.41 |
| 145 | N | S | 2-azabicyclo[2.2.1]heptane | D | 11 | 323.1 | 0.49 |

TABLE 3-continued
Examples synthesized by General Method A, B, C, D, E, or F
| Ex # | X | Chirality at * | —A | Synthesis Method | LC/MS Method | [M + H]⁺ | Rt (min) |
|---|---|---|---|---|---|---|---|
| 146 | N | S | 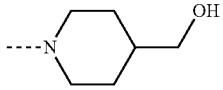 | D | 11 | 341.1 | 0.43 |
| 147 | N | S | 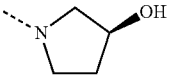 | D | 11 | 313.1 | 0.41 |
| 148 | N | S | 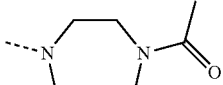 | D | 11 | 368.1 | 0.41 |
| 149 | N | S | 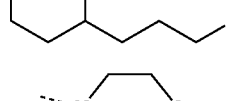 | D | 11 | 369.1 | 0.47 |
| 150 | N | S | 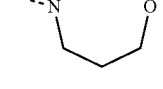 | D | 11 | 327.1 | 0.44 |
| 151 | N | S | 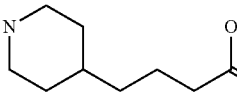 | D | 11 | 397.1 | 0.51 |
| 152 | N | S | 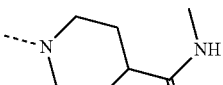 | D | 11 | 368.1 | 0.42 |
| 153 | N | S | 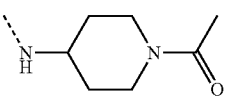 | D | 11 | 368.1 | 0.42 |
| 154 | N | S | 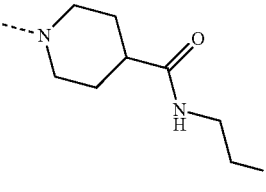 | D | 11 | 398.1 | 0.40 |
| 155 | N | S | 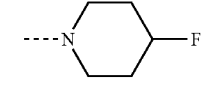 | D | 11 | 329.1 | 0.47 |
| 156 | N | S | 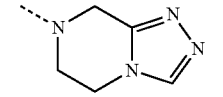 | D | 11 | 350.1 | 0.56 |
| 157 | N | S | 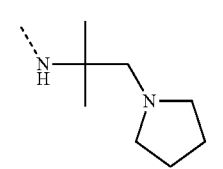 | D | 11 | 368.1 | 0.40 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 158 | N | S | | D | 11 | 341.1 | 0.48 |
| 159 | N | S | | D | 11 | 336.1 | 0.44 |
| 160 | N | S | | D | 11 | 368.1 | 0.41 |
| 161 | N | S | | D | 11 | 361.0 | 0.65 |
| 162 | N | S | | D | 11 | 424.1 | 0.46 |
| 163 | N | S | | D | 11 | 408.1 | 0.47 |
| 164 | N | S | | D | 11 | 355.1 | 0.38 |
| 165 | N | S | | D | 11 | 395.1 | 0.41 |
| 166 | N | S | | D | 11 | 313.1 | 0.45 |
| 167 | N | S | | D | 11 | 404.1 | 0.45 |
| 168 | N | S | | D | 11 | 327.1 | 0.46 |
| 169 | N | S | | D | 11 | 418.1 | 0.47 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 170 | N | S | piperidine-O-CH2CH2-O-CH3 | D | 11 | 385.1 | 0.50 |
| 171 | N | S | piperidine-CH2-C(=O)-N(CH3)2 | D | 11 | 396.1 | 0.47 |
| 172 | N | S | piperidine-S(=O)2-CH3 | D | 11 | 389.1 | 0.43 |
| 173 | N | S | NH-cyclobutyl | D | 11 | 297.1 | 0.48 |
| 174 | CH | S | NH-piperidine-N-S(=O)2-CH3 | A | 15 | 403.2 | 0.69 |
| 175 | CH | S | piperidine-NH-C(=O)-NH2 | A | 15 | 368.4 | 0.55 |
| 176 | CH | S | piperidine-NH-S(=O)2-CH3 | A | 15 | 403.2 | 0.90 |
| 177 | CH | S | piperidine-CN | A | 15 | 336.2 | 0.85 |
| 178 | CH | S | piperidine-NH-C(=O)-CH3 | A | 15 | 368.0 | 0.98 |
| 179 | CH | S | piperidine-C(=O)-NH-CH3 | A | 15 | 367.2 | 1.02 |
| 180 | CH | S | piperidine-C(=O)-morpholine | A | 15 | 423.3 | 1.03 |
| 181 | CH | S | piperidine-CH2CH2CH2-C(=O)-OH | A | 15 | 395.9 | 1.13 |

TABLE 3-continued

Examples synthesized by General Method A, B, C, D, E, or F

| Ex # | X | Chirality at * | —A | Synthesis Method | LC/MS Method | [M + H]+ | Rt (min) |
|---|---|---|---|---|---|---|---|
| 182 | CH | S | piperidine-CH2-COOH (3S) | A | 15 | 368.2 | 1.04 |
| 183 | CH | S | piperidine-CH2-COOH (3R) | A | 15 | 368.2 | 1.05 |
| 184 | CH | S | pyrrolidine-CH2-COOH | A | 15 | 354.2 | 0.99 |
| 185 | N | S | N-acetylpiperazine | A | 14 | 354.4 | 2.09 |
| 186 | N | S | 4-hydroxypiperidine | A | 14 | 327.1 | 2.13 |
| 187 | N | S | 4-ureidopiperidine | A | 14 | 369.2 | 2.09 |
| 188 | N | S | N-methylsulfonylpiperazine | A | 14 | 390.4 | 2.22 |
| 189 | N | S | piperidine-4-carboxylic acid | A | 14 | 355.1 | 2.16 |
| 190 | N | S | 4-(methylsulfonamido)piperidine | A | 14 | 404.2 | 2.16 |
| 191 | CH | S | 3-aminocyclopentane-carboxylic acid | A | 14 | 353.8 | 0.63 |

Examples 192 and 193

Preparation of (S)-1-[4-(2,3-Dihydro-benzo[1,4]dioxin-2-yl)-benzyl]-piperidin-4-ol (192), and (R)-1-[4-(2,3-Dihydro-benzo[1,4]dioxin-2-yl)-benzyl]-piperidin-4-ol (193)

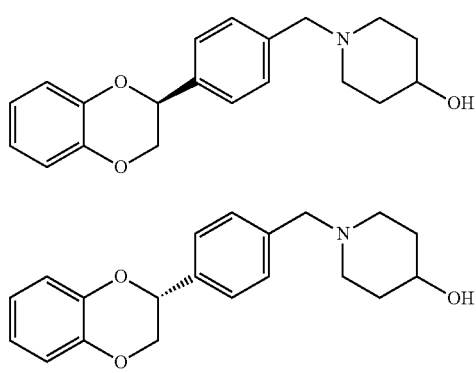

A racemic mixture of 192 and 193 is prepared from intermediate B and 4-hydroxypiperidine according to the General Method B, and resolved by SCF Chiral HPLC using 20% MeOH, 1% IPA, and super critical carbon dioxide to give 192 as the first-eluting peak, and 193 as the second-eluting peak. 192: LC/MS Method 10; Rt=0.98 min.; [M+H]$^+$=326.4. 193: LC/MS Method 10; Rt=0.98 min.; [M+H]$^+$=326.4.

Examples 194 and 195

Preparation of 8-[(S)-4-(2,3-Dihydro-benzo[1,4]dioxin-2-yl)-benzyl]-2,8-diaza-spiro[4.5]decan-1-one (194) and (8-[(R)-4-(2,3-Dihydro-benzo[1,4]dioxin-2-yl)-benzyl]-2,8-diaza-spiro[4.5]decan-1-one (195)

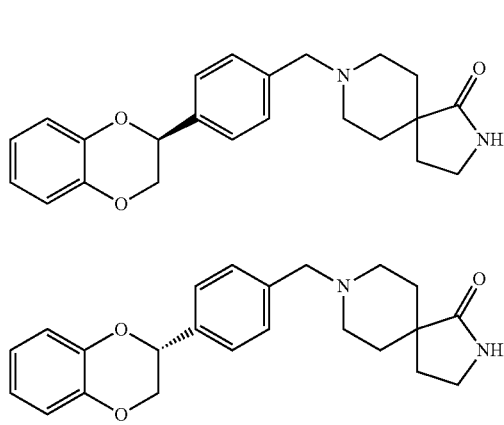

Compound 4 (racemate) is resolved by SCF Chiral HPLC using 55% methanol, 1% isopropylamine, and super critical carbon dioxide to give 194 as the first-eluting peak, and 195 as the second-eluting peak. 194: LC/MS Method 10; Rt=1.10 min.; [M+H]$^+$=379.4. 195: LC/MS Method 10; Rt=1.09 min.; [M+H]$^+$=379.4.

Examples 196 and 197

Preparation of 1-[(S)-4-(2,3-dihydro-benzo[1,4]dioxin-2-yl)-benzyl]-pyrrolidine (196) and 1-[(R)-4-(2,3-dihydro-benzo[1,4]dioxin-2-yl)-benzyl]-pyrrolidine (197)

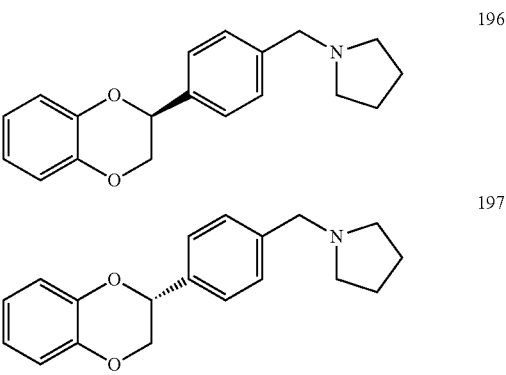

Compound 1 (racemate) is resolved by HPLC using a Chiralpak AD-H column, and eluting with 7% IPA in heptanes with 0.1% DEA to give 196 as the first-eluting peak, and 197 as the second-eluting peak. 196: LC/MS Method 10; Rt=1.21 min.; [M+H]$^+$=296.2. 197: LC/MS Method 10; Rt=1.21 min.; [M+H]$^+$=296.2.

Examples 198 and 199

Preparation of 4-[(S)-4-(2,3-dihydro-benzo[1,4]dioxin-2-yl)-benzyl]-morpholine (198) and 4-[(R)-4-(2,3-dihydro-benzo[1,4]dioxin-2-yl)-benzyl]-morpholine (199)

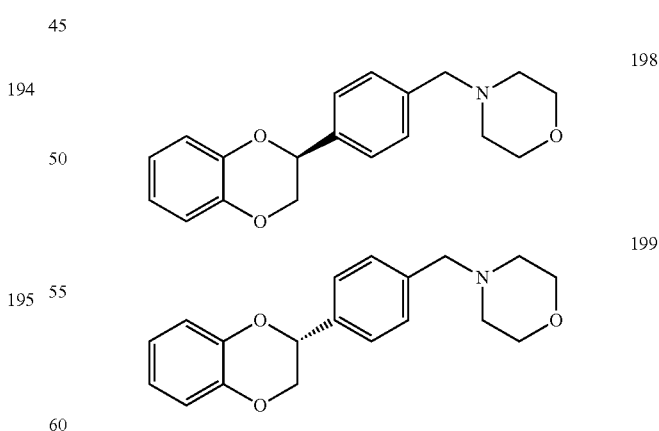

Compound 2 (racemate) is resolved by HPLC using a Chiralpak OD-H column and eluting with 7% IPA in heptanes with 0.1% DEA to give 198 as the first-eluting peak and 199 as the second-eluting peak. 198: LC/MS Method 10; Rt=1.20 min.; [M+H]$^+$=312.4. 199: LC/MS Method 10; Rt=1.21 min.; [M+H]$^+$=312.4.

Examples 200 and 201

Preparation of (S)-1-[4-(2,3-dihydro-benzo[1,4]dioxin-2-yl)-benzyl]-piperidine-4-carboxylic acid (200) and (R)-1-[4-(2,3-Dihydro-benzo[1,4]dioxin-2-yl)-benzyl]-piperidine-4-carboxylic acid (201)

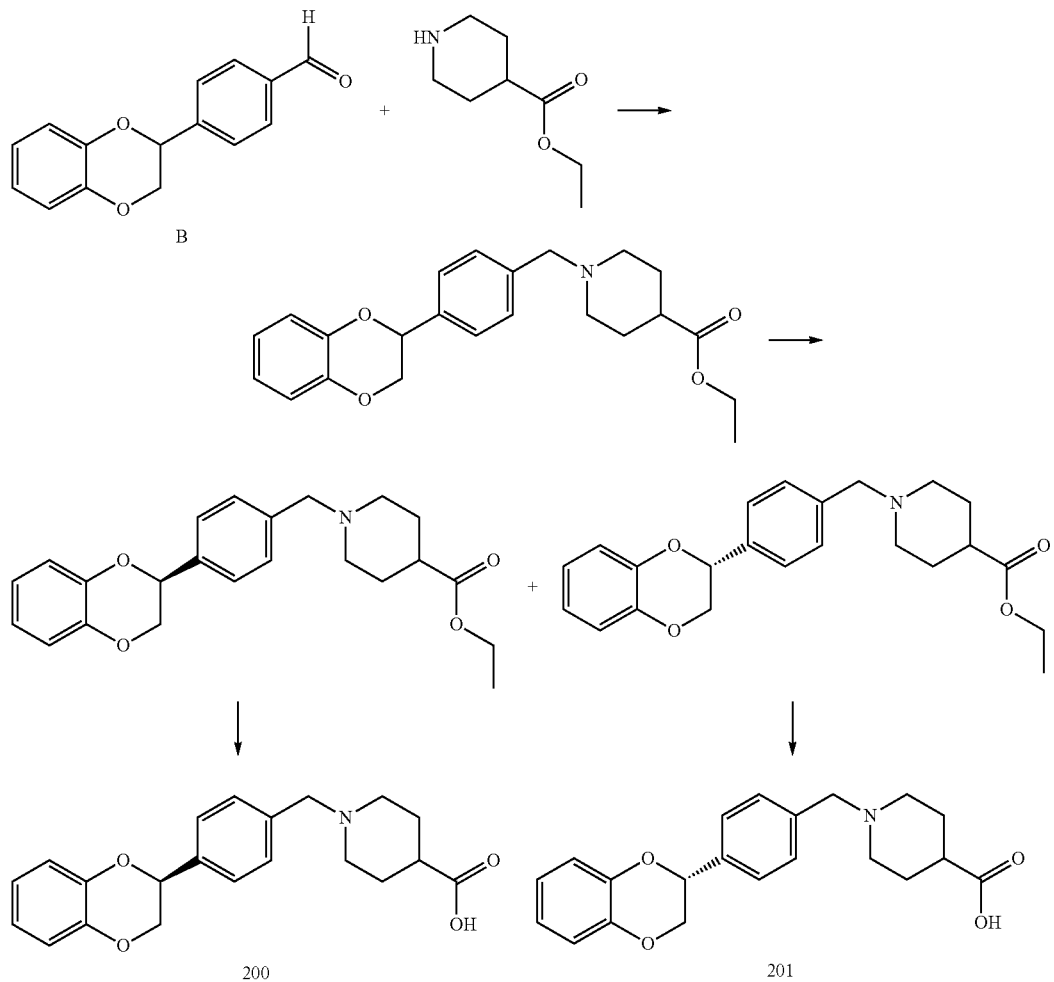

1-[4-(2,3-Dihydro-benzo[1,4]dioxin-2-yl)-benzyl]-piperidine-4-carboxylic acid ethyl ester is prepared from intermediate B and ethyl isonipecotate according to the procedure described in General Method B, and resolved by HPLC using a Chiralpak OD-H column, and eluting with 12% IPA in heptanes with 0.1% DEA to give (S)-1-[4-(2,3-dihydro-benzo[1,4]dioxin-2-yl)-benzyl]-piperidine-4-carboxylic acid ethyl ester as the first-eluting peak, and (R)-1-[4-(2,3-dihydro-benzo[1,4]dioxin-2-yl)-benzyl]-piperidine-4-carboxylic acid ethyl ester as the second-eluting peak.

(S)-1-[4-(2,3-Dihydro-benzo[1,4]dioxin-2-yl)-benzyl]-piperidine-4-carboxylic acid ethyl ester (145 mg, 0.380 mmol) and lithium hydroxide monohydrate (48 mg, 1.1 mmol) are heated in 1:1 mixture of MeOH/water (2 mL) at 75° C. for 2 h. The reaction mixture is acidified with TFA (300 µL). The resulting white precipitate is filtered off, washed with water, and dried to give compound 200. LC/MS Method 10; Rt=1.14 min.; [M+H]⁺=382.4.

Compound 201 is prepared from (R)-1-[4-(2,3-Dihydro-benzo[1,4]dioxin-2-yl)-benzyl]-piperidine-4-carboxylic acid ethyl ester according to the procedure described for the synthesis of compound 201. LC/MS Method 10; Rt=1.13 min.; [M+H]⁺=382.4.

Example: 202

Preparation of 4-[4-(7-Fluoro-2,3-dihydro-benzo[1,4]dioxin-2-yl)-benzyl]-morpholine (202)

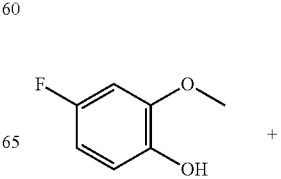

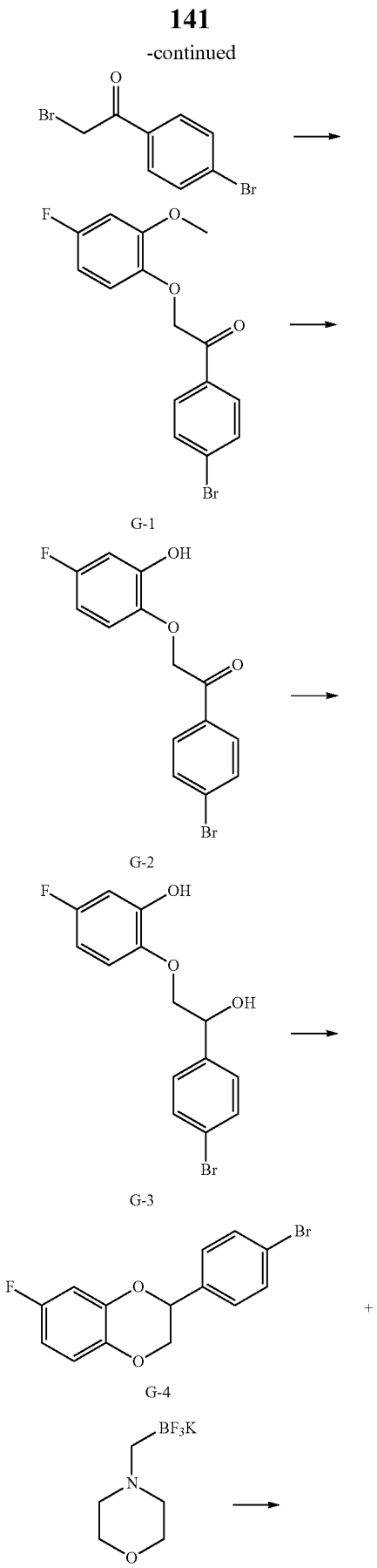

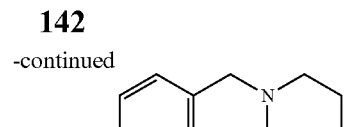

A solution of 4-fluoro-2-methoxy-phenol (3.0 g, 21.1 mmol) in acetone (250 mL) is treated to with cesium carbonate (8.3 g, 25.3 mmol) followed by 2-bromo-1-(4-bromophenyl)-ethanone (5.9 g, 21.1 mmol). The resulting mixture is stirred at room temperature for 2 h. Water (600 mL) is added slowly to the vigorously stiffing solution. After stirring for 30 minutes, the precipitate is filtered off and washed with copious water to give 1-(4-bromo-phenyl)-2-(4-fluoro-2-methoxy-phenoxy)-ethanone (G-1).

G-1 (3.0 g, 8.85 mmol) is dissolved in DCM (30 mL) and cooled to 0° C. Aluminum chloride (2.9 g, 22.1 mmol) is added in one portion and the reaction is stirred at 0° C. for 10 minutes. Ethanethiol (1.6 mL, 22.1 mmol.) is added and the reaction is stirred at 0° C. for 30 minutes. The reaction mixture is poured onto ice and the resulting slurry is stirred for 30 minutes. The product is the extracted with EtOAc (3×50 mL). The combined organic extracts are dried over sodium sulfate, concentrated, and purified by flash column chromatography on silica gel (0 to 50% EtOAc in heptane) to provide 1-(4-bromo-phenyl)-2-(4-fluoro-2-hydroxy-phenoxy)-ethanone (G-2).

To a solution of G-2 (1.25 g, 3.85 mmol) in EtOH (25 mL) is added sodium borohydride (291 mg, 7.69 mmol), and the mixture is stirred at room temperature for 2 h. Water (5 mL) is added, and the resulting mixture is stirred at room temperature for 1 h. The reaction mixture is concentrated, and the residue is dissolved in 1N HCl and extracted with EtOAc. The organic layer is washed with brine, dried over sodium sulfate, and concentrated. The residue is purified by flash column chromatography on silica gel (0 to 40% EtOAc in heptane) to provide 2-[2-(4-bromo-phenyl)-2-hydroxy-ethoxy]-5-fluoro-phenol (G-3).

Triphenylphosphine (918 mg, 3.5 mmol) is dissolved in THF (25 mL) and cooled to 0° C. Diisopropyl azodicarboxylate (0.7 mL, 3.5 mmol.) is added to the mixture and stirred at 0° C. for 20 minutes. The mixture is then treated dropwise over 5 minutes with a solution of G-3(1.1 g, 3.33 mmol) in THF (10 mL), and the resulting mixture is stirred at 0° C. for 30 minutes and at room temperature for 30 minutes. The reaction mixture is concentrated, and the residue is purified by flash column chromatography on silica gel (0 to 40% EtOAc in heptane) to give 2-(4-bromo-phenyl)-7-fluoro-2,3-dihydro-benzo[1,4]dioxine (G-4).

A solution of G-4 (200 mg, 0.65 mmol), potassium (morpholin-4-yl)methyltrifluoroborate (134 mg, 0.65 mmol), palladium(II) acetate (4.3 mg, 0.019 mmol), 2-dicyclohexylphosphino-2',4',6'-tri-isopropyl-1,1'-biphenyl (19 mg, 0.039 mmol), and cesium carbonate (632 mg, 1.9 mmol) in 10:1 THF/water (2 mL) is stirred at 95° C. for 18 h under an atmosphere of nitrogen. The mixture is taken up in EtOAc, and the organic layer is washed with water, brine, dried over $Na_2SO_4$, and concentrated. The residue is purified by preparative C18 reversed phase HPLC (MeCN/water; 0.1% TFA) to give the title compound. LC/MS Method 10; Rt=1.09 min.; $[M+H]^+$=354.4.

Example 203

Preparation of 1-[4-(7-Fluoro-2,3-dihydro-benzo[1,4]dioxin-2-yl)-benzyl]-pyrrolidine (203)

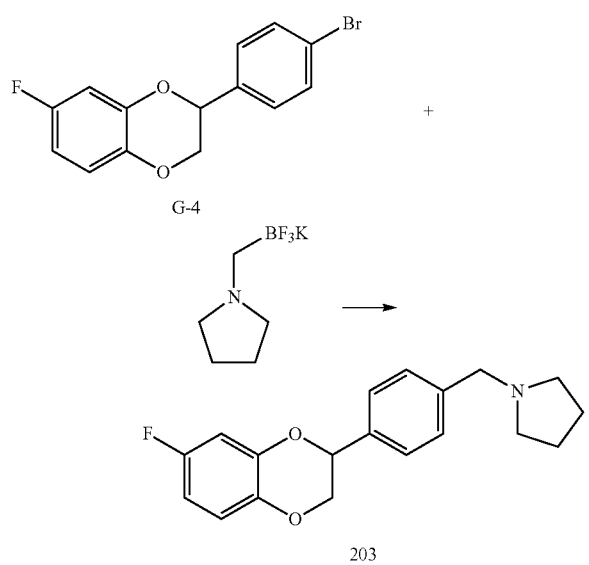

The title compound is prepared from G-4 and Potassium 1-trifluoroboratomethylpyrrolidine according to the procedure described for the synthesis of compound 202. 203: LC/MS Method 10; Rt=1.07 min.; [M+H]$^+$=354.4.

Examples 204 and 205

Preparation of (S)-3-(4-Morpholin-4-ylmethyl-phenyl)-2,3-dihydro-[1,4]dioxino[2,3-b]pyridine (204) and (R)-3-(4-Morpholin-4-ylmethyl-phenyl)-2,3-dihydro-[1,4]dioxino[2,3-b]pyridine (205)

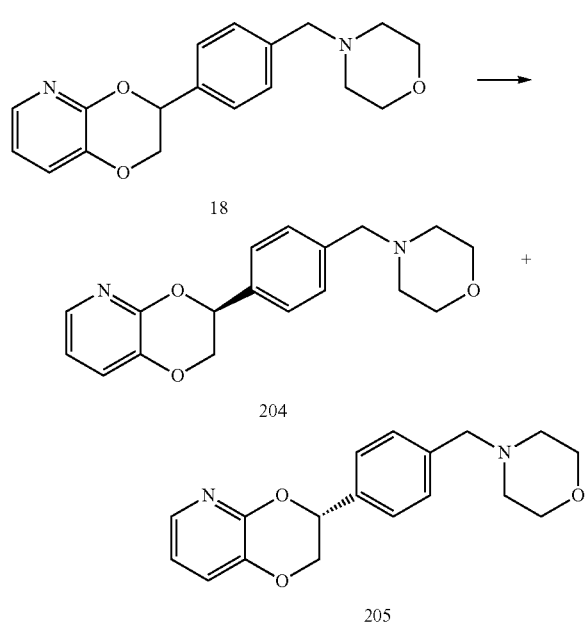

Compound 18 (racemate) is resolved by HPLC using a Chiralcel OD-H column eluting with 28% isopropanol in heptane to give compound 204 (LCMS method 15: ES$^+$ m/z 313.2 [M+H]$^+$, rt=0.47 min) and compound 205 (LCMS method 15: ES$^+$ m/z 313.2 [M+H]$^+$, rt=0.50 min)

Examples 206 and 207

Preparation of 1-{4-[(3S)-2,3-dihydro[1,4]dioxino[2,3-b]pyridin-3-yl]benzyl}piperidine-4-carboxamide (206) and 1-{4-[(3R)-2,3-dihydro[1,4]dioxino[2,3-b]pyridin-3-yl]benzyl}piperidine-4-carboxamide (207)

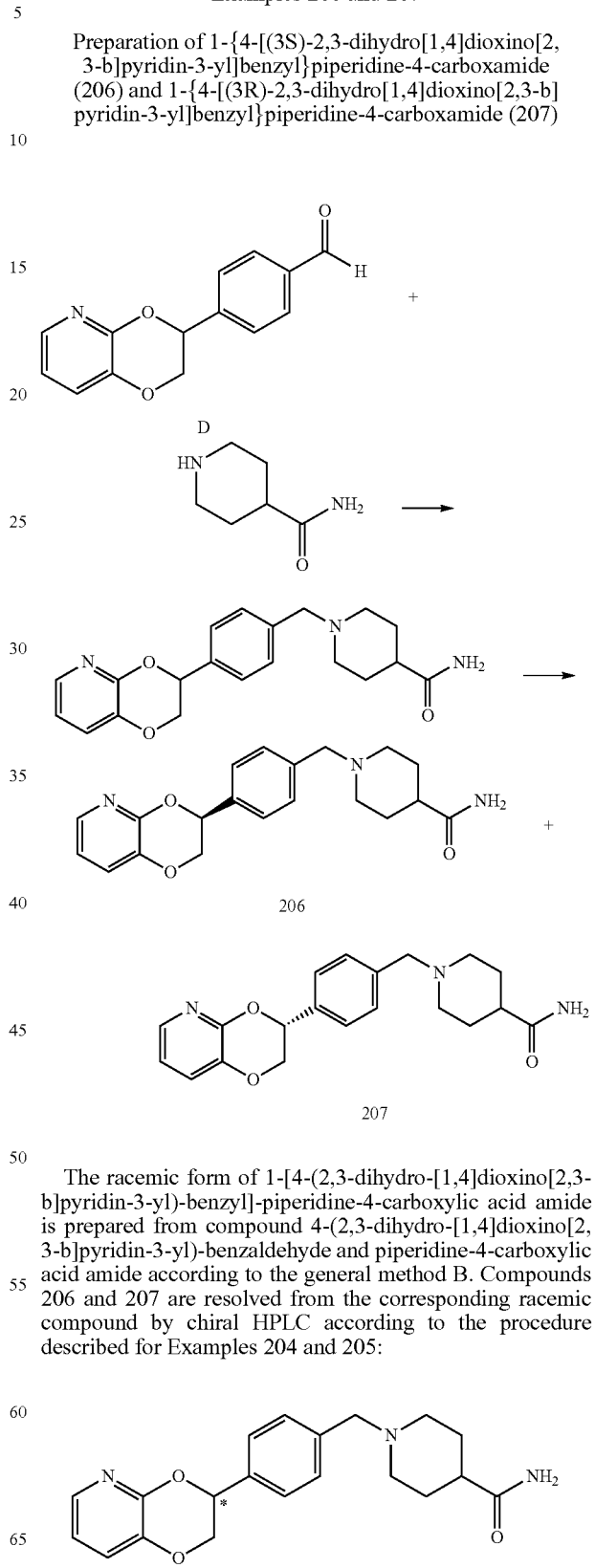

The racemic form of 1-[4-(2,3-dihydro-[1,4]dioxino[2,3-b]pyridin-3-yl)-benzyl]-piperidine-4-carboxylic acid amide is prepared from compound 4-(2,3-dihydro-[1,4]dioxino[2,3-b]pyridin-3-yl)-benzaldehyde and piperidine-4-carboxylic acid amide according to the general method B. Compounds 206 and 207 are resolved from the corresponding racemic compound by chiral HPLC according to the procedure described for Examples 204 and 205:

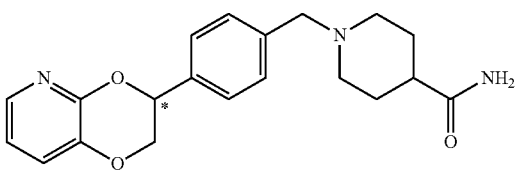 [SMILES: NC(=O)C1CCN(Cc2ccc(C3COc4cccnc4O3)cc2)CC1]

TABLE 4

Preparation of compounds 206 and 207.

| Ex # | Chirality at * | MS Method | [M + H]+ | rt (min) |
|---|---|---|---|---|
| 206 | S | 15 | 354.2 | 0.47 |
| 207 | R | 15 | 354.2 | 0.45 |

Example 208

Preparation of 11-[4-(2,3-dihydro-[1,4]dioxino[2,3-b]pyridin-3-yl)-benzyl]-pyrrolidin-2-one (208)

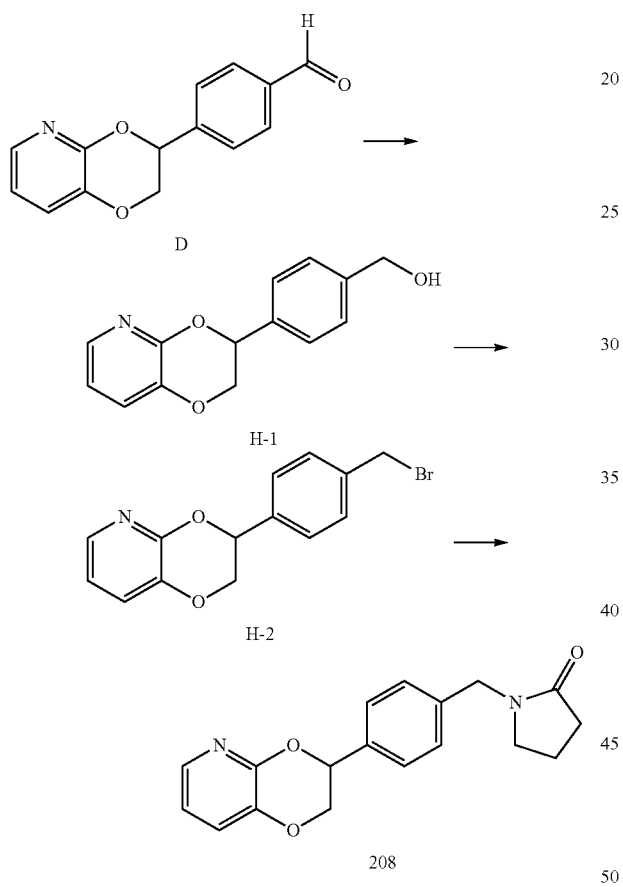

A solution of D (1.0 g, 4.15 mmol) in THF (50 mL) is treated with sodium borohydride (188 mg, 5.00 mmol) at 0° C. The resulting mixture is allowed to warm to room temperature and stirred at room temperature for 1 h. The reaction mixture is concentrated and the residue dissolved in EtOAc. The organic solution is washed with water and brine, dried over sodium sulfate, and concentrated. The residue is purified by flash column chromatography (silica gel) with MeOH in DCM (from 2% to 8%) to give [4-(2,3-dihydro-[1,4]dioxino[2,3-b]pyridin-3-yl)-phenyl]-methanol H-1.

A solution of H-1 (400 mg, 1.64 mmol) in THF (10 mL) is treated with triphenylphosphine dibromide (1.39 g, 3.29 mmol) and imidazole (224 mg, 3.29 mmol) at room temperature, and the resulting mixture is stirred at room temperature for 72 h. The mixture is diluted with water and extracted with EtOAc (25 mL, 3×). The combined organic layers are washed with brine, dried over sodium sulfate, and concentrated. The residue is purified by flash column chromatography (silica gel) with EtOAc in heptane (from 15% to 50%) to give 3-(4-Bromomethyl-phenyl)-2,3-dihydro[1,4]dioxino[2,3-b]pyridine H-2.

A solution of pyrrolidinone (18 mg, 0.21 mmol) in anhydrous DMF (2 mL) is treated with sodium hydride (60% dispersion in mineral oil, 7.8 mg, 0.2 mmol), and the mixture is stirred at room temperature for 15 minutes. Intermediate H-2 (50 mg, 0.16 mmol) is added, and the mixture is stirred at 50° C. After 15 minutes, the mixture is quenched with water and extracted with EtOAc. The organic layer is concentrated, and the residue is purified by reversed phase HPLC eluting with a gradient of 5-85% of MeCN in $H_2O$ (+0.1% TFA). The desired fractions are concentrated. The residue is dissolved in EtOAc, washed with saturated aqueous $NaHCO_3$, brine, and dried over $Na_2SO_4$. The solution is then filtered and concentrated to give the title compound as a solid (LCMS method 10: $ES^+$ m/z 311.4 $[M+H]^+$, Rt=1.84 min)

Example 209

3-[4-(2,3-dihydro[1,4]dioxino[2,3-b]pyridin-3-yl)benzyl]-1,3-oxazolidin-2-one (209)

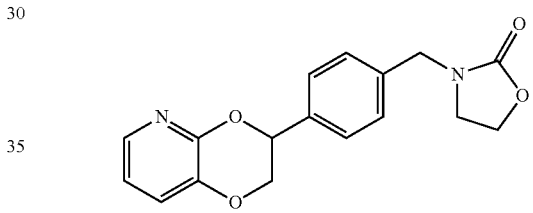

Compound 209 is prepared from intermediate H-2 according to the procedure described for the synthesis of 208. (LCMS method 10: $ES^+$ m/z 313.4 $[M+H]^+$, Rt=1.72 min)

Example 210

Preparation of 4-(2,3-Dihydro-[1,4]dioxino[2,3-b]pyridin-3-yl)-benzylamine (210)

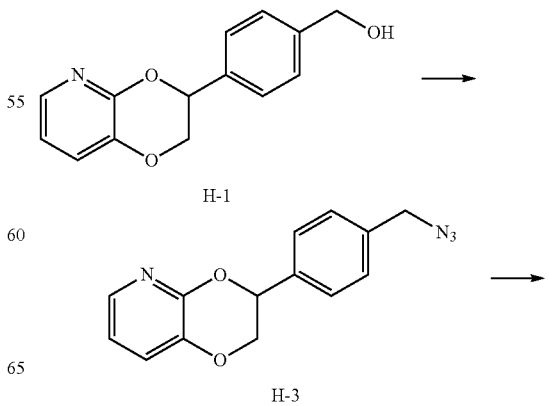

-continued

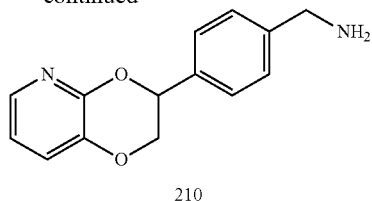

210

A solution of H-1 (340 mg, 1.4 mmol), triphenylphosphine (550 mg, 2.1 mmol) and diphenylphosphophyl azide (0.45 mL, 2.1 mmol) in anhydrous THF (30 mL) is treated with diisopropyl azodicarboxylate (0.41 mL, 2.1 mmol). The reaction is stirred at room temperature for 24 hours, diluted with water (50 mL), and extracted with EtOAc (3×50 mL). The combined organic solution is washed with brine, dried over $Na_2SO_4$, filtered and concentrated. The residue is purified by flash chromatography eluting with a gradient of 10-50% EtOAc in Heptane to give H-3 as an oil.

A solution of H-3 (390 mg, 78% pure, 1.1 mmol) and triphenylphosphine (446 mg, 1.7 mmol) in THF (20 mL) is treated with water (0.2 mL, 11.3 mmol). The mixture is stirred at 40° C. for 24 hours, cooled to room temperature, diluted with water (25 mL), and extracted with EtOAc (3×25 mL). The combined organic solution is washed with brine, dried over $Na_2SO_4$, filtered, and concentrated. The residue is purified by reversed phase HPLC eluting with a gradient of 5-85% MeCN in $H_2O$ (+0.1% TFA). The combined fractions is concentrated, basified with saturated aqueous $NaHCO_3$ (10 mL), and extracted with EtOAc (10 mL×3). The combined organic phase is washed with brine, dried over $Na_2SO_4$, and concentrated to give the title compound as a solid (LCMS method 10: $ES^+$ m/z 243.4 $[M+H]^+$, Rt=0.57 min).

Example 211

Preparation of 1-[(S)-4-(2,3-Dihydro-benzo[1,4]dioxin-2-yl)-benzyl]-4-methyl-piperidine-4-carboxylic acid (211)

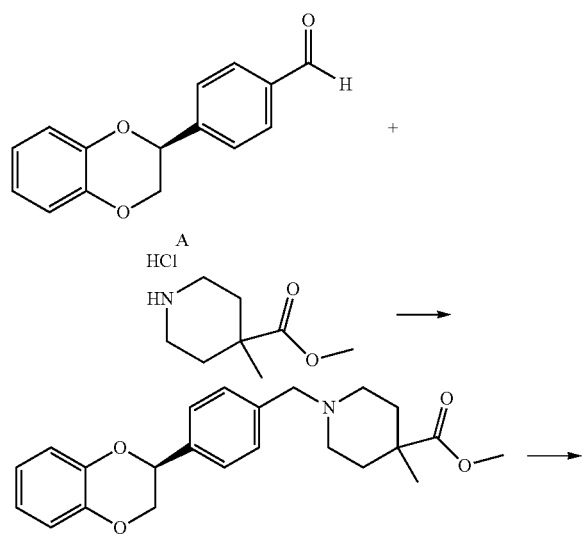

-continued

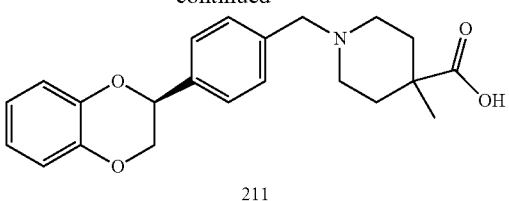

211

Intermediate A (100 mg, 0.42 mmol), methyl-piperidine-4-carboxylic acid methyl ester hydrochloride (105 mg, 0.54 mmol), and TEA (75 uL, 0.54 mmol) are stirred in dry THF (3 mL) for 10 minutes. Sodium triacetoxyborohydride (176 mg) is added and stirred for 4 h. The mixture is diluted with saturated $NaHCO_3$ and extracted with EtOAc. The organic layer is washed with brine, dried over $Na_2SO_4$, filtered, and concentrated. The residue is purified by flash chromatography eluting with a gradient of 0-3% MeOH in DCM to give [(S)-4-(2,3-dihydro-benzo[1,4]dioxin-2-yl)-benzyl]-4-methyl-piperidine-4-carboxylic acid methyl ester.

A solution of 1-[(S)-4-(2,3-dihydro-benzo[1,4]dioxin-2-yl)-benzyl]-4-methyl-piperidine-4-carboxylic acid methyl ester in MeOH (2 mL) is treated with a solution of $LiOH.H_2O$ (52 mg, 1.23 mmol) in water (2 mL). The mixture is heated to 70° C. for 2 h, concentrated, and treated with TFA (96 uL, 1.23 mmol). The mixture is diluted with water and extracted with EtOAc/THF. The organic layer is dried over $Na_2SO_4$, filtered through Diatomaceous earth, and concentrated. The residue is purified by reversed phase HPLC eluting with a gradient of 5-80% MeCN in water (+0.1% TFA) to provide the title compound as the TFA salt (LC/MS method 1: $ES^+$ m/z 368.23 $[M+H]^+$; Rt=0.62 min).

Examples 212-215

Preparation of Compounds 212-215

Compounds 212-215 are prepared from intermediates I-2, I-3, I-5 and I-6 according to the procedure described for the synthesis of compound 211 and shown in Table 5.

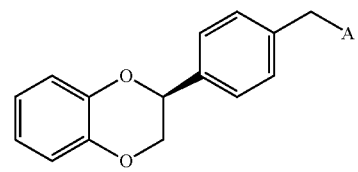

TABLE 5

Preparation of compounds 212-215.

| Ex # | —A | MS Method | $[M + H]^+$ | Rt (min) |
|---|---|---|---|---|
| 212 | cis 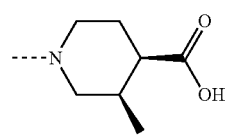 | 1 | 368.24 | 0.62 |

TABLE 5-continued

Preparation of compounds 212-215.

| Ex # | —A | MS Method | [M + H]+ | Rt (min) |
|---|---|---|---|---|
| 213 | | 1 | 372.20 | 0.61 |
| 214 | | 1 | 341.20 | 0.61 |
| 215 | | 1 | 341.23 | 0.58 |

Example 216

Preparation of, 1-[(S)-4-(2,3-Dihydro-benzo[1,4]
dioxin-2-yl)-benzyl]-4-(1H-tetrazol-5-yl)-piperidine
(216)

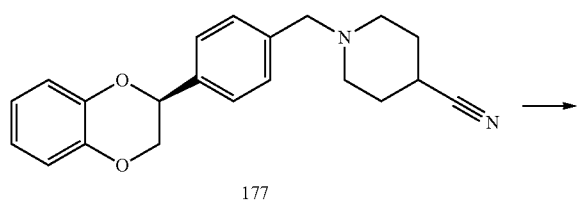

To a solution of 177 (115 mg, 0.34 mmol) in DMF (2 mL) is added NaN$_3$ (89.0 mg, 1.38 mmol) and NH$_4$Cl (147 mg, 2.75 mmol). The mixture is heated at 120° C. for 18 h. Additional NaN$_3$ (89.0 mg, 1.38 mmol) is added, and the reaction is stirred at 120° C. for an additional 72 h. The reaction is filtered, and the filtrate is purified by reversed phase HPLC eluting with a gradient of 5-80% MeCN in water (+0.1% TFA to provide the title compound (LC/MS method 1: ES+ m/z 378.2 [M+H]+; Rt=0.54 min).

Example 217

Preparation of 1-[(S)-4-(2,3-Dihydro-benzo[1,4]
dioxin-2-yl)-benzyl]-piperidin-4-ylamine (217)

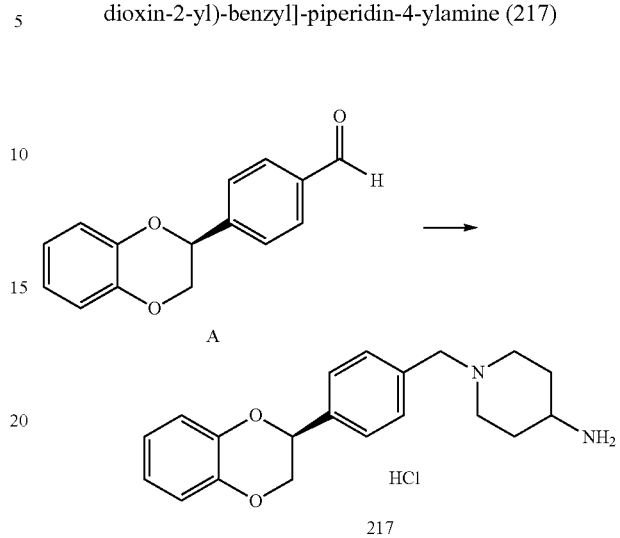

A solution of intermediate A (300 mg, 1.25 mmol) and piperidin-4-yl-carbamic acid tert-butyl ester (300 mg, 1.5 mmol, 1.2 equiv.) is stirred in dry THF (3 mL) for 10 minutes. Sodium triacetoxyborohydride (316 mg, 1.49 mmol) is added, and the reaction is stirred for 18 h. The reaction is concentrated and partitioned between EtOAc and saturated aqueous NaHCO$_3$. The organic layer is dried over Na$_2$SO$_4$, filtered, and concentrated. The residue is purified by flash chromatography eluting with a gradient of 0-5% MeOH in DCM. The residue is dissolved in MeOH (1 mL), treated with HCl (10 mL, 4M in dioxane), and stirred for 18 h. The reaction is diluted with Et$_2$O (40 mL) and filtered to provide the title compound as the HCl salt (LC/MS method 1: ES+ m/z 325.2 [M+H]+, Rt=0.35 min).

Example 218

Preparation of N-{1-[(S)-4-(2,3-Dihydro-benzo[1,4]
dioxin-2-yl)-benzyl]-piperidin-4-yl}-2-hydroxy-
acetamide (218)

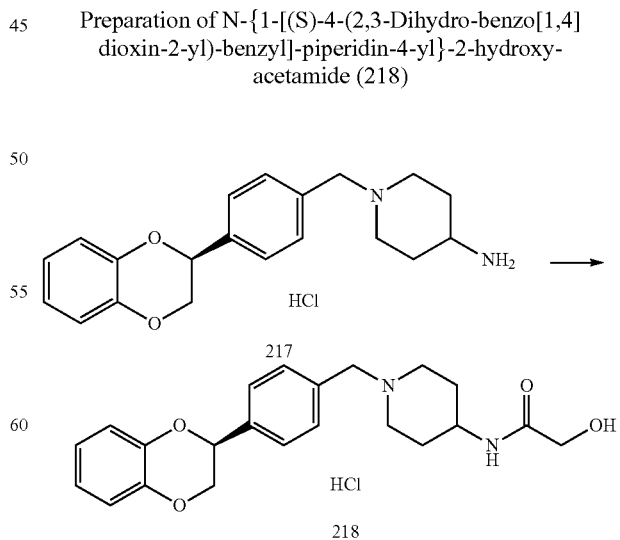

A solution of compound 217 (80 mg, 0.22 mmol), TEA (0.09 mL, 0.67 mmol), hydroxyacetic acid (22 mg, 0.29 mmol) and TBTU (93 mg, 0.29 mmol) in DMF (2 mL) is stirred for 2 h. The reaction is filtered and purified by reversed phase HPLC eluting with a gradient of 0-80% MeCN in water (+0.1% TFA) to provide the title compound as a TFA salt (LC/MS method 1: ES+ m/z 383.2 [M+H]$^+$, Rt=0.59 min).

Example 219-220

Preparation of N-(1-{4-[(2S)-2,3-dihydro-1,4-benzodioxin-2-yl]benzyl}piperidin-4-yl)-2-methoxyacetamide (219) and N-(1-{4-[(2S)-2,3-dihydro-1,4-benzodioxin-2-yl]benzyl}piperidin-4-yl)-2-hydroxy-2-methylpropanamide (220)

Compounds 219 through 223 are prepared and according to the procedure described for compound 218 and shown in Table 6. The products are purified by reversed phase HPLC or flash chromatography eluting with a gradient of 0-10% MeOH in DCM.

TABLE 6

Preparation of compounds 219-223.

| Ex # | X | —R$^6$ | MS Method | [M + H]$^+$ | Rt (min) |
|---|---|---|---|---|---|
| 219 | CH | acetyl-CH$_2$-OCH$_3$ | 1 | 397.08 | 0.61 |
| 220 | CH | acetyl-C(CH$_3$)$_2$-OH | 1 | 411.30 | 0.55 |
| 221 | N | acetyl-C(CH$_3$)$_2$-OH | 1 | 412.27 | 0.48 |
| 222 | N | acetyl-CH$_2$-OH | 1 | 384.22 | 0.43 |
| 223 | N | acetyl-C(cyclopropyl)-OH | 1 | 410.26 | 0.47 |

Example 224

Preparation of 1-[(S)-4-(2,3-Dihydro-benzo[1,4]dioxin-2-yl)-benzyl]-4-(1,1-dioxo-1λ$^6$-isothiazolidin-2-yl)-piperidine (224)

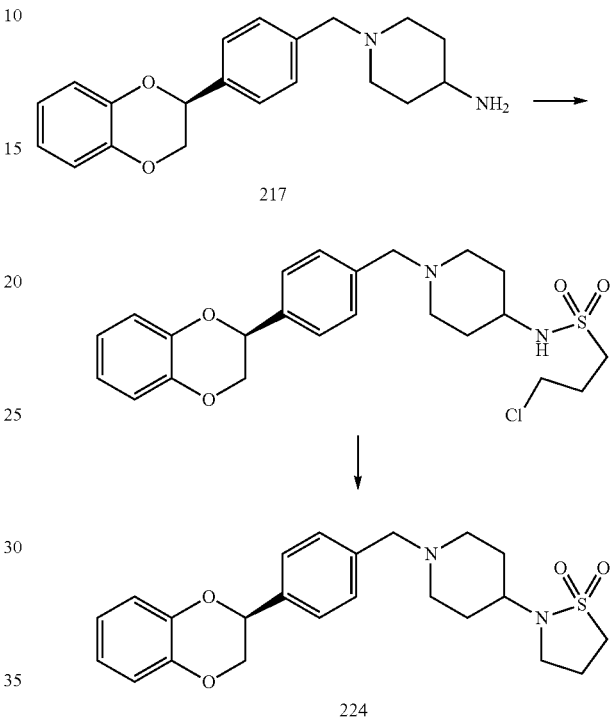

To a stirred solution of compound 217 (535 mg, 1.65 mmol) in THF (10 mL) is added 3-chloro-propane-1-sulfonyl chloride (0.40 mL, 3.3 mmol) and pyridine (0.27 mL). After 18 h, the mixture is diluted with saturated NaHCO$_3$ and extracted with EtOAc. The organic layer is dried over Na$_2$SO$_4$, filtered, and concentrated. The residue is purified by flash chromatography eluting with a gradient of 0-10% MeOH in DCM to provide 3-chloro-propane-1-sulfonic acid {1-[(S)-4-(2,3-dihydro-benzo[1,4]dioxin-2-yl)-benzyl]-piperidin-4-yl}-amide. LC/MS method 1: ES+ m/z 465.2 [M]$^+$, Rt=0.68 min).

To a solution of 3-chloro-propane-1-sulfonic acid {1-[(S)-4-(2,3-dihydro-benzo[1,4]dioxin-2-yl)-benzyl]-piperidin-4-yl}-amide (410 mg, 0.88 mmol) in DMF (5 mL) is added NaH (60% dispersion in mineral oil, 71 mg, 1.8 mmol). The reaction is heated to 80° C. for 1 h, diluted with EtOAc, washed with water and brine, dried over Na$_2$SO$_4$, filtered, and concentrated. The residue is purified by reversed phase HPLC eluting with a gradient of 0-80% MeCN in water (+0.1% TFA). The desired fractions are lyophilized, partitioned between saturated aqueous NaHCO$_3$ and EtOAc. The organic layer is dried over Na$_2$SO$_4$, filtered and concentrated to provide the title compound (LC/MS method 1: ES+ m/z 429.4 [M+H]$^+$, Rt=0.63 min).

Example 225

Preparation of 1-{1-[(S)-4-(2,3-dihydro-benzo[1,4]dioxin-2-yl)-phenyl]-ethyl}-pyrrolidine (225)

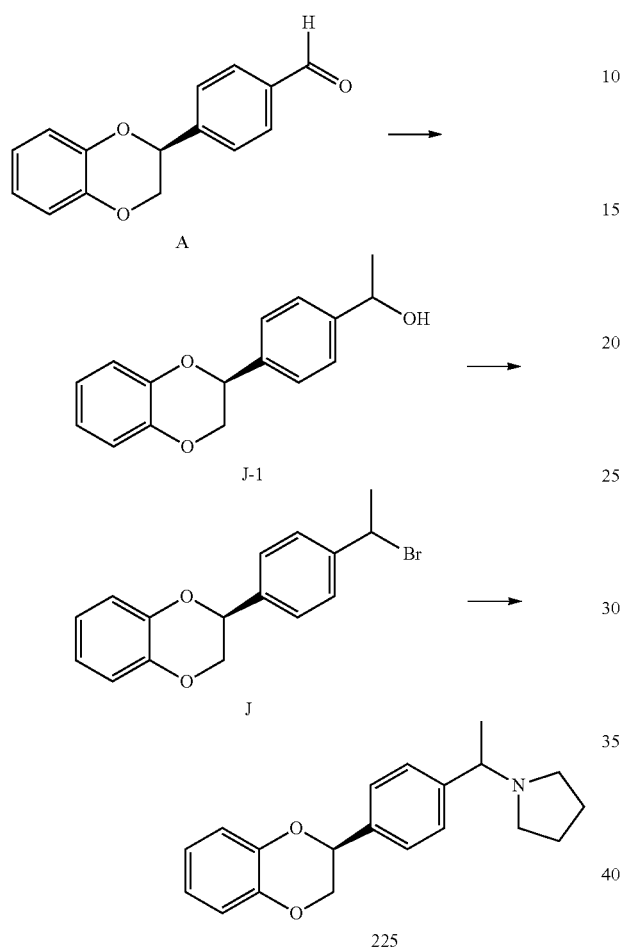

A solution of A (1.0 g, 4.16 mmol) in THF (10 mL) is treated with 1.4M methylmagnesium bromide solution in toluene at 0° C. The resulting mixture is stirred at 0° C. for 1 h. The mixture is then quenched with saturated ammonium chloride solution and extracted with EtOAc. The organic solution is dried over Na$_2$SO$_4$, filtered, and concentrated. The residue is purified by flash chromatography eluting with a gradient of 0-30% EtOAc in heptane to give 1-[(S)-4-(2,3-dihydro-benzo[1,4]dioxin-2-yl)-phenyl]-ethanol (J-1).

A solution of J-1 (500 mg, 1.95 mmol) in THF (10 mL) is treated with triphenylphosphine dibromide (1.65 g, 3.90 mmol) and imidazole (265 mg, 3.90 mmol) at room temperature, and the resulting mixture is stirred at room temperature for 72 h. The mixture is diluted with water and extracted with EtOAc (25 mL, 3×). The combined organic layers are washed with brine, dried over sodium sulfate, and concentrated. The residue is purified by flash column chromatography (silica gel) with EtOAc in Heptane (from 0% to 30%) to give (S)-2-[4-(1-bromo-ethyl)-phenyl]-2,3-dihydro-benzo[1,4]dioxine J.

A mixture of intermediate J (560 mg, 90% pure, 1.58 mmol) in pyrrolidine (0.5 mL) is heated at 60° C. for 18 h. The reaction is diluted with MeOH and purified by reversed phase HPLC eluting with a gradient of 5-80% MeCN in water (+0.1% TFA). The desired fractions are combined, diluted with EtOAc, and washed with saturated aqueous NaHCO$_3$. The organic layer is dried over Na$_2$SO$_4$, filtered, and concentrated. The residue is dissolved in Et$_2$O (2 mL), treated with HCl (2 mL, 2M in Et$_2$O), and concentrated to provide the title product as the HCl salt (LC/MS method 1: ES+ m/z 311.2 [M+H]$^+$, Rt=0.63 min).

Example 226

4-(1-{4-[(2S)-2,3-dihydro-1,4-benzodioxin-2-yl]phenyl}ethyl)morpholine (226)

Compound 226 is prepared from intermediate J and morpholine according to the procedure described for the synthesis of compound 225.

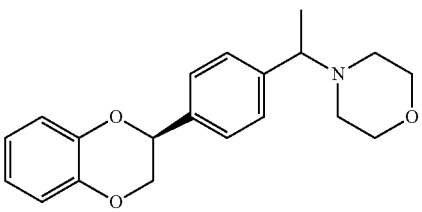 [SMILES: CC(c1ccc([C@H]2COc3ccccc3O2)cc1)N1CCOCC1]

| Ex # | MS Method | [M + H]$^+$ | Rt (min) |
|---|---|---|---|
| 226 | 1 | 327.20 | 0.89 |

Example 227

Preparation of 1-{1-[(S)-4-(2,3-dihydro-benzo[1,4]dioxin-2-yl)-phenyl]-ethyl}-piperidine-4-carboxylic acid (227)

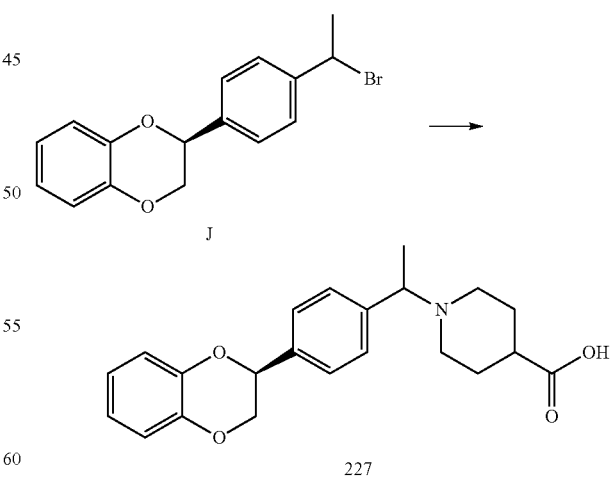

A mixture of intermediate J (188 mg, 0.59 mmol) and piperidine-4-carboxylic acid ethyl ester (0.5 mL, 3.24 mmol) is heated at 60° C. for 18 h. The reaction is diluted with MeOH and purified by reversed phase HPLC eluting with a gradient of 5-80% CH$_3$CN in water (+0.1% TFA). The desired fractions are combined, diluted with EtOAc, and washed with saturated aqueous NaHCO$_3$. The organic layer is dried over Na$_2$SO$_4$, filtered, and concentrated. The residue is dissolved in a mixture of MeOH (4 mL) and water (4 mL) containing KOH (110 mg, 2 mmol) and heated at 50° C. for 18 h. The mixture is concentrated, treated with TFA (0.15 mL, 2 mmol), and extracted with EtOAc. The organic layer is dried over Na$_2$SO$_4$, filtered, and concentrated to provide the title compound as the TFA salt (LCMS method 7: ES+ m/z 369.2 [M+H]$^+$, Rt=0.56 min).

Example 228

Preparation of 1-[(S)-4-(2,3-Dihydro-[1,4]dioxino[2,3-b]pyridin-3-yl)-benzyl]-4-methyl-piperidine-4-carboxylic acid formate salt (228)

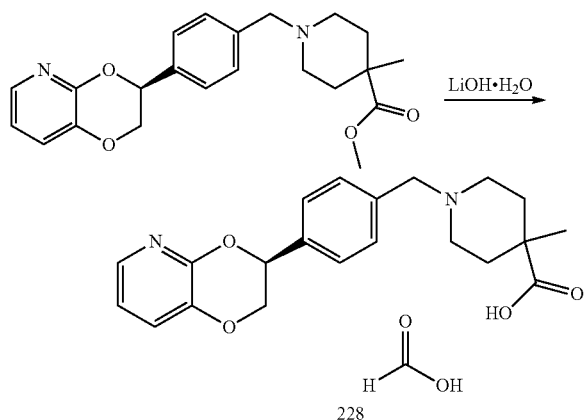

228

A mixture of 1-[(S)-4-(2,3-Dihydro-[1,4]dioxino[2,3-b]pyridin-3-yl)-benzyl]-4-methyl-piperidine-4-carboxylic acid methyl ester (prepared according to the General Method A) (43 mg, 0.10 mmol), LiOH.H$_2$O (21 mg, 0.5 mmol), MeOH (3 mL), and water (1 mL) is warmed to 50° C. overnight. The reaction is concentrated, neutralized with 1 N aqueous HCl, and purified by reversed phase HPLC eluting with a gradient of 0-70% MeCN in water (+0.1% formic acid) to afford the title compound as the formate salt (LCMS method 15: ES+ m/z 382.8 [M+H]$^+$, Rt=0.54 min).

Example 229

Preparation of 2-{1-[(S)-4-(2,3-Dihydro-benzo[1,4]dioxin-2-yl)-benzyl]-piperidin-4-yl}-2-methyl-propionic acid formate salt (229)

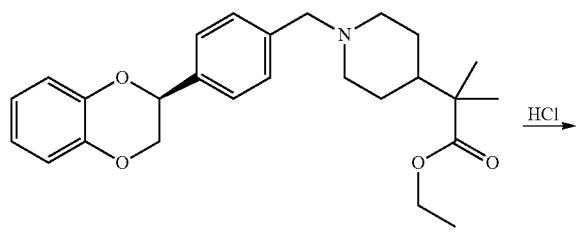

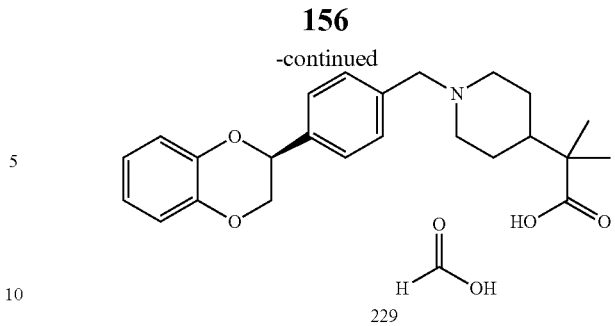

229

2-{1-[(S)-4-(2,3-Dihydro-benzo[1,4]dioxin-2-yl)-benzyl]-piperidin-4-yl}-2-methyl-propionic acid ethyl ester (prepared according to General Method A) (226 mg, 0.430 mmol) is treated with HCl (1.5 mL, 4M in dioxane, 6 mmol) and 1 mL of water. The mixture is warmed to 140° C. for 1 hour, concentrated, diluted with water, and neutralized with 2N aqueous Na$_2$CO$_3$. The aqueous layer is decanted and the remaining residue is purified by reversed phase HPLC eluting with a gradient of 0-70% MeCN in water (+0.1% formic acid) to afford the title compound as the formate salt (LCMS method 15: ES+ m/z 395.8 [M+H]$^+$, Rt=1.25 min).

Example 230

Preparation of 2-{1-[(S)-4-(2,3-Dihydro-[1,4]dioxino[2,3-b]pyridin-3-yl)-benzyl]-piperidin-4-yl}-2-methyl-propionic acid formate salt (230)

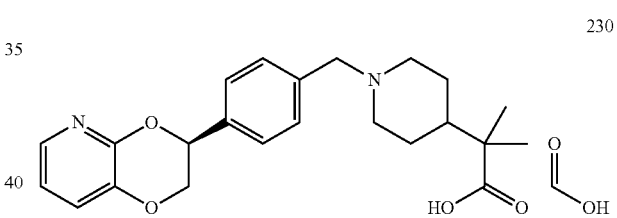

230

Compound 230 is prepared according to the procedure described for the synthesis of compound 229.

Example 231

Preparation of 4-{1-[(S)-4-(2,3-Dihydro-benzo[1,4]dioxin-2-yl)-benzyl]-piperidin-4-ylmethyl}-benzoic acid (231)

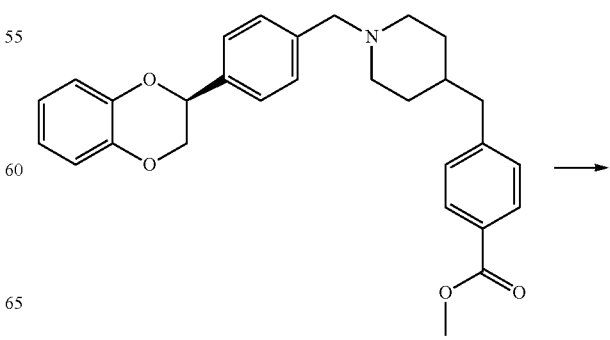

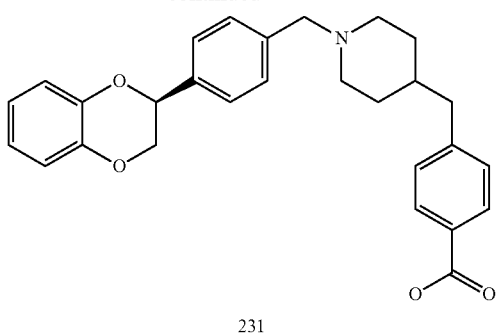

231

A mixture of 4-{1-[(S)-4-(2,3-dihydro-benzo[1,4]dioxin-2-yl)-benzyl]-piperidin-4-ylmethyl}-benzoic acid methyl ester (prepared according to General Method C) (80 mg, 0.17 mmol), LiOH.H$_2$O (15 mg, 0.36 mmol), MeOH (3 mL) and water (0.5 mL) is stirred at room temperature for 16 h. The reaction mixture is neutralized with acetic acid and concentrated. The residue is triturated with water to give the title compound.

Examples 231-235

Preparation of Compounds 231-235

Compounds 231-235 are prepared according to the procedure described for the synthesis of compound 231 as shown in Table 7 below.

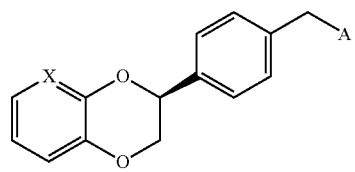

TABLE 7

| Preparation of compounds 231-235. | | | | | |
|---|---|---|---|---|---|
| Ex # | X | —A | MS Method | [M + H]⁺ | Rt (min) |
| 231 | CH | ![structure] | 4 | 444.30 | 1.42 |
| 232 | CH | ![structure] | 4 | 402.25 | 1.28 |
| 233 | CH | ![structure] | 4 | 430.26 | 1.21 |

TABLE 7-continued

| Preparation of compounds 231-235. | | | | | |
|---|---|---|---|---|---|
| Ex # | X | —A | MS Method | [M + H]⁺ | Rt (min) |
| 234 | N | ![structure] | 4 | 445.29 | 0.81 |
| 235 | N | ![structure] | 3 | 431.25 | 1.59 |

Example 236

Preparation of 4-({[(S)-4-(2,3-Dihydro-benzo[1,4]dioxin-2-yl)-benzyl]-ethyl-amino}-methyl)-benzoic acid (236)

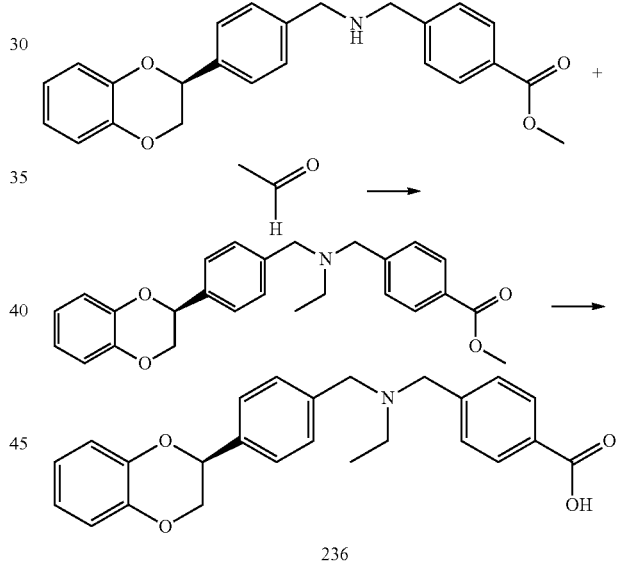

236

A mixture of 4-{[(S)-4-(2,3-dihydro-benzo[1,4]dioxin-2-yl)-benzylamino]-methyl}-benzoic acid methyl ester (prepared according to General Method E) (130 mg, 0.33 mmol), acetaldehyde (0.03 mL, 0.50 mmol), and sodium cyanoborohydride (42 mg, 0.67 mmol) in MeOH (15 mL) is treated with 2 drops of acetic acid. The mixture is stirred at room temperature for 16 h, and concentrated. The residue is purified by flash chromatography eluting with a gradient of 0-10% MeOH in DCM to give 4-({[(S)-4-(2,3-dihydro-benzo[1,4]dioxin-2-yl)-benzyl]-ethyl-amino}-methyl)-benzoic acid methyl ester.

A mixture of 4-({[(S)-4-(2,3-dihydro-benzo[1,4]dioxin-2-yl)-benzyl]-ethyl-amino}-methyl)-benzoic acid methyl ester (65 mg, 0.16 mmol), LiOH.H$_2$O (23 mg, 0.55 mmol), MeOH (5 mL) and water (0.5 mL) is stirred at room temperature for 16 h. The reaction mixture is neutralized with acetic acid and concentrated. The residue is diluted with water and DCM, phases are separated, the organic layer is dried over Na₂SO₄, filtered and concentrated. The residue is purified by flash chromatography eluting with a gradient of 0-10% MeOH in DCM to give the title compound.

Examples 236-238

Preparation of Compounds 236-238

Compounds 236-238 are prepared according to the procedure described for the synthesis of compound 236 and as shown in Table 8 below.

TABLE 8

Preparation of compounds 236-238.

| Ex # | X | —A | MS Method | [M + H]⁺ | Rt (min) |
|---|---|---|---|---|---|
| 236 | CH | 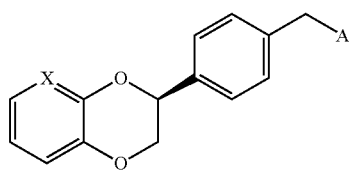 | 3 | 404.40 | 1.86 |
| 237 | CH | (N-butyl analog with benzoic acid) | 3 | 432.29 | 2.29 |
| 238 | CH | (N-ethyl 3-benzoic acid analog) | 3 | 404.26 | 1.98 |

Example 239

Preparation of 3-{4-[(S)-4-(2,3-Dihydro-benzo[1,4]dioxin-2-yl)-benzyl]-piperazin-1-ylmethyl}-benzoic acid (239)

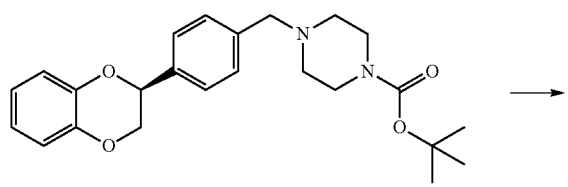

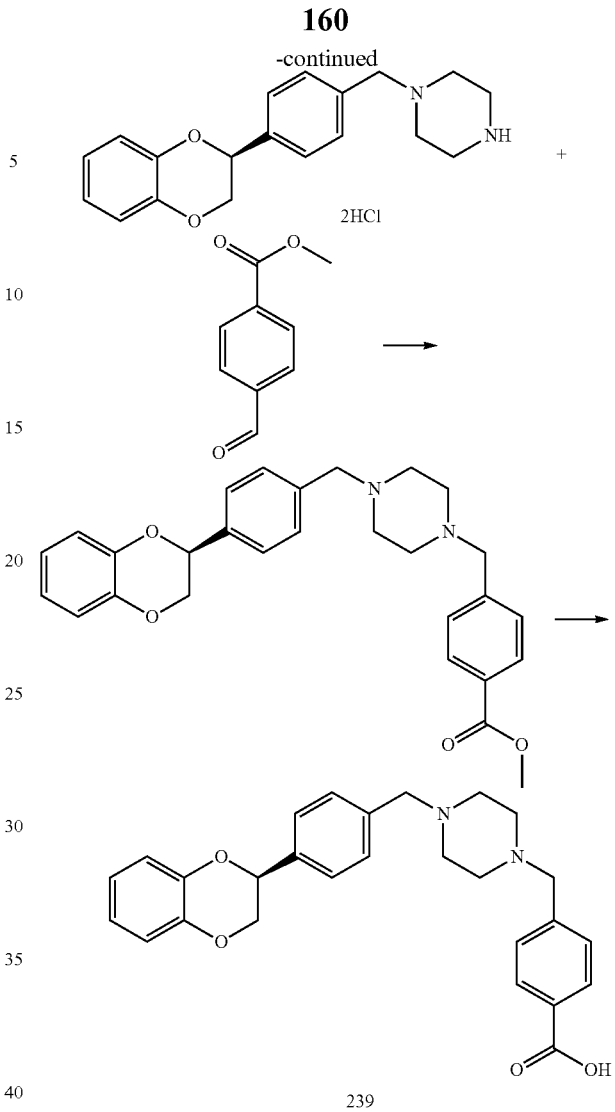

Methanol (30 mL) is added dropwise to acetyl chloride (1.4 mL) at 0° C. The solution is added to 4-[(S)-4-(2,3-dihydrobenzo[1,4]dioxin-2-yl)-benzyl]-piperazine-1-carboxylic acid tert-butyl ester (408 mg, 0.99 mmol) (prepared according to the General Method E). The resulting mixture is stirred at room temperature for 16 h and concentrated. The residue is suspended in a mixture of heptane and EtOAc, and the precipitate is collected and dried under vacuum to give 1-[(S)-4-(2,3-dihydro-benzo[1,4]dioxin-2-yl)-benzyl]-piperazine dihydrochloride.

A solution of 1-[(S)-4-(2,3-dihydro-benzo[1,4]dioxin-2-yl)-benzyl]-piperazine dihydrochloride (80 mg, 0.21 mmol), 4-formyl-benzoic acid methyl ester (41 mg, 0.25 mmol), sodium cyanoborohydride (26 mg, 0.42 mmol), and DIPEA (0.07 mL, 0.42 mmol) in MeOH (5 mL) is treated with 2 drops of acetic acid. The resulting mixture is stirred at room temperature for 16 h, concentrated, diluted with water, and extracted with ethyl acetate. The organic layer is washed with brine, dried over Na₂SO₄, filtered, and concentrated. The residue is purified by flash chromatography eluting with a gradient of 0-10% MeOH in DCM to give 4-{4-[(S)-4-(2,3-dihydro-benzo[1,4]dioxin-2-yl)-benzyl]-piperazin-1-ylmethyl}-benzoic acid methyl ester.

A mixture of 4-{4-[(S)-4-(2,3-dihydro-benzo[1,4]dioxin-2-yl)-benzyl]-piperazin-1-ylmethyl}-benzoic acid methyl ester (48 mg, 0.11 mmol), LiOH.H$_2$O (15 mg, 0.37 mmol), dioxane (5 mL), and water (0.5 mL) is stirred at room temperature for 16 h. The reaction mixture is neutralized with acetic acid and concentrated. The residue is triturated with water to give the title compound (LCMS method 4: ES+ m/z 445.2 [M+H]$^+$, Rt=1.31 min).

Assessment of Biological Properties

The compounds of the invention are assessed for the ability to interact with human LTA$_4$ hydrolase in an enzymatic assay that measures the ability of the enzyme to cleave the peptide bond of arginyl-aminomethylcoumarin (Arg-AMC). LTA$_4$H Enzyme (1 nM final), Arg-AMC substrate (50 µM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm). In general, the preferred potency range (IC$_{50}$) of compounds in the LTA$_4$H Enzyme assay is between 0.1 nM to 10 µM, the more preferred potency range is 0.1 nM to 0.1 µM, and the most preferred potency range is 0.1 nM to 10 nM.

TABLE 9

IC$_{50}$ values of LTA$_4$H Enzyme assay.

| Example | IC$_{50}$ (nM) | Example | IC$_{50}$ (nM) |
|---|---|---|---|
| 1 | 0.38 | 121 | 0.37 |
| 2 | 2.45 | 122 | 0.91 |
| 3 | 2.57 | 123 | 0.73 |
| 4 | 0.74 | 124 | 2.45 |
| 5 | 2.96 | 125 | 0.16 |
| 6 | 0.46 | 126 | 0.18 |
| 7 | 2.79 | 127 | 0.12 |
| 8 | 0.32 | 128 | 0.65 |
| 9 | 1.49 | 129 | 0.23 |
| 10 | 0.75 | 130 | 0.51 |
| 11 | 2.95 | 131 | 1.73 |
| 12 | 10.19 | 132 | 0.91 |
| 13 | 0.36 | 133 | 1.75 |
| 14 | 0.27 | 134 | 0.47 |
| 15 | 0.36 | 135 | 0.47 |
| 16 | 2.32 | 136 | 0.19 |
| 17 | 0.77 | 137 | 0.26 |
| 18 | 1.14 | 138 | 0.18 |
| 19 | 0.73 | 139 | 0.10 |
| 20 | 1.30 | 140 | 0.38 |
| 21 | 4.43 | 141 | 0.26 |
| 22 | 200.00 | 142 | 0.17 |
| 23 | 5.20 | 143 | 0.30 |
| 24 | 5.90 | 144 | 0.14 |
| 25 | 0.76 | 145 | 0.09 |
| 26 | 0.43 | 146 | 0.29 |
| 27 | 1.20 | 147 | 0.35 |
| 28 | 3.40 | 148 | 0.28 |
| 29 | 2.04 | 149 | 0.24 |
| 30 | 1.77 | 150 | 0.21 |
| 31 | 1.54 | 151 | 0.10 |
| 32 | 1.80 | 152 | 0.17 |
| 33 | 3.19 | 153 | 0.82 |
| 34 | 1.89 | 154 | 0.20 |
| 35 | 0.26 | 155 | 0.28 |
| 36 | 4.45 | 156 | 0.91 |
| 37 | 1.05 | 157 | 0.18 |
| 38 | 1.14 | 158 | 0.13 |
| 39 | 2.14 | 159 | 0.16 |
| 40 | 0.82 | 160 | 0.18 |
| 41 | 3.71 | 161 | 0.41 |
| 42 | 0.69 | 162 | 0.14 |
| 43 | 4.42 | 163 | 0.17 |
| 44 | 0.69 | 164 | 0.84 |
| 45 | 0.90 | 165 | 0.13 |
| 46 | 24.82 | 166 | 0.68 |
| 47 | 1.73 | 167 | 0.27 |
| 48 | 0.16 | 168 | 0.31 |
| 49 | 0.32 | 169 | 0.33 |
| 50 | 0.60 | 170 | 0.47 |
| 51 | 0.82 | 171 | 0.45 |
| 52 | 0.75 | 172 | 0.53 |
| 53 | 0.42 | 173 | 0.73 |
| 54 | 5.93 | 174 | 0.60 |
| 55 | 3.63 | 175 | 0.22 |
| 56 | 6.08 | 176 | 0.24 |
| 57 | 13.66 | 177 | 1.45 |
| 58 | 1.36 | 178 | 0.35 |
| 59 | 89.24 | 179 | 0.16 |
| 60 | 31.02 | 180 | 0.12 |
| 61 | 0.60 | 181 | 0.042 |
| 62 | 1.79 | 182 | 0.29 |
| 63 | 7.90 | 183 | 0.48 |
| 64 | 0.83 | 184 | 0.11 |
| 65 | 1.15 | 185 | 0.59 |
| 66 | 1.79 | 186 | 0.24 |
| 67 | 0.61 | 187 | 0.07 |
| 68 | 0.10 | 188 | 0.87 |
| 69 | 0.60 | 189 | 0.16 |
| 70 | 0.57 | 190 | 0.09 |
| 71 | 1.88 | 191 | 1.62 |
| 72 | 1.80 | 192 | 0.43 |
| 73 | 3.65 | 193 | 5.35 |
| 74 | 1.00 | 194 | 0.15 |
| 75 | 4.51 | 195 | 1.59 |
| 76 | 1.90 | 196 | 0.39 |
| 77 | 0.18 | 197 | 2.69 |
| 78 | 1.40 | 198 | 2.28 |
| 79 | 0.51 | 199 | 40.12 |
| 80 | 0.71 | 200 | 0.12 |
| 81 | 0.31 | 201 | 1.59 |
| 82 | 0.20 | 202 | 23.37 |
| 83 | 0.13 | 203 | 2.94 |
| 84 | 2.69 | 204 | 0.15 |
| 85 | 0.45 | 205 | 27.50 |
| 86 | 0.92 | 206 | 0.19 |
| 87 | 0.69 | 207 | 0.86 |
| 88 | 0.54 | 208 | 21.45 |
| 89 | 1.40 | 209 | 12.41 |
| 90 | 0.77 | 210 | 19.00 |
| 91 | 0.54 | 211 | 0.69 |
| 92 | 35.99 | 212 | 0.49 |
| 93 | 1.98 | 213 | 0.81 |
| 94 | 0.45 | 214 | 0.47 |
| 95 | 0.49 | 215 | 0.70 |
| 96 | 0.22 | 216 | 0.13 |
| 97 | 2.87 | 217 | 2.28 |
| 98 | 0.61 | 218 | 0.37 |
| 99 | 0.37 | 219 | 0.49 |
| 100 | 2.36 | 220 | 0.47 |
| 101 | 1.90 | 221 | 0.16 |
| 102 | 2.68 | 222 | 0.14 |
| 103 | 2.40 | 223 | 0.16 |
| 104 | 0.18 | 224 | 0.13 |
| 105 | 0.51 | 225 | 5.30 |
| 106 | 0.46 | 226 | 42.95 |
| 107 | 1.35 | 227 | 1.40 |
| 108 | 0.87 | 228 | 0.61 |
| 109 | 0.17 | 229 | 3.85 |
| 110 | 2.15 | 230 | 1.24 |
| 111 | 2.25 | 231 | 0.29 |
| 112 | 1.07 | 232 | 2.75 |
| 113 | 2.49 | 233 | 0.22 |
| 114 | 0.77 | 234 | 0.14 |
| 115 | 3.03 | 235 | 0.08 |
| 116 | 0.82 | 236 | 6.04 |
| 117 | 0.23 | 237 | 0.81 |
| 118 | 0.45 | 238 | 0.55 |
| 119 | 0.10 | 239 | 0.15 |
| 120 | 0.51 | | |

The compounds of the invention are additionally tested in a human whole blood (HWB) assay to determine their ability to inhibit the synthesis of $LTB_4$ in a cellular system. Compounds are combined with heparinized human whole blood and incubated for 15 minutes at 37° C. Calcimycin (20 µM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma $LTB_4$ concentrations are then measured using an antibody-based homogenous time-resolved fluorescence method (CisBio, Bedford, Mass.). In general, the preferred potency range ($IC_{50}$) of compounds in the HWB assay is between 10 nM to 10 µM, the more preferred potency range is 10 nM to 1 µM, and the most preferred potency range is 10 nM to 100 nM. The potencies of representative compounds of the invention in the WHB assays are shown in Table 10.

TABLE 10

$IC_{50}$ values of $LTB_4$ production inhibition assay in human whole blood.

| Example | $IC_{50}$ (nM) | Example | $IC_{50}$ (nM) | Example | $IC_{50}$ (nM) | Example | $IC_{50}$ (nM) |
|---|---|---|---|---|---|---|---|
| 139 | 13.18 | 175 | 72.56 | 52 | 145.12 | 61 | 250.398 |
| 142 | 24.37 | 173 | 72.75 | 219 | 148.90 | 118 | 255.61 |
| 190 | 26.03 | 109 | 75.52 | 183 | 151.13 | 174 | 268.33 |
| 158 | 27.50 | 138 | 76.03 | 14 | 154.92 | 87 | 268.33 |
| 137 | 27.64 | 68 | 80.65 | 53 | 154.92 | 9 | 284.85 |
| 160 | 27.98 | 81 | 80.74 | 64 | 157.95 | 229 | 289.83 |
| 145 | 28.39 | 200 | 82.95 | 156 | 158.75 | 25 | 294.12 |
| 126 | 32.30 | 220 | 91.13 | 121 | 159.37 | 85 | 304.96 |
| 141 | 32.81 | 185 | 92.28 | 178 | 159.61 | 227 | 307.44 |
| 140 | 33.44 | 237 | 94.53 | 69 | 164.89 | 26 | 308.47 |
| 83 | 33.49 | 134 | 94.60 | 214 | 168.70 | 116 | 310.32 |
| 157 | 35.00 | 234 | 94.77 | 18 | 176.14 | 123 | 312.41 |
| 186 | 36.46 | 204 | 94.98 | 187 | 176.77 | 37 | 323.66 |
| 168 | 38.99 | 155 | 95.39 | 1 | 179.33 | 67 | 345.74 |
| 125 | 39.18 | 99 | 95.39 | 98 | 180.00 | 10 | 352.40 |

Methods of Use

The compounds of the invention are effective inhibitors of leukotriene $A_4$ hydrolase ($LTA_4H$) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of $LTA_4H$, the compounds of the invention block the production of $LTB_4$ resulting from the oxidation of arachidonic acid by 5-LO and subsequent metabolism. Thus, the inhibition of $LTA_4H$ activity is an attractive means for preventing and treating a variety of diseases mediated by $LTB_4$. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, inflammatory and allergic ocular diseases;

Cancer including solid tumors, leukemias and lymphomas; and Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery*

*Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound selected from the group consisting of:
1-[4-(2,3-dihydro-1,4-benzodioxin-2-yl)benzyl]pyrrolidine;
4-[4-(2,3-dihydro-1,4-benzodioxin-2-yl)benzyl]morpholine;
1-[4-(2,3-dihydro-1,4-benzodioxin-2-yl)benzyl]-4,4-dimethylpiperidine;
8-[4-(2,3-dihydro-1,4-benzodioxin-2-yl)benzyl]-2,8-diazaspiro[4,5]decan-1-one;
1-[4-(2,3-dihydro-1,4-benzodioxin-2-yl)benzyl]-4-fluoropiperidine;
(1s,4s)-7-[4-(2,3-dihydro-1,4-benzodioxin-2-yl)benzyl]-7-azabicyclo[2.2.1]heptane;
4-[4-(2,3-dihydro-1,4-benzodioxin-2-yl)benzyl]thiomorpholine 1,1-dioxide;
1-{4-[(2S)-2,3-dihydro-1,4-benzodioxin-2-yl]benzyl}-N,N-dimethylpiperidine-4-carboxamide;
(3S)-1-[4-(2,3-dihydro-1,4-benzodioxin-2-yl)benzyl]pyrrolidin-3-ol;
1-({1-[4-(2,3-dihydro-1,4-benzodioxin-2-yl)benzyl]piperidin-3-yl}methyl)pyrrolidin-2-one;
1-{4-[4-(2,3-dihydro-1,4-benzodioxin-2-yl)benzyl]piperazin-1-yl}ethanone;
2-{[4-(2,3-dihydro-1,4-benzodioxin-2-yl)benzyl]amino}-1-(pyrrolidin-1-yl)ethanone;
N-{4-[(2S)-2,3-dihydro-1,4-benzodioxin-2-yl]benzyl}-N-methyl-1-(methylsulfonyl)piperidin-4-amine;
1-{4-[{4-[(2S)-2,3-dihydro-1,4-benzodioxin-2-yl]benzyl}(methyl)amino]piperidin-1-yl}ethanone;
3-[4-(pyrrolidin-1-ylmethyl)phenyl]-2,3-dihydro[1,4]dioxino[2,3-b]pyridine;
7-[4-(2,3-dihydro-1,4-benzodioxin-2-yl)benzyl]-5,6,7,8-tetrahydro[1,2,4]triazolo[4,3-a]pyrazine;
3-{4-[(1,1-dioxidothiomorpholin-4-yl)methyl]phenyl}-2,3-dihydro[1,4]dioxino[2,3-b]pyridine;
3-[4-(morpholin-4-ylmethyl)phenyl]-2,3-dihydro[1,4]dioxino[2,3-b]pyridine;
(3R)-1-{4-[(2S)-2,3-dihydro-1,4-benzodioxin-2-yl]benzyl}piperidine-3-carboxylic acid;
(3S)-1-{4-[(2S)-2,3-dihydro-1,4-benzodioxin-2-yl]benzyl}piperidine-3-carboxylic acid;
1-(1-{4-[(2S)-2,3-dihydro-1,4-benzodioxin-2-yl]benzyl}piperidin-4-yl)-2,2,2-trifluoroethanol;
2-(1-{4-[(2S)-2,3-dihydro-1,4-benzodioxin-2-yl]benzyl}piperidin-4-yl)-1,1,1,3,3,3-hexafluoropropan-2-ol;
N-[4-(2,3-dihydro-1,4-benzodioxin-2-yl)benzyl]-2-methylpropan-2-amine;
(2R)—N-[4-(2,3-dihydro-1,4-benzodioxin-2-yl)benzyl]butan-2-amine;
1-[4-(2,3-dihydro-1,4-benzodioxin-2-yl)benzyl]-N-methylpiperidine-4-carboxamide;
4-{1-[4-(2,3-dihydro-1,4-benzodioxin-2-yl)benzyl]piperidin-4-yl}butanoic acid;
{1-[4-(2,3-dihydro-1,4-benzodioxin-2-yl)benzyl]piperidin-4-yl}methanol;
2-{1-[4-(2,3-dihydro-1,4-benzodioxin-2-yl)benzyl]piperidin-4-yl}propan-2-ol;
3-{1-[4-(2,3-dihydro-1,4-benzodioxin-2-yl)benzyl]piperidin-4-yl}propan-1-ol;
1-[4-(2,3-dihydro-1,4-benzodioxin-2-yl)benzyl]-4-methyl-1,4-diazepane;
1-{4-[4-(2,3-dihydro-1,4-benzodioxin-2-yl)benzyl]-1,4-diazepan-1-yl}ethanone;
4-[4-(2,3-dihydro-1,4-benzodioxin-2-yl)benzyl]-1,4-oxazepane;
N-[4-(2,3-dihydro-1,4-benzodioxin-2-yl)benzyl]-2-methoxy-N-methylethanamine;
(3R)-1-[4-(2,3-dihydro-1,4-benzodioxin-2-yl)benzyl]pyrrolidin-3-ol;
8-[4-(2,3-dihydro-1,4-benzodioxin-2-yl)benzyl]-1,3,8-triazaspiro[4.5]decane-2,4-dione;
1-[4-(2,3-dihydro-1,4-benzodioxin-2-yl)benzyl]-3-methoxyazetidine;
{1-[4-(2,3-dihydro-1,4-benzodioxin-2-yl)benzyl]piperidin-4-yl}(morpholin-4-yl)methanone;
2-{1-[4-(2,3-dihydro-1,4-benzodioxin-2-yl)benzyl]piperidin-4-yl}-N,N-dimethylacetamide;
1-[4-(2,3-dihydro-1,4-benzodioxin-2-yl)benzyl]-4-(methylsulfonyl)piperidine;
1-[4-(2,3-dihydro-1,4-benzodioxin-2-yl)benzyl]azepane;
N-[4-(2,3-dihydro-1,4-benzodioxin-2-yl)benzyl]cyclopentanamine;
N-[4-(2,3-dihydro-1,4-benzodioxin-2-yl)benzyl]-N-methyl-2-(pyridin-2-yl)ethanamine;
1-cyclopropyl-N-[4-(2,3-dihydro-1,4-benzodioxin-2-yl)benzyl]methanamine;
1-[4-(2,3-dihydro-1,4-benzodioxin-2-yl)benzyl]-4-phenylpiperidin-4-ol;
N-[4-(2,3-dihydro-1,4-benzodioxin-2-yl)benzyl]-N-ethylethanamine;
1-[4-(2,3-dihydro-1,4-benzodioxin-2-yl)benzyl]azetidine-3-carbonitrile;
1-[4-(2,3-dihydro-1,4-benzodioxin-2-yl)benzyl]-3-methoxypyrrolidine;
N-{1-[4-(2,3-dihydro-1,4-benzodioxin-2-yl)benzyl]piperidin-4-yl}methanesulfonamide;
N-[4-(2,3-dihydro-1,4-benzodioxin-2-yl)benzyl]-2-methyl-1-(pyrrolidin-1-yl)propan-2-amine;
1-({1-[4-(2,3-dihydro-1,4-benzodioxin-2-yl)benzyl]piperidin-4-yl}methyl)pyrrolidin-2-one;
1-[4-(2,3-dihydro-1,4-benzodioxin-2-yl)benzyl]-N,N-dimethylpiperidine-4-carboxamide;
1-[4-(2,3-dihydro-1,4-benzodioxin-2-yl)benzyl]-N-(2-hydroxyethyl)piperidine-4-carboxamide;
1-{1-[4-(2,3-dihydro-1,4-benzodioxin-2-yl)benzyl]piperidin-4-yl}urea;
1-[4-(2,3-dihydro-1,4-benzodioxin-2-yl)phenyl]-N-yridin-3-ylmethyl)methanamine;
1-[4-(2,3-dihydro-1,4-benzodioxin-2-yl)phenyl]-N-[(1-methyl-1H-imidazol-4-yl)methyl]methanamine;
2-{4-[(2S)-2,3-dihydro-1,4-benzodioxin-2-yl]benzyl}-1,2,3,4-tetrahydroisoquinoline-4-carboxylic acid;
(1R,3S)-3-({4-[(2S)-2,3-dihydro-1,4-benzodioxin-2-yl]benzyl}amino)cyclopentanecarboxylic acid;
3-({4-[(2S)-2,3-dihydro-1,4-benzodioxin-2-yl]benzyl}amino)-4,4-dimethylpentanoic acid;
1-({4-[(2S)-2,3-dihydro-1,4-benzodioxin-2-yl]benzyl}amino)cyclopentanecarboxylic acid;
N-{4-[(2S)-2,3-dihydro-1,4-benzodioxin-2-yl]benzyl}-N-methylglycine;
1-{4-[(2S)-2,3-dihydro-1,4-benzodioxin-2-yl]benzyl}pyrrolidine-3-carboxylic acid;
trans-4-({4-[(2S)-2,3-dihydro-1,4-benzodioxin-2-yl]benzyl}amino)cyclohexanecarboxylic acid;

cis-4-({4-[(2S)-2,3-dihydro-1,4-benzodioxin-2-yl]benzyl}amino)cyclohexanecarboxylic acid;
1-[(3R)-3-({4-[(2S)-2,3-dihydro-1,4-benzodioxin-2-yl]benzyl}amino)pyrrolidin-1-yl]ethanone;
1-[(3S)-3-({4-[(2S)-2,3-dihydro-1,4-benzodioxin-2-yl]benzyl}amino)pyrrolidin-1-yl]ethanone;
trans-4-({4-[(2S)-2,3-dihydro-1,4-benzodioxin-2-yl]benzyl}amino)cyclohexanecarboxamide;
N-{4-[(2S)-2,3-dihydro-1,4-benzodioxin-2-yl]benzyl}-N-methylcyclohexanamine;
(1-{4-[(2S)-2,3-dihydro-1,4-benzodioxin-2-yl]benzyl}piperidin-3-yl)methanol;
2-(1-{4-[(2S)-2,3-dihydro-1,4-benzodioxin-2-yl]benzyl}piperidin-4-yl)ethanol;
N-{4-[(2S)-2,3-dihydro-1,4-benzodioxin-2-yl]benzyl}propan-2-amine;
N-{4-[(2S)-2,3-dihydro-1,4-benzodioxin-2-yl]benzyl}-1-methoxypropan-2-amine;
N-{4-[(2S)-2,3-dihydro-1,4-benzodioxin-2-yl]benzyl}propan-1-amine;
N-{4-[(2S)-2,3-dihydro-1,4-benzodioxin-2-yl]benzyl}-N-methylethanamine;
1-{4-[(2S)-2,3-dihydro-1,4-benzodioxin-2-yl]phenyl}-N,N-dimethylmethanamine;
trans-4-({4-[(2S)-2,3-dihydro-1,4-benzodioxin-2-yl]benzyl}amino)cyclohexanol;
1-{4-[(2S)-2,3-dihydro-1,4-benzodioxin-2-yl]benzyl}piperidin-3-ol;
N-{4-[(2S)-2,3-dihydro-1,4-benzodioxin-2-yl]benzyl}-N,N',N'-trimethylethane-1,2-diamine;
2-(cyclohexyl {4-[(2S)-2,3-dihydro-1,4-benzodioxin-2-yl]benzyl}amino)ethanol;
(1R,2R,4S)—N-{4-[(2S)-2,3-dihydro-1,4-benzodioxin-2-yl]benzyl}bicyclo[2.2.1]heptan-2-amine;
(4aR,8aS)-1-{4-[(2S)-2,3-dihydro-1,4-benzodioxin-2-yl]benzyl}decahydroquinoline;
(1S,2R)-2-({4-[(2S)-2,3-dihydro-1,4-benzodioxin-2-yl]benzyl}amino)cyclohexanecarboxamide;
[(1S,2R)-2-({4-[(2S)-2,3-dihydro-1,4-benzodioxin-2-yl]benzyl}amino)cyclohexyl]methanol;
(3R)-1-{4-[(2S)-2,3-dihydro-1,4-benzodioxin-2-yl]benzyl}pyrrolidin-3-ol;
[(1R,2R)-2-({4-[(2S)-2,3-dihydro-1,4-benzodioxin-2-yl]benzyl}amino)cyclohexyl]methanol;
(1-{4-[(2S)-2,3-dihydro-1,4-benzodioxin-2-yl]benzyl}piperidin-4-yl)methanol;
(3S)-1-{4-[(2S)-2,3-dihydro-1,4-benzodioxin-2-yl]benzyl}pyrrolidin-3-ol;
1-{4-[(2S)-2,3-dihydro-1,4-benzodioxin-2-yl]benzyl}imidazolidin-4-one;
1-{4-[(2S)-2,3-dihydro-1,4-benzodioxin-2-yl]benzyl}-N,N-dimethylpyrrolidin-3-amine;
1'-{4-[(2S)-2,3-dihydro-1,4-benzodioxin-2-yl]benzyl}-1,4'-bipiperidin-2-one;
N-(cyclopropylmethyl)-N-{4-[(2S)-2,3-dihydro-1,4-benzodioxin-2-yl]benzyl}cyclohexanamine;
(1R,2R)-2-({4-[(2S)-2,3-dihydro-1,4-benzodioxin-2-yl]benzyl}amino)cyclohexanol;
1-{4-[(2S)-2,3-dihydro-1,4-benzodioxin-2-yl]benzyl}-4-methoxypiperidine;
1-[(1-{4-[(2S)-2,3-dihydro-1,4-benzodioxin-2-yl]benzyl}piperidin-4-yl)methyl]pyrrolidin-2-one;
trans-N-{4-[(2S)-2,3-dihydro-1,4-benzodioxin-2-yl]benzyl}-4-methylcyclohexanamine;
(1S,2R)-2-({4-[(2S)-2,3-dihydro-1,4-benzodioxin-2-yl]benzyl}amino)cyclopentanol;
(1S,2S)-2-({4-[(2S)-2,3-dihydro-1,4-benzodioxin-2-yl]benzyl}amino)cyclopentanol;
N-{4-[(2S)-2,3-dihydro-1,4-benzodioxin-2-yl]benzyl}tetrahydro-2H-pyran-3-amine;
(1S,2S)-2-[{4-[(2S)-2,3-dihydro-1,4-benzodioxin-2-yl]benzyl}(methyl)amino]cyclohexanol;
(1R,2S)-2-[{ 4-[(2S)-2,3-dihydro-1,4-benzodioxin-2-yl]benzyl}(methyl)amino]cyclohexanol;
4-{4-[(2S)-2,3-dihydro-1,4-benzodioxin-2-yl]benzyl}-3-methylmorpholine;
5-({4-[(2S)-2,3-dihydro-1,4-benzodioxin-2-yl]benzyl}amino)-1-methylpiperidin-2-one;
N-{4-[(2S)-2,3-dihydro-1,4-benzodioxin-2-yl]benzyl}-N,1-dimethylpiperidin-4-amine;
4-[({4-[(2S)-2,3-dihydro-1,4-benzodioxin-2-yl]benzyl}amino)methyl]phenol;
2-{4-[(2S)-2,3-dihydro-1,4-benzodioxin-2-yl]benzyl}-1,2,3,4-tetrahydroisoquinolin-6-ol;
1-[4-(2,3-dihydro-1,4-benzodioxin-2-yl)benzyl]piperidine-3-carboxylic acid;
1-[4-(2,3-dihydro-1,4-benzodioxin-2-yl)benzyl]piperidine-3-carboxamide;
(3S)-1-[4-(2,3-dihydro-1,4-benzodioxin-2-yl)benzyl]-3-fluoropyrrolidine;
9-{4-[(2S)-2,3-dihydro-1,4-benzodioxin-2-yl]benzyl}-2,9-diazaspiro[5.5]undecan-1-one;
1-(7-{4-[(2S)-2,3-dihydro-1,4-benzodioxin-2-yl]benzyl}-1,7-diazaspiro[4.4]non-1-yl)ethanone;
9-{4-[(2S)-2,3-dihydro-1,4-benzodioxin-2-yl]benzyl}-2-methyl-2,9-diazaspiro[5.5]undecan-1-one;
8-{4-[(2S)-2,3-dihydro-1,4-benzodioxin-2-yl]benzyl}-2-methyl-2,8-diazaspiro[4.5]decan-1-one;
7-{4-[(2S)-2,3-dihydro-1,4-benzodioxin-2-yl]benzyl}-1-(methylsulfonyl)-1,7-diazaspiro[4.4]nonane;
2-(7-{4-[(2S)-2,3-dihydro-1,4-benzodioxin-2-yl]benzyl}-1,7-diazaspiro[4.4]non-1-yl)acetamide;
(7-{4-[(2S)-2,3-dihydro-1,4-benzodioxin-2-yl]benzyl}-1,7-diazaspiro[4.4]non-1-yl)acetonitrile;
1-(7-{4-[(2S)-2,3-dihydro-1,4-benzodioxin-2-yl]benzyl}-1,7-diazaspiro[4.4]non-1-yl)-2-methoxyethanone;
9-[(S)-4-(2,3-Dihydro-benzo[1,4]dioxin-2-yl)-benzyl]-2-methyl-2,9-diaza-spiro[5.5]undecan-1-one;
1-{4-[(2S)-2,3-dihydro-1,4-benzodioxin-2-yl]benzyl}-1,4-diazepan-5-one;
1-{4-[(3S)-2,3-dihydro[1,4]dioxino[2,3-b]pyridin-3-yl]benzyl}-1,4-diazepan-5-one;
N-[2-({4-[(3S)-2,3-dihydro[1,4]dioxino[2,3-b]pyridin-3-yl]benzyl}amino)ethyl]acetamide;
3-(1-{4-[(2S)-2,3-dihydro-1,4-benzodioxin-2-yl]benzyl}piperidin-4-yl)propanoic acid;
N-{4-[(3S)-2,3-dihydro[1,4]dioxino[2,3-b]pyridin-3-yl]benzyl}cyclopentanamine;
N-{4-[(3S)-2,3-dihydro[1,4]dioxino[2,3-b]pyridin-3-yl]benzyl}-N-methylethanamine;
(3S)-3-{4-[(1s,4s)-7-azabicyclo[2.2.1]hept-7-ylmethyl]phenyl}-2,3-dihydro[1,4]dioxino[2,3-b]pyridine;
(3S)-1-{4-[(3S)-2,3-dihydro[1,4]dioxino[2,3-b]pyridin-3-yl]benzyl}pyrrolidin-3-ol;
4-(1-{4-[(3S)-2,3-dihydro[1,4]dioxino[2,3-b]pyridin-3-yl]benzyl}piperidin-4-yl)butanoic acid;
1-[4-({4-[(3S)-2,3-dihydro[1,4]dioxino[2,3-b]pyridin-3-yl]benzyl}amino)piperidin-1-yl]ethanone;
(3S)-3-{4-(5,6-dihydro[1,2,4]triazolo[4,3-a]pyrazin-7(8H)-ylmethyl)phenyl}-2,3-dihydro[1,4]dioxino[2,3-b]pyridine;
(3S)-3-{4-[(1,1-dioxidothiomorpholin-4-yl)methyl]phenyl}-2,3-dihydro[1,4]dioxino[2,3-b]pyridine;

4-{4-[(3S)-2,3-dihydro[1,4]dioxino[2,3-b]pyridin-3-yl]benzyl}piperazine-1-carboxamide;
(3S)-3-{4-[(3-methoxyazetidin-1-yl)methyl]phenyl}-2,3-dihydro[1,4]dioxino[2,3-b]pyridine;
N-{4-[(3S)-2,3-dihydro[1,4]dioxino[2,3-b]pyridin-3-yl]benzyl}-N-methyl-1-(methylsulfonyl)piperidin-4-amine;
(3S)-3-(4-{[4-(2-methoxyethoxyl)piperidin-1-yl]methyl}phenyl)-2,3-dihydro[1,4]dioxino[2,3-b]pyridine;
2-(1-{4-[(3S)-2,3-dihydro[1,4]dioxino[2,3-b]pyridin-3-yl]benzyl}piperidin-4-yl)-N,N-dimethylacetamide;
(3S)-3-(4-{[4-(methylsulfonyl)piperidin-1-yl]methyl}phenyl)-2,3-dihydro[1,4]dioxino[2,3-b]pyridine;
N-{4-[(3S)-2,3-dihydro[1,4]dioxino[2,3-b]pyridin-3-yl]benzyl}cyclobutanamine;
N-{4-[(2S)-2,3-dihydro-1,4-benzodioxin-2-yl]benzyl}-1-(methylsulfonyl)piperidin-4-amine;
1-{4-[(2S)-2,3-dihydro-1,4-benzodioxin-2-yl]benzyl}piperidine-4-carbonitrile;
N-(1-{4-[(2S)-2,3-dihydro-1,4-benzodioxin-2-yl]benzyl}piperidin-4-yl)acetamide;
[(3S)-1-{4-[(2S)-2,3-dihydro-1,4-benzodioxin-2-yl]benzyl}piperidin-3-yl]acetic acid;
[(3R)-1-{4-[(2S)-2,3-dihydro-1,4-benzodioxin-2-yl]benzyl}pyrrolidin-3-yl]acetic acid;
1-(4-{4-[(3S)-2,3-dihydro[1,4]dioxino[2,3-b]pyridin-3-yl]benzyl}piperazin-1-yl)ethanone;
1-{4-[(3S)-2,3-dihydro[1,4]dioxino[2,3-b]pyridin-3-yl]benzyl}piperidin-4-ol;
1-(1-{4-[(3S)-2,3-dihydro[1,4]dioxino[2,3-b]pyridin-3-yl]benzyl}piperidin-4-yl)urea;
(3S)-3-(4-{[4-(methylsulfonyl)piperazin-1-yl]methyl}phenyl)-2,3-dihydro[1,4]dioxino[2,3-b]pyridine;
1-{4-[(3S)-2,3-dihydro[1,4]dioxino[2,3-b]pyridin-3-yl]benzyl}piperidine-4-carboxylic acid;
(1S,3R)-3-({4-[(2S)-2,3-dihydro-1,4-benzodioxin-2-yl]benzyl}amino)cyclopentanecarboxylic acid;
1-{4-[(2S)-2,3-dihydro-1,4-benzodioxin-2-yl]benzyl}piperidin-4-ol;
1-{4-[(2R)-2,3-dihydro-1,4-benzodioxin-2-yl]benzyl}piperidin-4-ol;
8-{4-[(2R)-2,3-dihydro-1,4-benzodioxin-2-yl]benzyl}-2,8-diazaspiro[4.5]decan-1-one;
1-{4-[(2S)-2,3-dihydro-1,4-benzodioxin-2-yl]benzyl}pyrrolidine;
1-{4-[(2R)-2,3-dihydro-1,4-benzodioxin-2-yl]benzyl}pyrrolidine;
4-{4-[(2S)-2,3-dihydro-1,4-benzodioxin-2-yl]benzyl}morpholine;
4-{4-[(2R)-2,3-dihydro-1,4-benzodioxin-2-yl]benzyl}morpholine;
1-{4-[(2R)-2,3-dihydro-1,4-benzodioxin-2-yl]benzyl}piperidine-4-carboxylic acid;
4-[4-(7-fluoro-2,3-dihydro-1,4-benzodioxin-2-yl)benzyl]morpholine;
1-[4-(7-fluoro-2,3-dihydro-1,4-benzodioxin-2-yl)benzyl]pyrrolidine;
(3R)-3-[4-(morpholin-4-ylmethyl)phenyl]-2,3-dihydro[1,4]dioxino[2,3-b]pyridine;
1-{4-[(3R)-2,3-dihydro[1,4]dioxino[2,3-b]pyridin-3-yl]benzyl}piperidine-4-carboxamide;
1-[4-(2,3-dihydro[1,4]dioxino[2,3-b]pyridin-3-yl)benzyl]pyrrolidin-2-one;
3-[4-(2,3-dihydro[1,4]dioxino[2,3-b]pyridin-3-yl)benzyl]-1,3-oxazolidin-2-one;
1-[4-(2,3-dihydro[1,4]dioxino[2,3-b]pyridin-3-yl)phenyl]methanamine;
1-{4-[(2S)-2,3-dihydro-1,4-benzodioxin-2-yl]benzyl}-4-methylpiperidine-4-carboxylic acid;
(3R,4R)-1-{4-[(2S)-2,3-dihydro-1,4-benzodioxin-2-yl]benzyl}-3-methylpiperidine-4-carboxylic acid;
1-{4-[(2S)-2,3-dihydro-1,4-benzodioxin-2-yl]benzyl}-4-fluoropiperidine-4-carboxylic acid;
(3R)-1-{4-[(2S)-2,3-dihydro-1,4-benzodioxin-2-yl]benzyl}pyrrolidine-3-carboxylic acid;
(3S)-1-{4-[(2S)-2,3-dihydro-1,4-benzodioxin-2-yl]benzyl}pyrrolidine-3-carboxylic acid;
1-{4-[(2S)-2,3-dihydro-1,4-benzodioxin-2-yl]benzyl}-4-(1H-tetrazol-5-yl)piperidine;
1-{4-[(2S)-2,3-dihydro-1,4-benzodioxin-2-yl]benzyl}piperidin-4-amine;
N-(1-{4-[(2S)-2,3-dihydro-1,4-benzodioxin-2-yl]benzyl}piperidin-4-yl)-2-hydroxyacetamide;
N-(1-{4-[(2S)-2,3-dihydro-1,4-benzodioxin-2-yl]benzyl}piperidin-4-yl)-2-methoxyacetamide;
N-(1-{4-[(2S)-2,3-dihydro-1,4-benzodioxin-2-yl]benzyl}piperidin-4-yl)-2-hydroxy-2-methylpropanamide;
1-(1-{4-[(2S)-2,3-dihydro-1,4-benzodioxin-2-yl]phenyl}ethyl)pyrrolidine;
4-(1-{4-[(2S)-2,3-dihydro-1,4-benzodioxin-2-yl]phenyl}ethyl)morpholine;
1-(1-{4-[(2S)-2,3-dihydro-1,4-benzodioxin-2-yl]phenyl}ethyl)piperidine-4-carboxylic acid;
1-{4-[(3S)-2,3-dihydro[1,4]dioxino[2,3-b]pyridin-3-yl]benzyl}-4-methylpiperidine-4-carboxylic acid;
2-(1-{4-[(2S)-2,3-dihydro-1,4-benzodioxin-2-yl]benzyl}piperidin-4-yl)-2-methylpropanoic acid;
2-(1-{4-[(3S)-2,3-dihydro[1,4]dioxino[2,3-b]pyridin-3-yl]benzyl}piperidin-4-yl)-2-methylpropanoic acid;
2-{4-[(2S)-2,3-dihydro-1,4-benzodioxin-2-yl]benzyl}-1,2,3,4-tetrahydroisoquinoline-7-carboxylic acid;
4-{[{4-[(2S)-2,3-dihydro-1,4-benzodioxin-2-yl]benzyl}(ethyl)amino]methyl}benzoic acid;
4-[(butyl{4-[(2S)-2,3-dihydro-1,4-benzodioxin-2-yl]benzyl}amino)methyl]benzoic acid;
3-{[{4-[(2S)-2,3-dihydro-1,4-benzodioxin-2-yl]benzyl}(ethyl)amino]methyl}benzoic acid; and
3-[(4-{4-[(2S)-2,3-dihydro-1,4-benzodioxin-2-yl]benzyl}piperazin-1-yl)methyl]benzoic acid; or
a pharmaceutically salt thereof of each of the foregoing.

2. A pharmaceutical composition comprising the compound of claim 1, or a pharmaceutically acceptable salt thereof, and a pharmaceutically acceptable excipient.

3. A method of treating a leukotriene-mediated disorder comprising administering a pharmaceutically effective amount of a compound of claim 1, or a pharmaceutically acceptable salt thereof, to a patient in need thereof, wherein said leukotriene-mediated disorder is mediated by leukotriene $A_4$ hydrolyse ($LTA_4H$) inhibition.

4. The method according to claim 1, wherein the leukotriene-mediated disorder is a cardiovascular disease selected from the group consisting of atherosclerosis, myocardial infarction, stroke, aortic aneurysm, sickle cell crisis, ischemia-reperfusion injury, pulmonary arterial hypertension and sepsis.

5. A method of treating atherosclerosis comprising administering a pharmaceutically effective amount of a compound of claim 1 to a patient in need thereof.

* * * * *